United States Patent
Srinivasan et al.

(10) Patent No.: US 10,864,244 B2
(45) Date of Patent: Dec. 15, 2020

(54) PEPTIDES AND METHODS FOR TREATMENT OF NEURODEGENERATIVE DISEASES

(71) Applicant: INDIANA UNIVERSITY RESEARCH AND TECHNOLOGY CORPORATION, Indianapolis, IN (US)

(72) Inventors: Mythily Srinivasan, Greenwood, IN (US); Debomoy Lahiri, Brownsburg, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 16/108,605

(22) Filed: Aug. 22, 2018

(65) Prior Publication Data
US 2019/0054137 A1    Feb. 21, 2019

Related U.S. Application Data

(63) Continuation-in-part of application No. PCT/US2017/018645, filed on Feb. 21, 2017.

(60) Provisional application No. 62/298,216, filed on Feb. 22, 2016.

(51) Int. Cl.
| | |
|---|---|
| *A61K 38/04* | (2006.01) |
| *A61K 38/10* | (2006.01) |
| *A61K 38/08* | (2019.01) |
| *A61P 25/28* | (2006.01) |
| *A61P 25/16* | (2006.01) |
| *A61P 29/00* | (2006.01) |

(52) U.S. Cl.
CPC .............. *A61K 38/04* (2013.01); *A61K 38/08* (2013.01); *A61K 38/10* (2013.01); *A61P 25/16* (2018.01); *A61P 25/28* (2018.01); *A61P 29/00* (2018.01)

(58) Field of Classification Search
None
See application file for complete search history.

(56) References Cited

U.S. PATENT DOCUMENTS

2013/0330335 A1   12/2013   Bremel et al.
2014/0186372 A1   7/2014   Altman et al.

OTHER PUBLICATIONS

Srinivasan et al., Novel p65 Binding Glucocorticoid-induced Leucine Zipper Peptide Suppresses Experimental Autoimmune Encephalomyelitis, Dec. 30, 2011, The Journal of Biological Chemistry 286(52): 44799-44810 (Year: 2011).*
Srinivasan et al., Functional characterization of a competitive peptide antagonist of p65 in human macrophagelike cells suggests therapeutic potential for chronic inflammation, 2014, Drug Design, Development and Therapy 2014(8):2409-2421 (Year: 2014).*
PCT International Search Report and Written Opinion completed by the ISA/US dated Jun. 30, 2017 and issued in connection with PCT/US2017/018645.
Zafar, et al. "Chromatinized Protein Kinase C-theta Directly Regulates Inducible Genes in Epithelial to Mesenchymal Transition and Breast Cancer Stem Cells" Mol. Cell. Biol. (Aug. 2014) vol. 34 No. 16, pp. 2961-2980, p. 2961, col. 2, para 2, p. 2977, col. 2, para 2.
Cohen et al., Arresting tissue invasion of a parasite by protease inhibitors chosen with the aid of computer modeling, Biochemistry, Nov. 26, 1991, 30(47):11221-11229.
Sukuru et al., Discovering new classes of Brugia malayi asparaginyl-tRNA synthetase inhibitors and relating specificity to conformational change, J Comput Aided Mol Des., 2006, 20(3):159-178.

* cited by examiner

*Primary Examiner* — John D Ulm

(57) ABSTRACT

The present disclosure provides pharmaceutical compositions comprising rationally designed peptide analogs of the p65-TAD binding region of GILZ to selectively sequester activated p65. Structural and functional analyses suggest that select GILZ analog (GA) bind p65-TAD with optimum affinity, exhibit an estimated half minimal lethal dose comparable to known peptide drugs and suppress Aβ1-42 induced cytotoxicity. Furthermore, the present disclosure provides uses and methods of using the pharmaceutical compositions, and uses and methods of using pharmaceutical formulations comprising the pharmaceutical compositions, for the treatment of neurodegenerative diseases such as Alzheimer's Disease, Parkinson's Disease, multiple sclerosis, and amyotrophic lateral sclerosis (ALS).

19 Claims, 48 Drawing Sheets
Specification includes a Sequence Listing.

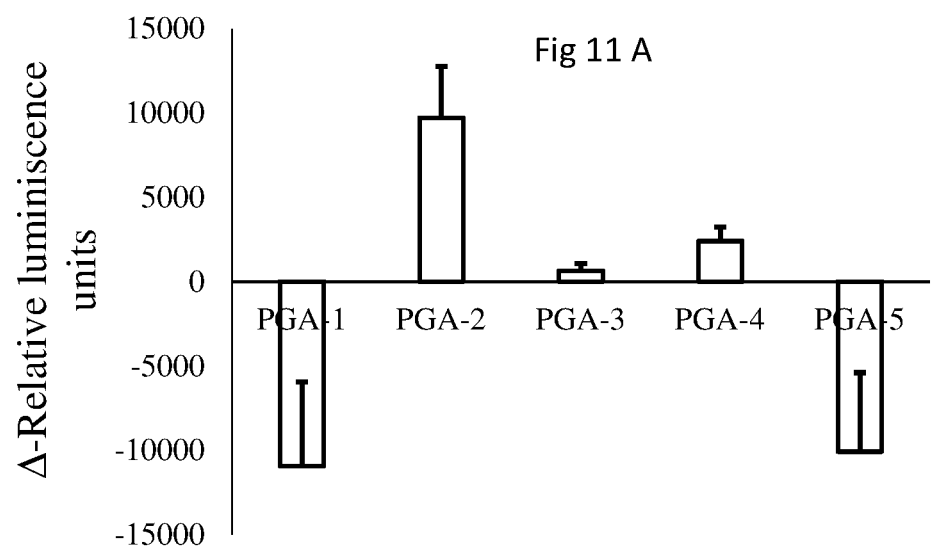

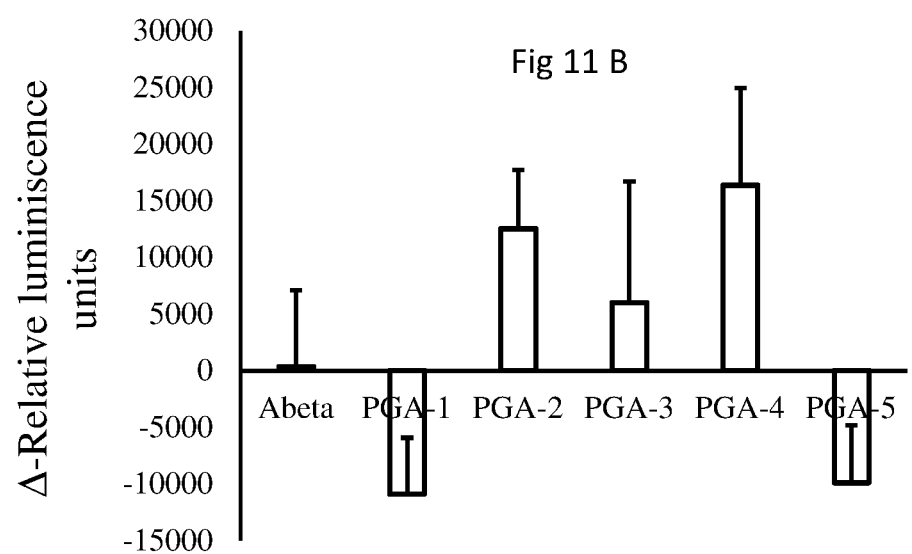

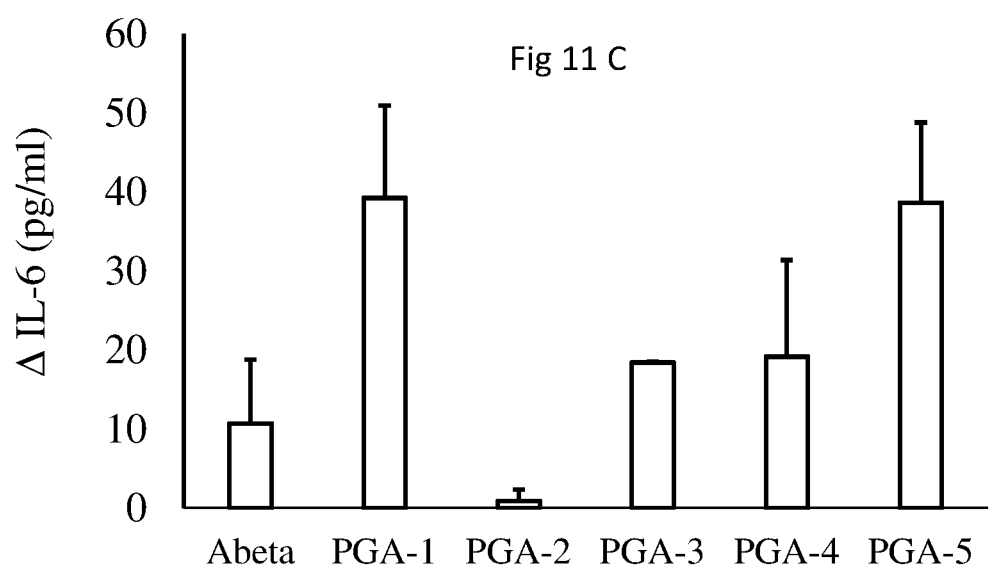

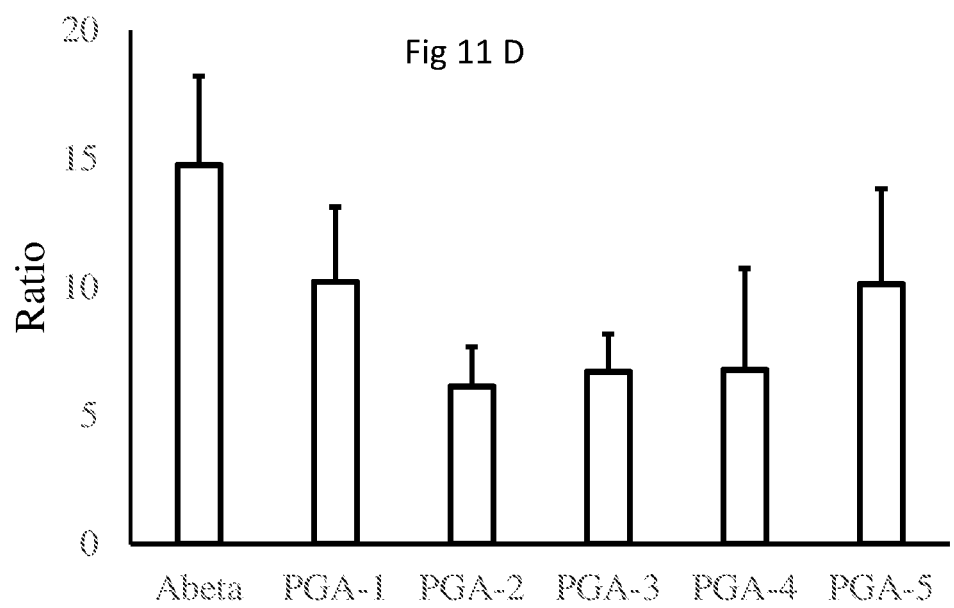

FIG. 12

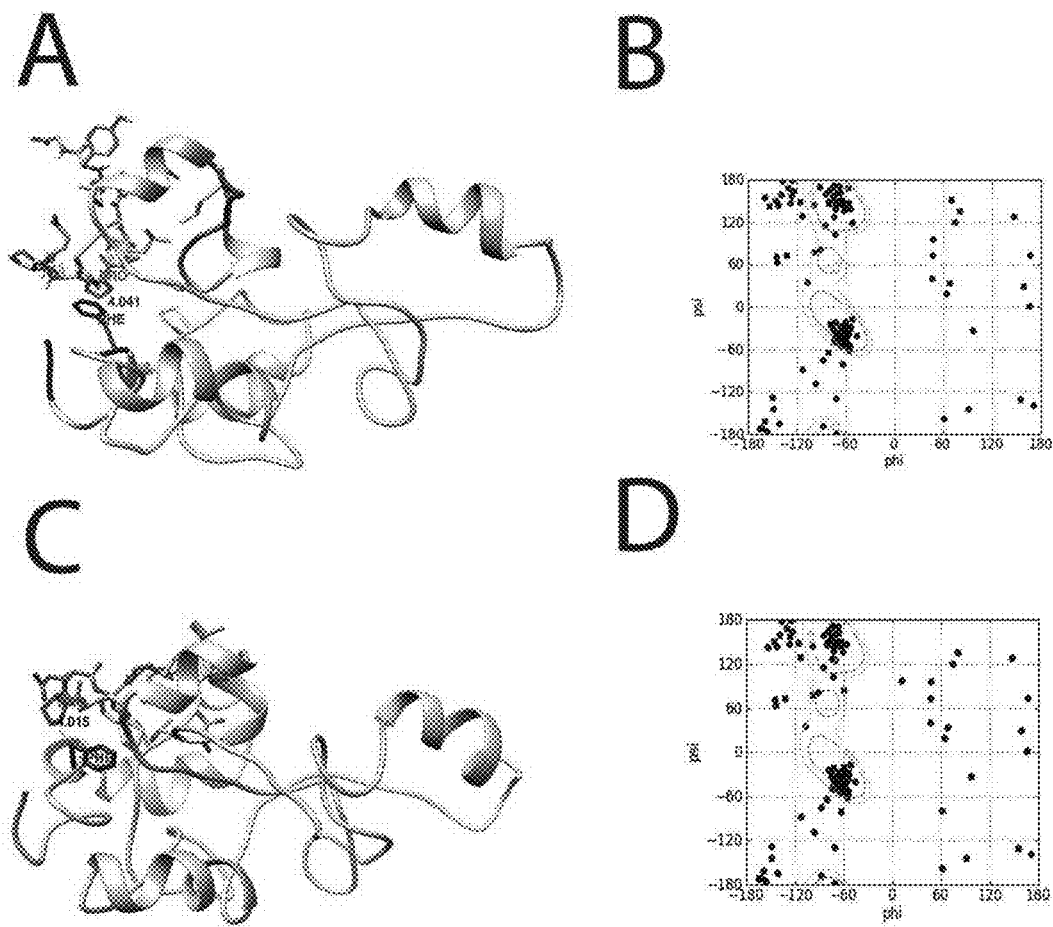
FIG. 14 A-D

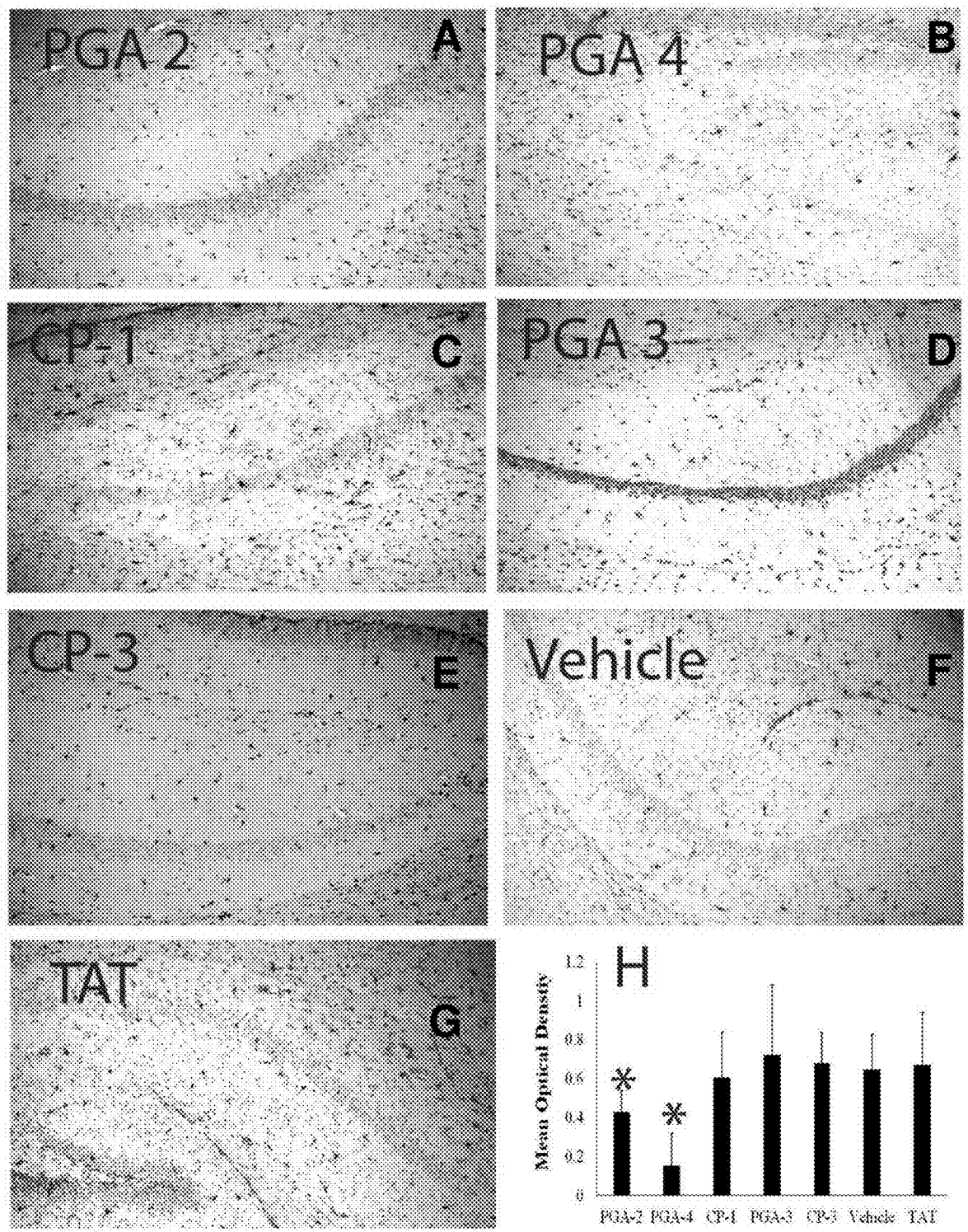
FIG. 15 A-H

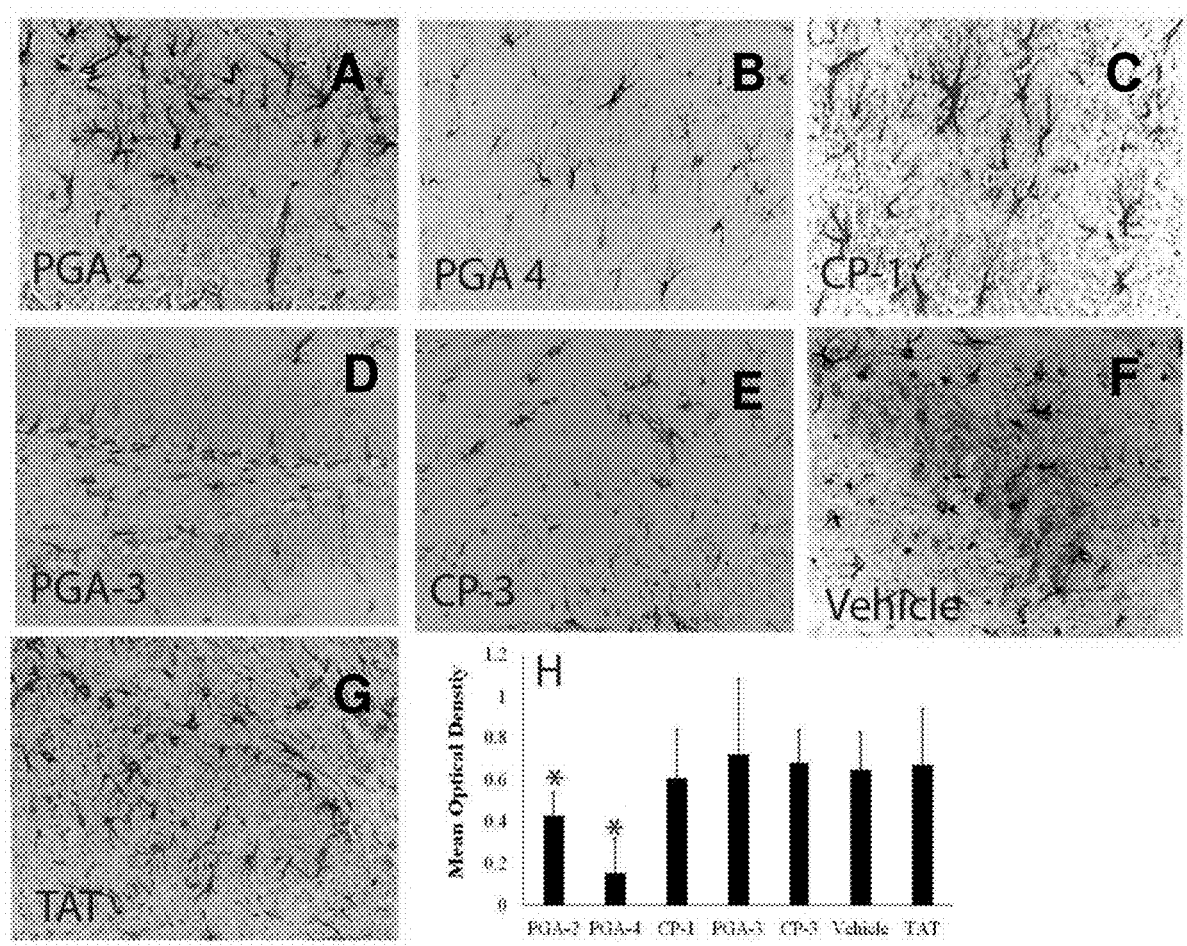
FIG. 16 A-H

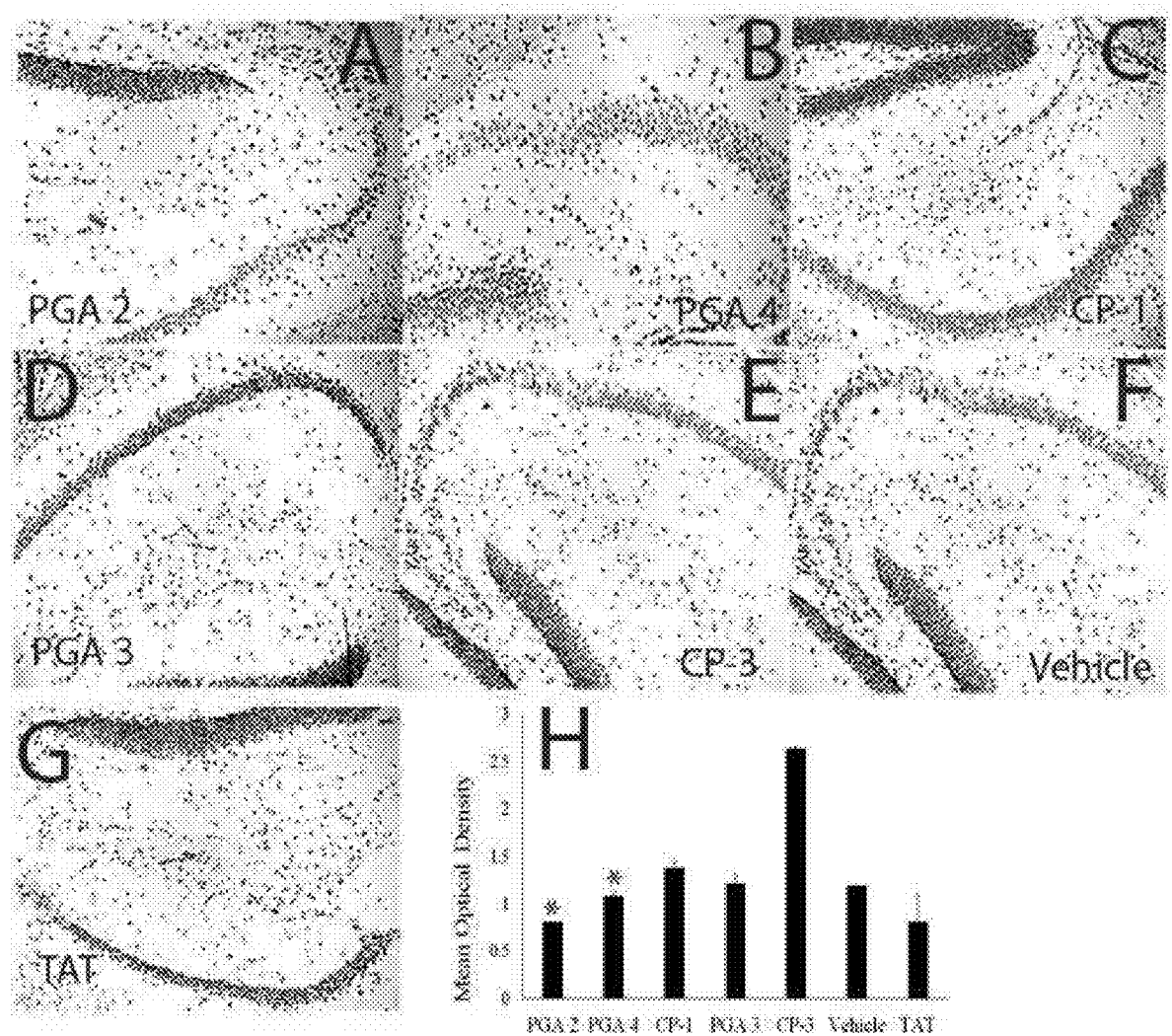
FIG. 17 A-H

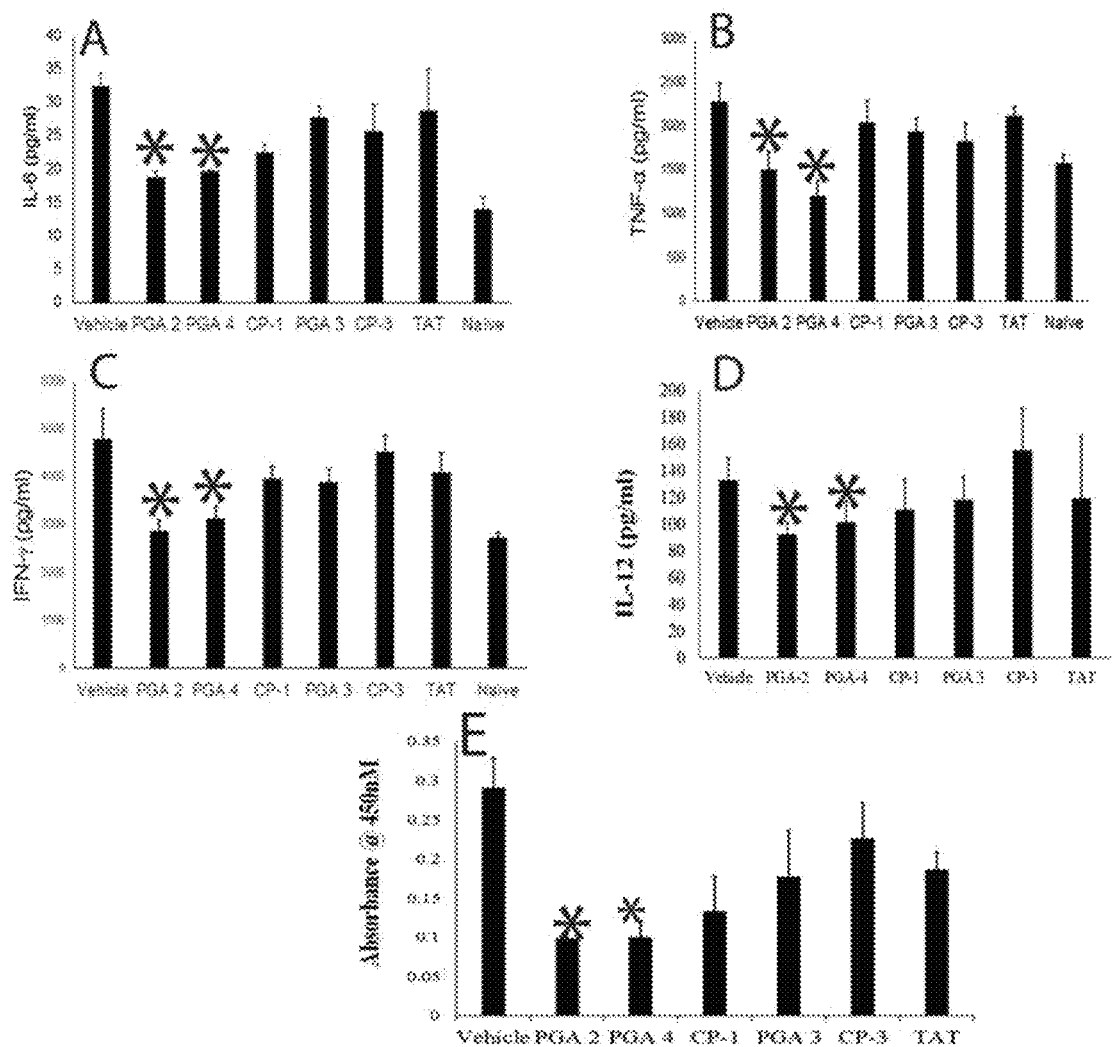
FIG. 18 A-E

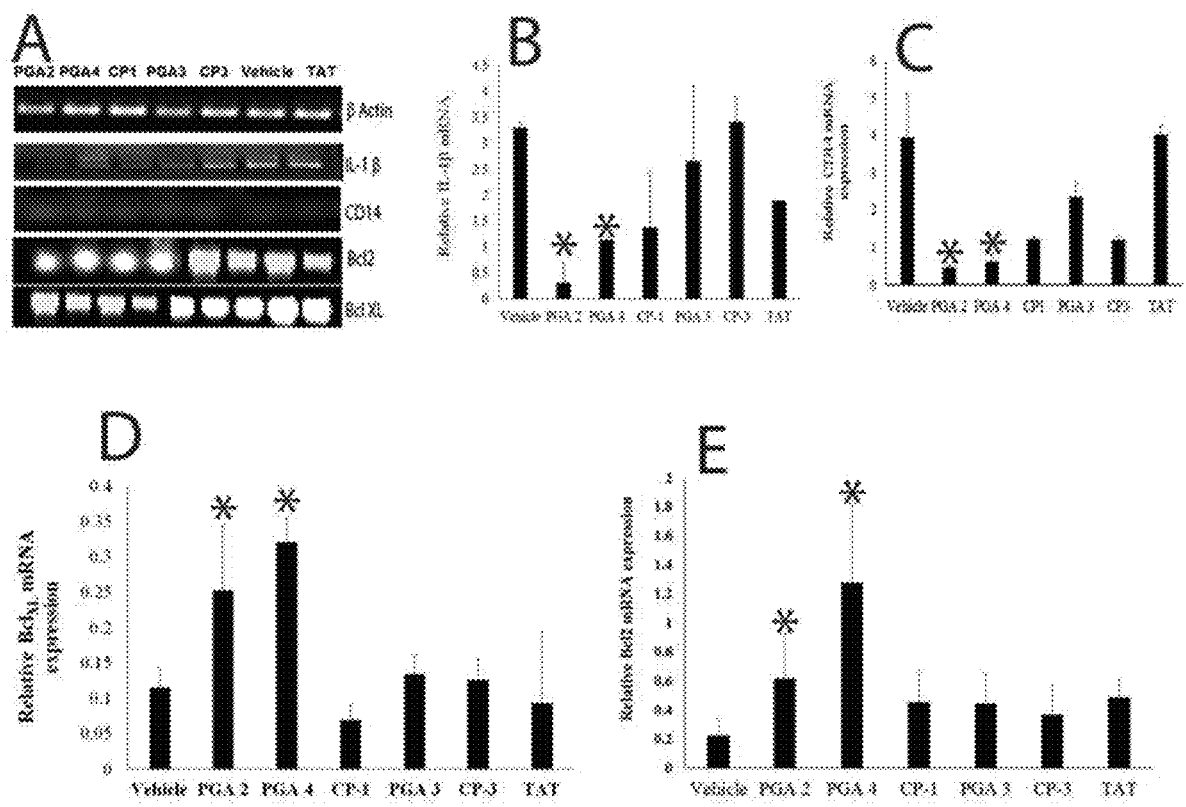
FIG.19 A-E

FIG. 20 A-D

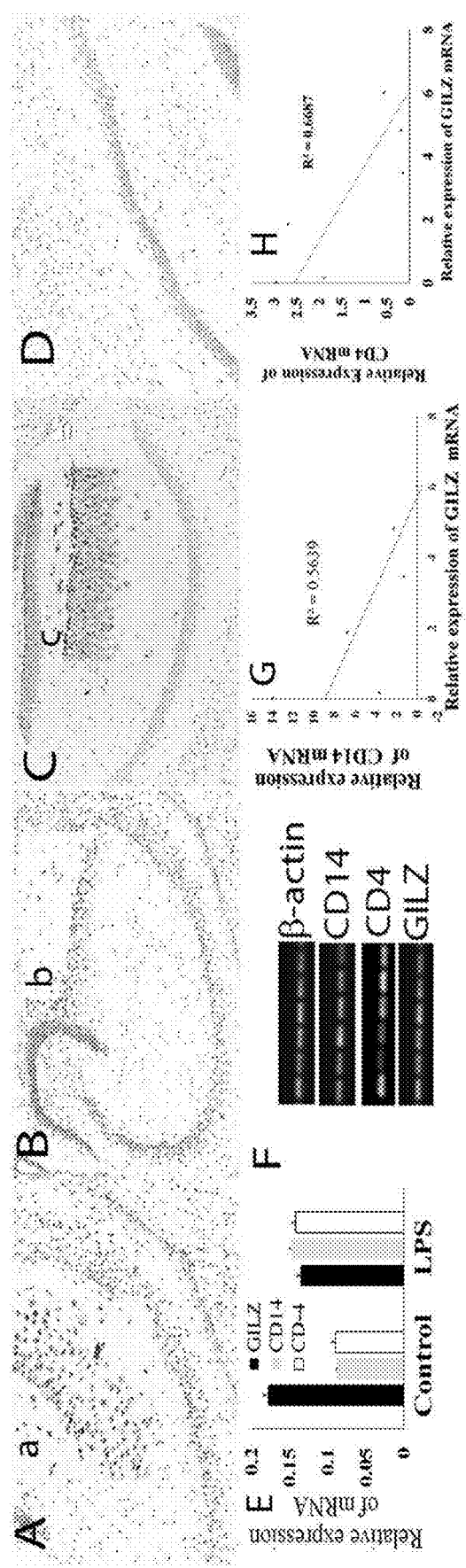
FIG. 21 A-H

FIG. 22 A-D

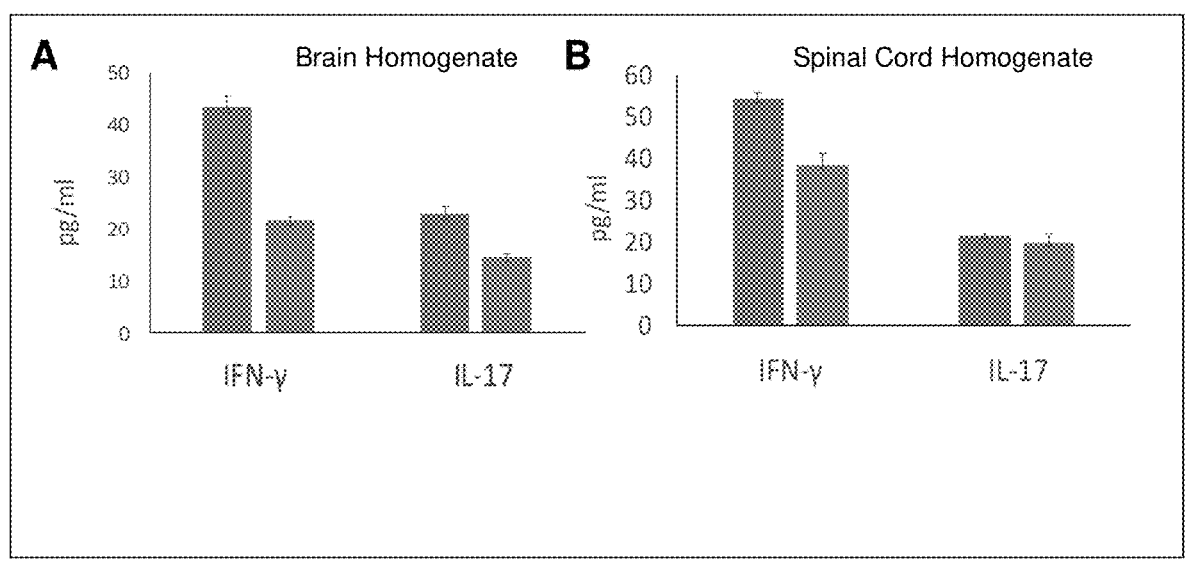
FIG. 23 A-B

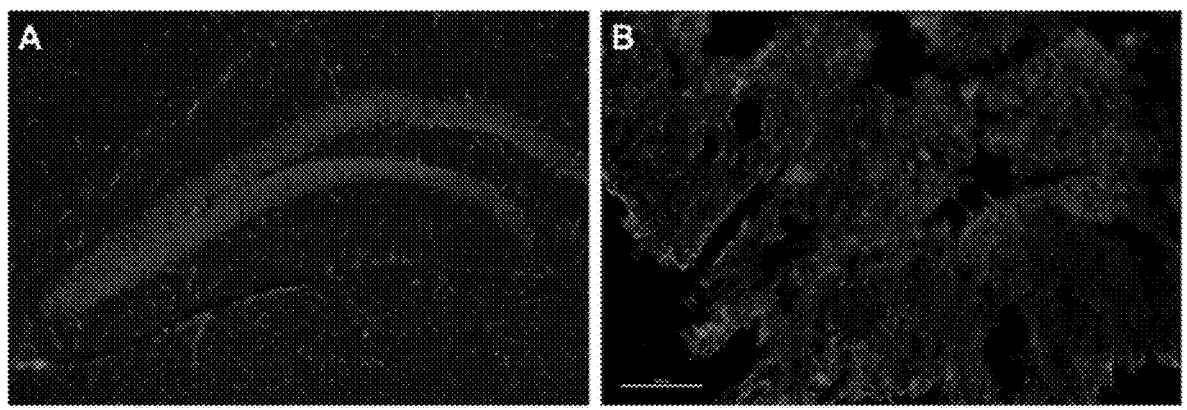
FIG. 24 A-B

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 1

Glu Pro Ala Pro Xaa Xaa Pro Xaa Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
```

```
<220> FEATURE:
<221> NAME/KEY: MOD_RES
<222> LOCATION: (8)..(9)
<223> OTHER INFORMATION: Any amino acid

<400> SEQUENCE: 2

Glu Pro Leu Pro Xaa Xaa Pro Xaa Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 3

Glu Ala Ala Pro Xaa Xaa Pro Xaa Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 4

Ala Pro Ala Pro Xaa Xaa Pro Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 5

Ala Pro Lys Pro Xaa Xaa Pro Xaa Xaa
1               5

<210> SEQ ID NO 6
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 6

Glu Pro Ala Pro Xaa Xaa Pro Xaa Xaa Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 7

Glu Pro Leu Pro Xaa Xaa Pro Xaa Xaa Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 8

Glu Ala Ala Pro Xaa Xaa Pro Xaa Xaa Xaa
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid
```

```
<400> SEQUENCE: 9

Ala Pro Ala Pro Xaa Xaa Pro Xaa Xaa Xaa
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 10

Ala Pro Lys Pro Xaa Xaa Pro Xaa Xaa Xaa
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Pro Ala Pro Arg Gln Pro Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Pro Ala Pro Arg Ala Pro Glu Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Pro Ala Pro Leu Ala Pro Tyr Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Glu Pro Ala Pro Arg Ala Pro Gly Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Pro Ala Pro Arg Ala Pro Asp Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Pro Leu Pro Glu Ala Pro Asp Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Pro Ala Pro Glu Ser Pro Gln Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Pro Ala Pro Glu Gln Pro Asp Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Pro Ala Pro Ala Ser Pro Gln Val
1               5

<210> SEQ ID NO 20
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 20

Glu Ala Ala Ala Glu Ser Pro Gln Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Pro Ala Pro Ala Ala Pro Glu Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Ala Ala Ala Glu Ala Ala Glu Thr
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Pro Ala Pro Glu Ala Pro Glu Gly Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Pro Ala Pro Tyr Gln Pro Glu Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Pro Ala Tyr Glu Ala Gln Glu Thr
1               5

```
<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Pro Ala Pro Glu Ala Gly Glu Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Pro Ala Pro Glu Ala Pro Glu Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Pro Ala Pro Tyr Gln Pro Arg Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Pro Lys Pro Tyr Gln Pro Arg Gly
1               5

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gggactttcc                                                                10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31
```

Gly Arg Lys Lys Arg Gln Arg Arg Pro Gln
1               5                   10

<210> SEQ ID NO 32
<211> LENGTH: 27
<212> TYPE: PRT
<213> ORGANISM: Artificial Sequence
<220> FEATURE:
<223> OTHER INFORMATION: Synthetic peptide

<400> SEQUENCE: 32

Thr Cys Ala Thr Gly Ala Ala Gly Thr Gly Thr Gly Ala Cys Gly Thr
1               5                   10                  15

Thr Gly Ala Cys Ala Thr Cys Cys Gly Thr Ala
            20                  25

<210> SEQ ID NO 33
<211> LENGTH: 27
<212> TYPE: PRT
<213> ORGANISM: Artificial Sequence
<220> FEATURE:
<223> OTHER INFORMATION: Synthetic peptide

<400> SEQUENCE: 33

Cys Cys Thr Ala Gly Ala Ala Gly Cys Ala Thr Thr Thr Gly Cys Gly
1               5                   10                  15

Cys Thr Gly Cys Ala Cys Gly Ala Thr Gly Gly
            20                  25

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Ala Gly Cys Thr Gly Ala Thr Gly Gly Cys Cys Thr Ala Ala Ala
1               5                   10                  15

Cys Ala Gly Ala
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Gly Gly Thr Cys Gly Gly Ala Gly Ala Thr Thr Cys Gly Thr Ala Gly
1               5                   10                  15

Cys Thr Gly Gly
            20

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

Gly Ala Gly Cys Thr Ala Gly Ala Cys Gly Ala Gly Gly Ala Ala Ala

```
Gly Thr Thr Gly Thr
            20
```

<210> SEQ ID NO 37
<211> LENGTH: 24
<212> TYPE: PRT
<213> ORGANISM: Artificial Sequence
<220> FEATURE:
<223> OTHER INFORMATION: Synthetic peptide

<400> SEQUENCE: 37

```
Ala Cys Cys Gly Thr Ala Ala Gly Cys Gly Cys Thr Thr Ala
1               5                   10                  15

Ala Gly Gly Ala Cys Ala Gly Ala
            20
```

<210> SEQ ID NO 38
<211> LENGTH: 22
<212> TYPE: PRT
<213> ORGANISM: Artificial Sequence
<220> FEATURE:
<223> OTHER INFORMATION: Synthetic peptide

<400> SEQUENCE: 38

```
Thr Gly Gly Ala Gly Thr Ala Ala Ala Cys Thr Gly Gly Gly Thr
1               5                   10                  15

Cys Gly Cys Ala Thr Cys
            20
```

<210> SEQ ID NO 39
<211> LENGTH: 22
<212> TYPE: PRT
<213> ORGANISM: Artificial Sequence
<220> FEATURE:
<223> OTHER INFORMATION: Synthetic peptide

<400> SEQUENCE: 39

```
Ala Gly Cys Cys Ala Cys Ala Gly Thr Cys Ala Thr Gly Cys Cys
1               5                   10                  15

Gly Thr Cys Ala Gly Gly
            20
```

<210> SEQ ID NO 40
<211> LENGTH: 24
<212> TYPE: PRT
<213> ORGANISM: Artificial Sequence
<220> FEATURE:
<223> OTHER INFORMATION: Synthetic peptide

<400> SEQUENCE: 40

```
Cys Thr Cys Gly Thr Cys Gly Cys Thr Ala Cys Cys Gly Thr Cys Gly
1               5                   10                  15

Thr Cys Ala Cys Thr Thr Cys Gly
            20
```

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

```
Gly Thr Gly Gly Cys Cys Cys Ala Gly Gly Thr Ala Thr Gly Ala Cys
1               5                   10                  15

Cys Cys Ala Gly
            20
```

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide

<400> SEQUENCE: 42

```
Cys Ala Thr Gly Gly Ala Gly Gly Thr Gly Gly Cys Gly Gly Thr Cys
1               5                   10                  15

Thr Ala Thr Cys
            20
```

<210> SEQ ID NO 43
<211> LENGTH: 20
<212> TYPE: DNA
<213> ORGANISM: Artificial Sequence
<220> FEATURE:
<223> OTHER INFORMATION: Synthetic peptide

<400> SEQUENCE: 43

```
cacctcctct ctcacagcgt                                           20
```

<210> SEQ ID NO 44
<211> LENGTH: 21
<212> TYPE: PRT
<213> ORGANISM: Artificial Sequence
<220> FEATURE:
<223> OTHER INFORMATION: Synthetic peptide

<400> SEQUENCE: 44

```
Ala Gly Gly Thr Cys Gly Gly Thr Gly Thr Gly Ala Ala Cys Gly Gly
1               5                   10                  15

Ala Thr Thr Thr Gly
            20
```

<210> SEQ ID NO 45
<211> LENGTH: 23
<212> TYPE: PRT
<213> ORGANISM: Artificial Sequence
<220> FEATURE:
<223> OTHER INFORMATION: Synthetic peptide

<400> SEQUENCE: 45

```
Thr Gly Thr Ala Gly Ala Cys Cys Ala Thr Gly Thr Ala Gly Thr Thr
1               5                   10                  15

Gly Ala Gly Gly Thr Cys Ala
            20
```

<210> SEQ ID NO 46
<211> LENGTH: 27
<212> TYPE: PRT
<213> ORGANISM: Artificial Sequence
<220> FEATURE:
<223> OTHER INFORMATION: Synthetic peptide

<400> SEQUENCE: 46

```
Cys Cys Thr Ala Gly Ala Ala Gly Cys Ala Thr Thr Thr Gly Cys Gly
1               5                   10                  15
```

```
Cys Thr Gly Cys Ala Cys Gly Ala Thr Gly Gly
            20                  25
```

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide

<400> SEQUENCE: 47

```
Gly Ala Thr Gly Ala Cys Ala Thr Gly Gly Thr Gly Ala Ala Gly Ala
1               5                   10                  15

Cys Gly Gly Cys
            20
```

<210> SEQ ID NO 48
<211> LENGTH: 19
<212> TYPE: PRT
<213> ORGANISM: Artificial Sequence
<220> FEATURE:
<223> OTHER INFORMATION: Synthetic peptide

<400> SEQUENCE: 48

```
Ala Gly Gly Cys Ala Cys Ala Gly Gly Thr Cys Ala Thr Cys Ala Thr
1               5                   10                  15

Cys Ala Ala
```

<210> SEQ ID NO 49
<211> LENGTH: 19
<212> TYPE: PRT
<213> ORGANISM: Artificial Sequence
<220> FEATURE:
<223> OTHER INFORMATION: Synthetic peptide

<400> SEQUENCE: 49

```
Gly Ala Gly Ala Gly Thr Cys Ala Gly Cys Gly Gly Ala Gly Thr Thr
1               5                   10                  15

Cys Thr Cys
```

<210> SEQ ID NO 50
<211> LENGTH: 22
<212> TYPE: PRT
<213> ORGANISM: Artificial Sequence
<220> FEATURE:
<223> OTHER INFORMATION: Synthetic peptide

<400> SEQUENCE: 50

```
Cys Thr Cys Ala Cys Ala Gly Gly Thr Cys Ala Ala Ala Gly Thr Ala
1               5                   10                  15

Thr Thr Gly Thr Thr Gly
            20
```

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide

<400> SEQUENCE: 51

```
Ala Ala Gly Gly Cys Thr Ala Gly Cys Thr Cys Cys Gly Cys Ala Gly
1               5                   10                  15

Gly Thr Gly Cys
```

```
<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Ala Gly Gly Thr Gly Ala Gly Cys Gly Gly Cys Ala Cys Thr Cys Gly
1               5                   10                  15

Gly Thr Cys Thr
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Gly Cys Thr Thr Thr Cys Ala Cys Cys Thr Cys Thr Gly Cys Cys Thr
1               5                   10                  15

Thr Cys Ala Cys
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Gly Ala Ala Ala Cys Thr Gly Cys Cys Ala Thr Gly Thr Thr Thr Gly
1               5                   10                  15

Ala Gly Cys Ala
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Ala Gly Thr Thr Gly Cys Cys Thr Thr Cys Thr Thr Gly Gly Gly Ala
1               5                   10                  15

Cys Thr Gly Ala
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Thr Cys Cys Ala Cys Gly Ala Thr Thr Thr Cys Cys Ala Gly Ala
1               5                   10                  15
```

```
Gly Ala Ala Cys
            20

<210> SEQ ID NO 57
<211> LENGTH: 21
<212> TYPE: PRT
<213> ORGANISM: Artificial Sequence
<220> FEATURE:
<223> OTHER INFORMATION: Synthetic peptide

<400> SEQUENCE: 57

Ala Ala Thr Gly Ala Ala Cys Cys Gly Ala Ala Gly Cys Ala Cys Ala
1               5                   10                  15

Cys Cys Ala Thr Ala
            20

<210> SEQ ID NO 58
<211> LENGTH: 21
<212> TYPE: PRT
<213> ORGANISM: Artificial Sequence
<220> FEATURE:
<223> OTHER INFORMATION: Synthetic peptide

<400> SEQUENCE: 58

Ala Thr Cys Ala Gly Ala Gly Ala Gly Thr Thr Gly Ala Cys Cys Gly
1               5                   10                  15

Cys Ala Gly Thr Thr
            20
```

PEPTIDES AND METHODS FOR TREATMENT OF NEURODEGENERATIVE DISEASES

CROSS-REFERENCE TO RELATED APPLICATIONS

This application is a continuation-in-part of PCT International Application Serial No. PCT/US2017/018645, filed on Feb. 21, 2017, and claims the benefit under 35 USC § 119(e) of U.S. Provisional Application Ser. No. 62/298,216, filed on Feb. 22, 2016, the entire disclosures of which are incorporated herein by reference

GOVERNMENT RIGHTS

This invention was made with government support under TR000006 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 13, 2018, is named 281227_ST25.txt and is 16.3 kilobytes in size.

BACKGROUND

The burden of neurodegenerative pathologies including Parkinson's and Alzheimer's disease (AD) is increasing exponentially worldwide. An accumulating body of evidence suggests that a combination of age related changes in the central nervous system (CNS) with excessive or prolonged inflammatory responses contribute to the pathophysiology of neurodegeneration, synaptic dysfunction and hippocampal behavior deficits in neurodegenerative diseases. In the United States, an estimated 5.1 million Americans currently have AD. The number is projected to increase by 40%, affecting 7.1 million individuals over 65 years of age, by 2025. Translated into healthcare costs, currently the direct cost of caring for AD is estimated at $226 billion and is projected to reach $1.1 trillion by 2050. Thus, there is an urgent need to grow the therapeutic pipeline for AD with agents capable of slowing the disease progression.

The pleiotropic transcription factor, nuclear factor-kappa B (NF-κβ) is induced by many physiological and pathological stimuli in the CNS. The NF-κβ family consists of five members, p50, c-rel, p65, RelB and p52 that can diversely combine to form transcriptionally active dimers. It has been suggested that the nature of the dimers determine the effects of activated NF-κβ. While c-rel containing dimers preferentially promote transactivation of anti-apoptotic factors, activation of p65/p50 dimers primarily enhance inflammatory and pro-apoptotic gene transcription. Positive and negative regulatory mechanisms maintain a balance between the neuroprotective c-rel dimers and the predominantly deleterious p65:p50 dimers in healthy CNS.

In AD, secondary stimuli such as accumulating beta amyloid and oxidative stress increase activation of p65:p50 dimers in glial cells. The extracellular amyloid plaques mainly include the 42-residue long Aβ amyloid b-peptide (Aβ), obtained by proteolytic cleavage from the much larger amyloid precursor protein (APP). APP is thought to play a role in cellular adhesion and motility. In the amyloidogenic pathway, APP is first cleaved by the β-secretase at the amino-terminus generating soluble sAPPβ and a carboxy-terminal fragment, which is then cleaved by γ-secretase producing the $A\beta_{1-42}$ peptides. Cleavage of APP by β-secretase (also known as beta site amyloid precursor protein cleaving enzyme-1 (BACE-1)) is considered to be the rate limiting step for Aβ generation.

The promoter region of human BACE-1 gene exhibits κB binding elements that physically interact with NF-κβ p65. Activation of NF-κβ p65 increases endogenous BACE-1 transcription and consequent Aβ production. Increased presence of activated p65 and BACE-1 has been observed around Aβ plaques in postmortem AD tissues. Extracellular Aβ peptides predominantly activate p65:p50 dimers in glia and post-mitotic neurons and enhance transactivation of inflammatory and pro-apoptotic genes. Increased presence of IL-1β, IL-6, and TNF-α have been reported in the affected tissues, serum and CSF of AD patients. Elevated Bax (proapoptotic) to Bcl-2 (anti-apoptotic) ratio have been observed in Aβ stimulated neuronal cells. A feed-back loop of excessive Aβ accumulation, NF-κβ activation, cytotoxicity and more Aβ production culminate in neurodegeneration. Conditional knock out of p65 has been shown to attenuate BACE-1 transcription and Aβ genesis in AD mice. Absence of p65 co-factors such as p300/CREB binding associated factor has been shown to mediate resistance to Aβ induced toxicity. Thus, although neuronal p65 has been shown to contribute to the physiological functions of synapse formation and transmission, considerable evidence suggest that excessive activated p65 in the CNS lead to neurodegenerative pathology. Hence selective inhibition of activated p65 could ameliorate pathologies wherein inflammation is closely associated with degeneration, such as AD.

Moreover, spinal cord injury (SCI) is a devastating affliction that affects hundreds of thousands of U.S. citizens alone with approximately 15,000 more diagnosed each year. Mechanical trauma to the spinal cord triggers a sequence of secondary pathological events including widespread cell death, axonal disruption, and inflammation ultimately leading to various severities of functional deficits. In addition, multiple reports suggest that the SCI patients frequently exhibit long-term cognitive impairments. Although very often discounted as probably reflecting concurrent brain injury, recent preclinical studies indicate that SCI induces chronic brain inflammation that culminates in neurodegeneration and cognitive decline. However, few studies have attempted to evaluate these associations at a mechanistic level and limit such deficits or promoting recovery.

Multiple mechanisms linking chronic SCI with neurodegeneration and cognitive decline have been proposed, such as potential autoimmune responses, loss of immune tolerance to amyloid beta and neuroinflammation. Stereological quantification and immunohistochemical studies have shown that the microglia in the hippocampus and cortex of mice at day 8 post-SCI exhibit an activated phenotype with elevated Iba1, chemokine-ligand 21, inflammatory cytokines and several cell cycle related genes. Increased proliferation of activated microglia has been observed even 12 weeks after SCI. It has been observed that the microglia were increased in the hippocampus at day 7 and day 14 post SCI. Furthermore, preliminary data suggest that the inflammatory cytokines are elevated in the brain homogenates harvested at day 7 post-SCI.

Although generally the blood brain barrier protects the brain against pathogens, activation of microglia can be mediated by several danger associated molecular pattern (DAMP)s or auto-antigens such as MBP and amyloid beta. High-Mobility Group Box 1 (HMGB1) is a prototypical DAMP shown to be upregulated in the spinal cord homogenates and in the circulation as early as day 3 post-SCI and persist at elevated levels for extended period even up to 2 years. HMBG1 binds two cognizant receptors, toll like receptor-4 (TLR4) and receptor for advanced glycation end (RAGE) products. Furthermore, HMBG1 has been shown to upregulate the microglial cell responses to lipopolysaccharides. Taken together, it was hypothesized that HMBG1 will initiate hippocampal microglia via TLR4 signaling with subsequent upregulation of MHC class II and the costimulatory receptors CD80 and CD86 priming the cells for antigen (auto-antigen) presentation.

The critical role of inflammation in the persistence of traumatic SCI and the significant contribution of the inflammatory response in increasing the potential risk of damage at distant intracranial sites suggest early control of inflammation could not only enhance tissue repair at the site of injury but also decrease the chances for extended CNS damage. NF-κβ is a major regulator of inflammatory responses. Aberrant activation of NF-κβ p65 has been observed in both glial cells and neurons in SCI, which in turn leads to increased transactivation of proinflammatory cytokines and pro-apoptotic factors. Therefore, targeting NF-κβ has been recognized as an effective therapeutic strategy for SCI13. The profound therapeutic efficacy of glucocorticoids (GC), widely prescribed as a first line therapy for SCI is largely attributed to the inhibition of NF-κβ by GC receptor in the nucleus. However, binding of GC receptor to specific negative response DNA elements induces cis-repression of osteocalcin and other target genes that precipitate many side-effects of GC including osteoporosis, diabetes and obesity. Strategies that duplicate the beneficial effects of GC and inhibit NF-κβ transactivation are likely to be of significant therapeutic advantage for SCI. As such, suppressing activated NF-κβ could be utilized to reduce tissue damage in patients post-SCI. The efficacy of glucocorticoids in acute SCI, as well as of that of many of compounds such butein, curcumin or tamoxifen evaluated in preclinical models of SCI have been attributed indirectly to NF-κβ inhibition.

Structurally, p65 has an amino terminal rel homology domain (RHD), a nuclear localization sequence (NLS) masked by the IκB inhibitory complex and a carboxy terminal transactivation domain (TAD). The transactivation activity of p65 is mediated by interactions of the TAD with co-regulators and the basal transcription machinery. Glucocorticoid induced leucine zipper (GILZ) is a p65 binding protein that sequesters activated p65 and inhibits transactivation of inflammatory and apoptotic factors. Mutational and binding analyses localized the interaction interface to the proline rich carboxy terminus of GILZ and the TAD of p65. Molecular modeling suggested that the p65 binding domain of GILZ adopts a flexible polyproline type II ($PP_{II}$) helical conformation that interacts with the highly conserved $F^{534}/F^{542}$ in p65-TAD.

In recent years, considerable success has been achieved in the development of structurally engineered peptide analogs of the binding epitope(s) of a protein as therapeutic leads. The strategy is increasingly adopted in the design of mimics of proline rich motif that mediate transient intermolecular interactions. The specificity of the interaction is determined by the nature of the proline rich binding domain interface.

Thus, there exists a need for novel pharmaceutical compositions and pharmaceutical formulations for the treatment of neurodegenerative diseases and for suppressing neuroinflammation in disease states such as SCI.

The present disclosure provides pharmaceutical compositions comprising rationally designed peptide analogs of the p65-TAD binding region of GILZ to selectively sequester activated p65. Structural and functional analyses suggest that select GILZ analog (GA) bind p65-TAD with optimum affinity, exhibit an estimated half minimal lethal dose comparable to known peptide drugs and suppress Aβ1-42 induced cytotoxicity. Furthermore, the present disclosure provides uses and methods of using the pharmaceutical compositions, and uses and methods of using pharmaceutical formulations comprising the pharmaceutical compositions, for the treatment of neurodegenerative diseases such as Alzheimer's Disease, Parkinson's Disease, multiple sclerosis, and amyotrophic lateral sclerosis (ALS). Moreover, the present disclosure provides uses and methods of using the pharmaceutical compositions, and uses and methods of using pharmaceutical formulations comprising the pharmaceutical compositions, for the treatment of a spinal cord injury, for example by reducing inflammation in the spinal cord of a patient or in the brain of a patient.

BRIEF DESCRIPTION OF THE DRAWINGS

(FIG. 4A). Phase contrast imaging of the cells shows no apparent adverse effects on morphology of cells exposed to GA-1 or GA-2 or CP-1 or CP-2 at either concentration. Exposure to CP-3 at both concentrations showed morphological changes consistent with cell death. (FIG. 4B). Cell lysates were assessed by CTG assay to determine relative levels of intracellular ATP. An increase in Relative Luminescence Units (RLU) suggesting cellular viability was observed with all treatments except CP-3.

(FIG. 8C-FIG. 8D). Representative model of p65-TAD (blue) docked with indicated PGA (red). The p65-TAD residues critical for transcriptional activity at close proximity (RMSD<5 Å) to PGA are highlighted.

(FIG. 9A) All PGA exhibit a dose dependent decrease in % bound r-p65. (FIGS. 9B-9C). Scatchard plot analysis of bound p65 against the ratio of bound p65 to free PGA-4 (representative) to determine KD. A: absorbance of PGA:p65, Ao: absorbance of r-p65-DDKanti-DDK in the absence of bound PGA, ao: total PGA concentration and io: total r-p65 concentration.

FIGS. 11A-11D show primary cultures of HFB pretreated with indicated PGA at $IC_{50}$ concentration was exposed to vehicle or 10 µM of $Aβ_{1-42}$. Cell viability at 24 hours was assessed by CTG assay. Data are presented as ΔRLT (difference in relative luminescent units) between Aβ1-42 exposed and unexposed cells) (FIG. 11A, FIG. 11B). Culture medium was assessed for IL-6 (FIG. 11C). HFB cultured similarly was harvested at the end of 4 hours (FIG. 11D). Activated p65 in nuclear extract was tested for binding an NF-κB consensus sequence. The p65 DNA binding activity was calculated as the ratio of absorbance from $Aβ_{1-42}$ stimulated cells to that of unstimulated cells. Data are mean/−S.D. $*=p<0.05$.

Figure 12:
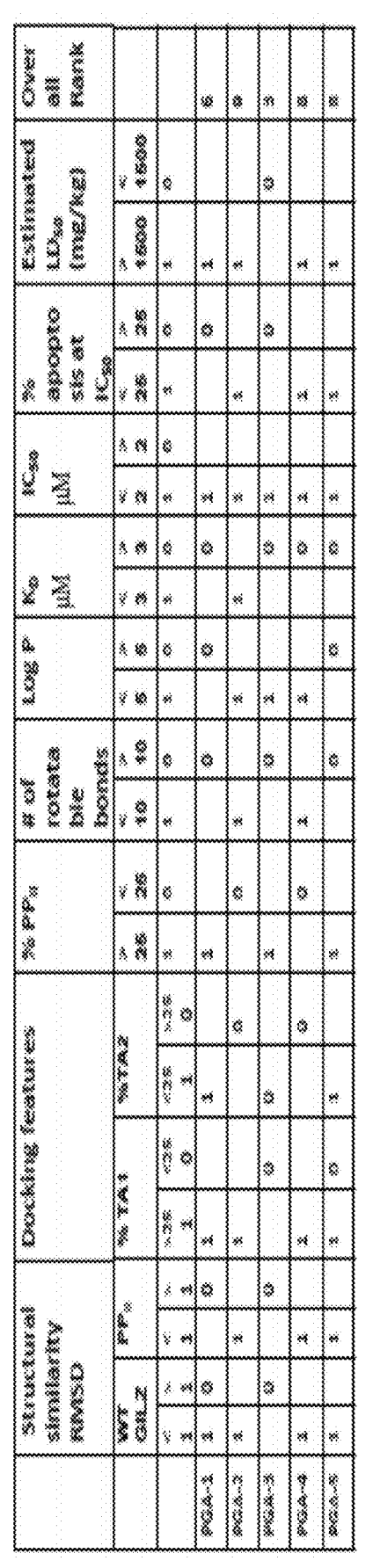

FIG. 12 shows a weighted rank order based on parameters of known peptide drugs suggested that the PGA-2 and PGA-4 exhibit significant drug like properties.

In FIGS. 13C, 13D, and 13E, cells labelled with indicated antibody and merged image. Pan-neuronal antibody, a cocktail of mAbs, identifies somatic, nuclear, dendritic and axonal proteins distributed across the pan neuronal architecture. Significant individual and co-labeling with pan-neuronal and anti-GFAP mAb suggests presence of immature neural stem cells as well as both differentiated neurons and astrocytes. Arrows and arrowheads point to cells labeled only with pan-neuronal mixture or anti-GFAP respectively.

FIGS. 14A-14D show the docked complex of GA-1 with human p65-TAD. Representative molecular model of p65-TAD docked with GA-1 (FIG. 14A) or GA-2 (FIG. 14B). The critical proline in each GA and the critical phenylalanine are highlighted in red and blue respectively. The distance between the CP atoms of the two residues in the interface is shown. C and D show Ramachandran plot of GA-1 (FIG. 14C) or GA-2 (FIG. 14D) with the phi and psi angles of the critical proline (in red) suggestive of $PP_{II}$) helical conformation.

FIGS. 15A-15H show representative images of degrees of microgliosis in mouse hippocampus. FIG. 15A-15G shows representative IHC section stained for Iba+ microglia in hippocampus of representative mouse treated with the indicated compound (FIG. 15H) shows the mean optical density of the 3,3'-diaminobenzidine (DAB)-positive cells depicting microglia in groups of vehicle or indicated compound treated mice.

FIGS. 16A-16H show representative images of degrees of astrogliosis in mouse hippocampus. FIG. 16A-16G Shows representative IHC section stained for GFAP+ microglia in hippocampus of representative mouse treated with the indicated compound (FIG. 16H) shows the mean optical density of the 3,3'-diaminobenzidine (DAB)-positive cells depicting astrocytes in groups of vehicle or indicated compound treated mice.

FIGS. 17A-17B show representative images of NF-kB p65+ microglia in mouse hippocampus. FIG. 17A shows representative IHC section stained for CD11b+ (red) and p65+ (brown) microglia. FIG. 17B shows the mean optical density of the 3,3'-diaminobenzidine (DAB)-positive cells depicting p65 microglia in groups of vehicle or indicated compound treated mice.

FIGS. 18A-18E show the effect of GILZ analogs (PGA 2 and PGA 4) treatment on cytokines in brain tissues in LPS induced neuroinflammation: Adult C57Bl/6 mice were subjected to LPS induced neuroinflammation and treated with the indicated GA or control peptides as described in materials and methods. Protein extracts of brain tissues harvested at the end of experiment was assessed for indicated pro-inflammatory cytokines (IL-1β=FIG. 18A, IL-6=FIG. 18B, TNF-α=FIG. 18C, and IFN-γ=FIG. 18D) and activated p65 NF-Kβ subunit (FIG. 18E). Values are average/ −S.D. *=p<0.05 as compared to vehicle treated mice, @=p<0.05 as compared with CP-1 or CP-2 or CP-3 treated mice.

FIGS. 19A-19E show the effects of GILZ analogs (PGA 2 and PGA 4) treatment on apoptosis related molecules in brain tissues of LPS induced neuroinflammation. Groups of adult C57Bl/6 mice were subjected to LPS induced neuroinflammation and treated with the indicated GA or control peptides as described in materials and methods. Equal quantity of cDNA isolated from brain tissues of mice treated with GA or CP were amplified for IL-1β, CD14, Bclxl and Bcl2 mRNA by quantitative PCR. The mRNA expression in each sample was finally determined after correction with GAPDH expression. FIG. 19A shows gel electrophoresis of the PCR products GAPDH (111 bp), IL-1β (89 bp), CD14 (206 bp), Bclxl (84 bp) and Bcl2 (96 bp). Relative mRNA quantitation of the indicated product with respect to that of housekeeping gene GAPDH is shown for IL-1β (FIG. 19B), CD14 (FIG. 19C), Bclxl (84 FIG. 19D) and Bcl2 (FIG. 19E). Data are average ±SD. *=p<0.05 with respect to vehicle and CP treated group.

FIGS. 20A-20D show DEX at 1 µM was not toxic but at higher (10 µM) concentration reduced the viability of SK-N-SH cells by 25% (FIG. 20A). The GILZ protein and the transcript was increased at lower but decreased at the highest DEX concentration tested (FIG. 20B-20D).

FIGS. 21A-21H show GILZ properties observed in the cortex, hippocampus and cerebellum. (FIG. 21A and FIG. 21B): Immunohistochemistry of the adult C57BL/6 mouse brain shows positive staining for GILZ in the CA1, CA3 and DG regions in hippocampus; (FIG. 21C): Reduced GILZ in hippocampus following LPS induced neuroinflammation. (a,b,c: insets show high power) (FIG. 21D): Negative control. (FIG. 21E): Relative GILZ mRNA in the brain tissues of control and LPS induced mice (N=6). (FIG. 21F): Gel electrophoresis of the PCR products. Correlation of GILZ mRNA with CD14 mRNA is shown in FIG. 21 G and with CD4 mRNA is shown in FIG. 21H.

FIGS. 22A-22D show immunohistochemical staining. Immunohistochemical staining for GILZ (FIG. 22A & FIG. 22B) and for phosphorylated p65 (FIG. 22C & FIG. 22D) of brain from 5×FAD (FIG. 22B, FIG. 22D) mice and non-transgenic liter mates (FIG. 22A, FIG. 22C). The expression of GILZ was lower and that of the p65 was higher in 5×FAD mice as compared to that in non-transgenic liter mates. Insets a,b,c and d show magnified images.

FIGS. 23A-23B show that inflammatory cytokines IFN-γ and IL-17 are elevated brain homogenates (FIG. 23A) and injured spinal cord homogenates (FIG. 23B) harvested at day 7 post-SCI (see left bars in each pair). GILZ analog was administered at 6 days post-SCI and reduced IFN-γ and IL-17 cytokine levels in brain tissue and spinal cord tissue (see right bars in each pair).

FIGS. 24A-24B show microglial response in the hippocampus (FIG. 24A) and lesion epicenter of the spinal cord (FIG. 24B) 7 days post-SCI. Microglia are labeled with Iba-1 antibody (red) and blue represents cell nuclei (10×).

Figure 1A:
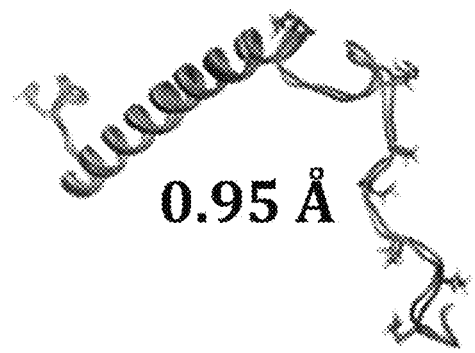
FIGS. 1A-1F show comparative modeling of GILZ analogs. Superimposition of human delta sleep inducing peptide (DSIP; PDB: 1DIP) with the predicted model of human GILZ (FIG. 1A), superimposition of indicated analog (blue) with the critical residues in the proline glutamic acid rich region of human GILZ model (red) (FIGS. 1B-1F). Structural similarity in terms of root mean square deviation (RMSD) for each superimposition is indicated.
Figure 1B:
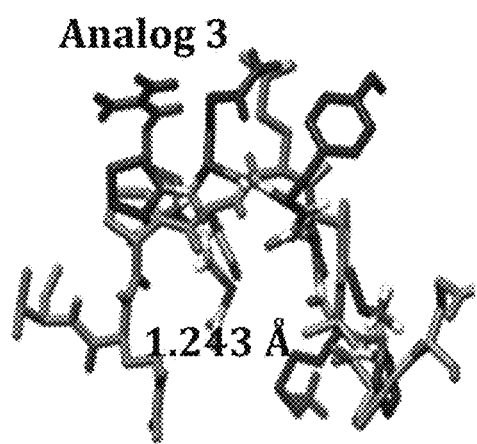
Figure 1C:
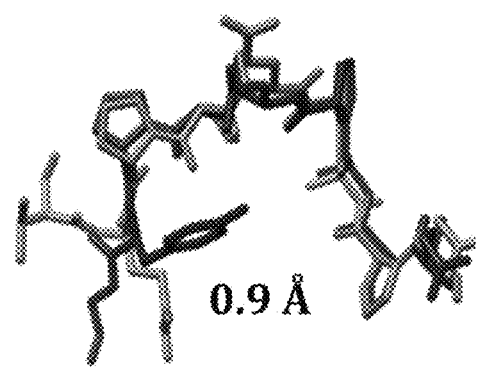
Figure 1D:
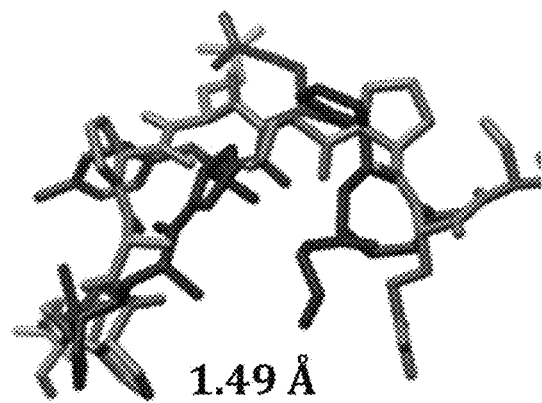
Figure 1E:
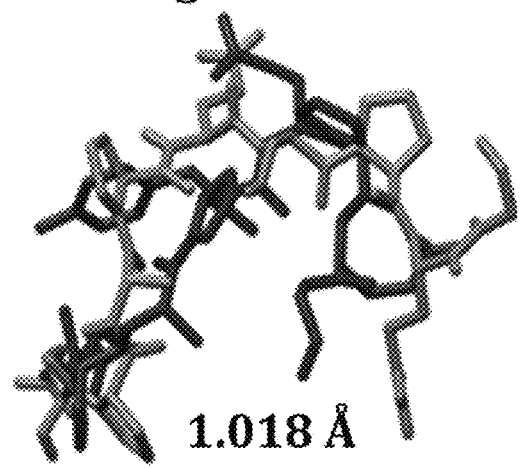
Figure 1F:
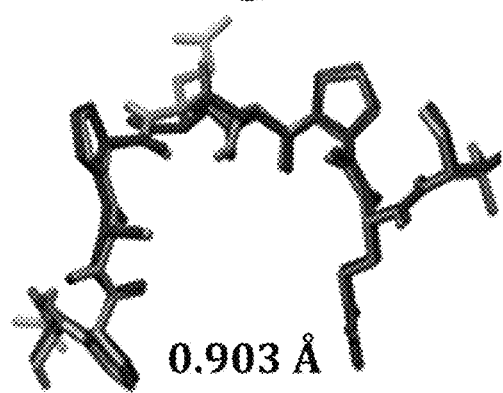

The following numbered embodiments are contemplated for the present disclosure and are non-limiting:

1. A pharmaceutical composition comprising a polypeptide from about 8 to about 12 amino acid residues, the polypeptide comprising a tetrapeptide having the sequence of PXXP, wherein
   P is proline; and
   X is any amino acid.
2. The pharmaceutical composition of clause 1, wherein the polypeptide comprises a sequence of Formula I: X1-X2-X3-P-X4-X5-P-X6-X7, wherein each of X1, X2, X3, X4, X5, X6, and X7 is independently any amino acid.
3. The pharmaceutical composition of clause 2, wherein X1 is E.
4. The pharmaceutical composition of clause 2, wherein X1 is A.
5. The pharmaceutical composition of any of clauses 2 to 4, wherein X2 is P.
6. The pharmaceutical composition of any of clauses 2 to 4, wherein X2 is A.
7. The pharmaceutical composition of any of clauses 2 to 6, wherein X3 is A.
8. The pharmaceutical composition of any of clauses 2 to 6, wherein X3 is L.
9. The pharmaceutical composition of any of clauses 2 to 6, wherein X3 is K.
10. The pharmaceutical composition of any of clauses 2 to 9, wherein X4 is selected from the group consisting of R, L, E, A, and Y.
11. The pharmaceutical composition of any of clauses 2 to 10, wherein X5 is selected from the group consisting of Q, A, and S.
12. The pharmaceutical composition of clause 1, wherein the polypeptide comprises a sequence of XXXPXXPXX.
13. The pharmaceutical composition of clause 12, wherein the polypeptide comprises a sequence of EPAPXXPXX (SEQ ID NO: 1).
14. The pharmaceutical composition of clause 12, wherein the polypeptide comprises a sequence of EPLPXXPXX (SEQ ID NO: 2).
15. The pharmaceutical composition of clause 12, wherein the polypeptide comprises a sequence of EAAPXXPXX (SEQ ID NO: 3).
16. The pharmaceutical composition of clause 12, wherein the polypeptide comprises a sequence of APAPXXPXX (SEQ ID NO: 4).
17. The pharmaceutical composition of clause 12, wherein the polypeptide comprises a sequence of APKPXXPXX (SEQ ID NO: 5).
18. The pharmaceutical composition of clause 1, wherein the polypeptide comprises a sequence of Formula II: X1-X2-X3-P-X4-X5-P-X6-X7-X8, wherein each of X1, X2, X3, X4, X5, X6, X7, and X8 is independently any amino acid.
19. The pharmaceutical composition of clause 18, wherein X1 is E.
20. The pharmaceutical composition of clause 18, wherein X1 is A.
21. The pharmaceutical composition of any one of clauses 18 to 20, wherein X2 is P.
22. The pharmaceutical composition of any one of clauses 18 to 20, wherein X2 is A.
23. The pharmaceutical composition of any one of clauses 18 to 22, wherein X3 is A.
24. The pharmaceutical composition of any one of clauses 18 to 22, wherein X3 is L.
25. The pharmaceutical composition of any one of clauses 18 to 22, wherein X3 is K.

26. The pharmaceutical composition of any one of clauses 18 to 25, wherein X4 is selected from the group consisting of R, L, E, A, and Y.

27. The pharmaceutical composition of any one of clauses 18 to 26, wherein X5 is selected from the group consisting of Q, A, and S.

28. The pharmaceutical composition of clause 1, wherein the polypeptide comprises a sequence of XXXPXXPXXX.

29. The pharmaceutical composition of clause 28, wherein the polypeptide comprises a sequence of EPAPXXPXXX (SEQ ID NO: 6).

30. The pharmaceutical composition of clause 28, wherein the polypeptide comprises a sequence of EPLPXXPXXX (SEQ ID NO: 7).

31. The pharmaceutical composition of clause 28, wherein the polypeptide comprises a sequence of EAAPXXPXXX (SEQ ID NO: 8).

32. The pharmaceutical composition of clause 28, wherein the polypeptide comprises a sequence of APAPXXPXXX (SEQ ID NO: 9).

33. The pharmaceutical composition of clause 28, wherein the polypeptide comprises a sequence of APKPXXPXXX (SEQ ID NO: 10).

34. The pharmaceutical composition of clause 1, wherein the polypeptide comprises a sequence of EPAPRQPAT (SEQ ID NO: 11).

35. The pharmaceutical composition of clause 1, wherein the polypeptide comprises a sequence of EPAPRAPEG (SEQ ID NO: 12).

36. The pharmaceutical composition of clause 1, wherein the polypeptide comprises a sequence of EPAPLAPYG (SEQ ID NO: 13).

37. The pharmaceutical composition of clause 1, wherein the polypeptide comprises a sequence of EPAPRAPGT (SEQ ID NO: 14).

38. The pharmaceutical composition of clause 1, wherein the polypeptide comprises a sequence of EPAPRAPDG (SEQ ID NO: 15).

39. The pharmaceutical composition of clause 1, wherein the polypeptide comprises a sequence of EPLPEAPDT (SEQ ID NO: 16).

40. The pharmaceutical composition of clause 1, wherein the polypeptide comprises a sequence of EPAPESPQV (SEQ ID NO: 17).

41. The pharmaceutical composition of clause 1, wherein the polypeptide comprises a sequence of EPAPEQPDG (SEQ ID NO: 18).

42. The pharmaceutical composition of clause 1, wherein the polypeptide comprises a sequence of APAPASPQV (SEQ ID NO: 19).

43. The pharmaceutical composition of clause 1, wherein the polypeptide comprises a sequence of EAAAESPQV (SEQ ID NO: 20).

44. The pharmaceutical composition of clause 1, wherein the polypeptide comprises a sequence of APAPAAPET (SEQ ID NO: 21).

45. The pharmaceutical composition of clause 1, wherein the polypeptide comprises a sequence of EAAAEAAET (SEQ ID NO: 22).

46. The pharmaceutical composition of clause 1, wherein the polypeptide comprises a sequence of EPAPEAPEGY (SEQ ID NO: 23).

47. The pharmaceutical composition of clause 1, wherein the polypeptide comprises a sequence of EPAPYQPEG (SEQ ID NO: 24).

48. The pharmaceutical composition of clause 1, wherein the polypeptide comprises a sequence of EPAYEAQET (SEQ ID NO: 25).

49. The pharmaceutical composition of clause 1, wherein the polypeptide comprises a sequence of EPAPEAGET (SEQ ID NO: 26).

50. The pharmaceutical composition of clause 1, wherein the polypeptide comprises a sequence of EPAPEAPET (SEQ ID NO: 27).

51. The pharmaceutical composition of clause 1, wherein the polypeptide comprises a sequence of EPAPESPQV (SEQ ID NO: 17).

52. The pharmaceutical composition of clause 1, wherein the polypeptide comprises a sequence of EPAPYQPRG (SEQ ID NO: 28).

53. The pharmaceutical composition of clause 1, wherein the polypeptide comprises a sequence of APKPYQPRG (SEQ ID NO: 29).

54. The pharmaceutical composition of clause 1, wherein the polypeptide consists essentially of a sequence of EPAPRQPAT (SEQ ID NO: 11).

55. The pharmaceutical composition of clause 1, wherein the polypeptide consists essentially of a sequence of EPAPRAPEG (SEQ ID NO: 12).

56. The pharmaceutical composition of clause 1, wherein the polypeptide consists essentially of a sequence of EPAPLAPYG (SEQ ID NO: 13).

57. The pharmaceutical composition of clause 1, wherein the polypeptide consists essentially of a sequence of EPAPRAPGT (SEQ ID NO: 14).

58. The pharmaceutical composition of clause 1, wherein the polypeptide consists essentially of a sequence of EPAPRAPDG (SEQ ID NO: 15).

59. The pharmaceutical composition of clause 1, wherein the polypeptide consists essentially of a sequence of EPLPEAPDT (SEQ ID NO: 16).

60. The pharmaceutical composition of clause 1, wherein the polypeptide consists essentially of a sequence of EPAPESPQV (SEQ ID NO: 17).

61. The pharmaceutical composition of clause 1, wherein the polypeptide consists essentially of a sequence of EPAPEQPDG (SEQ ID NO: 18).

62. The pharmaceutical composition of clause 1, wherein the polypeptide consists essentially of a sequence of APAPASPQV (SEQ ID NO: 19).

63. The pharmaceutical composition of clause 1, wherein the polypeptide consists essentially of a sequence of EAAAESPQV (SEQ ID NO: 20).

64. The pharmaceutical composition of clause 1, wherein the polypeptide consists essentially of a sequence of APAPAAPET (SEQ ID NO: 21).

65. The pharmaceutical composition of clause 1, wherein the polypeptide consists essentially of a sequence of EAAAEAAET (SEQ ID NO: 22).

66. The pharmaceutical composition of clause 1, wherein the polypeptide consists essentially of a sequence of EPAPEAPEGY (SEQ ID NO: 23).

67. The pharmaceutical composition of clause 1, wherein the polypeptide consists essentially of a sequence of EPAPYQPEG (SEQ ID NO: 24).

68. The pharmaceutical composition of clause 1, wherein the polypeptide consists essentially of a sequence of EPAYEAQET (SEQ ID NO: 25).

69. The pharmaceutical composition of clause 1, wherein the polypeptide consists essentially of a sequence of EPAPEAGET (SEQ ID NO: 26).

70. The pharmaceutical composition of clause 1, wherein the polypeptide consists essentially of a sequence of EPAPEAPET (SEQ ID NO: 27).

71. The pharmaceutical composition of clause 1, wherein the polypeptide consists essentially of a sequence of EPAPESPQV (SEQ ID NO: 17).

72. The pharmaceutical composition of clause 1, wherein the polypeptide consists essentially of a sequence of EPAPYQPRG (SEQ ID NO: 28).

73. The pharmaceutical composition of clause 1, wherein the polypeptide consists essentially of a sequence of APKPYQPRG (SEQ ID NO: 29).

74. The pharmaceutical composition of clause 1, wherein the polypeptide consists of a sequence of EPAPRQPAT (SEQ ID NO: 11).

75. The pharmaceutical composition of clause 1, wherein the polypeptide consists of a sequence of EPAPRAPEG (SEQ ID NO: 12).

76. The pharmaceutical composition of clause 1, wherein the polypeptide consists of a sequence of EPAPLAPYG (SEQ ID NO: 13).

77. The pharmaceutical composition of clause 1, wherein the polypeptide consists of a sequence of EPAPRAPGT (SEQ ID NO: 14).

78. The pharmaceutical composition of clause 1, wherein the polypeptide consists of a sequence of EPAPRAPDG (SEQ ID NO: 15).

79. The pharmaceutical composition of clause 1, wherein the polypeptide consists of a sequence of EPLPEAPDT (SEQ ID NO: 16).

80. The pharmaceutical composition of clause 1, wherein the polypeptide consists of a sequence of EPAPESPQV (SEQ ID NO: 17).

81. The pharmaceutical composition of clause 1, wherein the polypeptide consists of a sequence of EPAPEQPDG (SEQ ID NO: 18).

82. The pharmaceutical composition of clause 1, wherein the polypeptide consists of a sequence of APAPASPQV (SEQ ID NO: 19).

83. The pharmaceutical composition of clause 1, wherein the polypeptide consists of a sequence of EAAAESPQV (SEQ ID NO: 20).

84. The pharmaceutical composition of clause 1, wherein the polypeptide consists of a sequence of APAPAAPET (SEQ ID NO: 21).

85. The pharmaceutical composition of clause 1, wherein the polypeptide consists of a sequence of EAAAEAAET (SEQ ID NO: 22).

86. The pharmaceutical composition of clause 1, wherein the polypeptide consists of a sequence of EPAPEAPEGY (SEQ ID NO: 23).

87. The pharmaceutical composition of clause 1, wherein the polypeptide consists of a sequence of EPAPYQPEG (SEQ ID NO: 24).

88. The pharmaceutical composition of clause 1, wherein the polypeptide consists of a sequence of EPAYEAQET (SEQ ID NO: 25).

89. The pharmaceutical composition of clause 1, wherein the polypeptide consists of a sequence of EPAPEAGET (SEQ ID NO: 26).

90. The pharmaceutical composition of clause 1, wherein the polypeptide consists of a sequence of EPAPEAPET (SEQ ID NO: 27).

91. The pharmaceutical composition of clause 1, wherein the polypeptide consists of a sequence of EPAPESPQV (SEQ ID NO: 17).

92. The pharmaceutical composition of clause 1, wherein the polypeptide consists of a sequence of EPAPYQPRG (SEQ ID NO: 28).

93. The pharmaceutical composition of clause 1, wherein the polypeptide consists of a sequence of APKPYQPRG (SEQ ID NO: 29).

94. The pharmaceutical composition of any one of clauses 1 to 93, wherein the composition suppresses p65 binding.

95. The pharmaceutical composition of any one of clauses 1 to 93, wherein the composition suppresses p65 activation.

96. The pharmaceutical composition of any one of clauses 1 to 93, wherein the composition inhibits NF-κB translocation to the nucleus of a cell.

97. A pharmaceutical formulation comprising the pharmaceutical composition of any one of clauses 1 to 96.

98. The pharmaceutical formulation of clause 97 further comprising a pharmaceutically acceptable carrier.

99. The pharmaceutical formulation of clause 97 or clause 98 optionally including one or more other therapeutic ingredients.

100. The pharmaceutical formulation of any one of clauses 97 to 99 wherein the formulation is a single unit dose.

101. A lyophilisate or powder of the pharmaceutical formulation of any one of clauses 97 to 100.

102. An aqueous solution produced by dissolving the lyophilisate or powder of clause 101 in water.

103. Use of the pharmaceutical composition or the pharmaceutical formulation of any one of clauses 1-100 for the treatment of a neurodegenerative disease in a patient.

104. The use of clause 103 wherein the neurodegenerative disease is Alzheimer's Disease.

105. The use of clause 103 wherein the neurodegenerative disease is Parkinson's Disease.

106. The use of clause 103 wherein the neurodegenerative disease is multiple sclerosis.

107. The use of clause 103 wherein the neurodegenerative disease is amyotrophic lateral sclerosis (ALS).

108. A method of treating a neurodegenerative disease in a patient, said method comprising the step of administering the pharmaceutical composition or the pharmaceutical formulation of any one of clauses 1-100 to the patient in need thereof.

109. The method of clause 108 wherein the neurodegenerative disease is Alzheimer's Disease.

110. The method of clause 108 wherein the neurodegenerative disease is Parkinson's Disease.

111. The method of clause 108 wherein the neurodegenerative disease is multiple sclerosis.

112. The method of clause 108 wherein the neurodegenerative disease is amyotrophic lateral sclerosis (ALS).

113. Use of the pharmaceutical composition or the pharmaceutical formulation of any one of clauses 1-100 for the treatment of a spinal cord injury in a patient.

114. The use of clause 113, wherein the administration of the pharmaceutical composition reduces inflammation in the spinal cord of the patient.

115. The use of clause 113, wherein the administration of the pharmaceutical composition reduces inflammation in the brain of the patient.

116. The use of clause 113, wherein the administration of the pharmaceutical composition reduces the presence of one or more cytokines in the spinal cord of the patient or in the brain of the patient.

117. The use of clause 116, wherein the cytokine is IFN-γ.

118. The use of clause 116, wherein the cytokine is IL-17.

119. A method of treating a spinal cord injury in a patient, said method comprising the step of administering the pharmaceutical composition or the pharmaceutical formulation of any one of clauses 1-100 to the patient in need thereof.

120. The method of clause 119, wherein the administration of the pharmaceutical composition reduces inflammation in the spinal cord of the patient.

121. The method of clause 119, wherein the administration of the pharmaceutical composition reduces inflammation in the brain of the patient.

122. The method of clause 119, wherein the administration of the pharmaceutical composition reduces the presence of one or more cytokines in the spinal cord of the patient or in the brain of the patient.

123. The method of clause 122, wherein the cytokine is IFN-γ.

124. The method of clause 122, wherein the cytokine is IL-17.

In particular, the following analogs were developed and evaluated:

| Analog | Sequence | SEQ ID NO: | Name |
|---|---|---|---|
| Analog 1 | EPAPRQPAT | 11 | |
| Analog 2 | EPAPRAPEG | 12 | |
| Analog 3 (GA-2) | EPAPLAPYG | 13 | PGA-2 |
| Analog 4 | EPAPRAPGT | 14 | |
| Analog 5 | EPAPRAPDG | 15 | |
| Analog 6 | EPLPEAPDT | 16 | |
| Analog 7 (GA-4) | EPAPESPQV | 17 | PGA-4 |
| Analog 8 (GA-5) | EPAPEQPDG | 18 | PGA-5 |
| Analog 9 | APAPASPQV | 19 | |
| Analog 10 | EAAAESPQV | 20 | |
| Analog 11 | APAPAAPET | 21 | |
| Analog 12 | EAAAEAAET | 22 | |
| Analog 13 | EPAPEAPEGY | 23 | |
| Analog 14 (GA-3) | EPAPYQPEG | 24 | PGA-3 |
| Analog 15 | EPAYEAQET | 25 | |
| Analog 16 | EPAPEAGET | 26 | |
| Analog 17 | EPAPEAPET | 27 | |
| Analog 18 | EPAPESPQV | 17 | |
| Analog 19 | EPAPYQPRG | 28 | |
| Analog 20 (GA-1) | APKPYQPRG | 29 | PGA-1 |

Furthermore, the following analogs were tested:

| Name | Sequence | SEQ ID NO: |
|---|---|---|
| PGA-1 | APKPYQPRG | 29 |
| PGA-2 | EPAPLAPYG | 13 |
| PGA-3 | EPAPYQPEG | 24 |
| PGA-4 | EPAPESPQV | 17 |
| PGA-5 | EPAPEQPDG | 18 |

Increased NF-κB p65 secondary to aging and environmental stimuli contribute significantly to the inflammation and degeneration in AD. Synthetic compounds including terpenoids like adenanthin and resveratrol or other sirtuin activators interact with NF-κB p65, suppress inflammation and cytotoxicity in AD models. As opposed to high throughput screening, computational design of interface peptide mimics followed by functional evaluation represents an efficient method in the drug design and discovery process. Here we report the design and physicochemical characteristics of peptide analogs of the GILZ:p65 interface, show that select analogs bind p65-TAD and suppress Aβ induced toxicity in human fetal brain cells exhibiting potential therapeutic value for AD.

In human interactome, preponderant transient intermolecular interactions are mediated by proline rich epitope of one protein binding the aromatic residue rich flat interface of the second protein. Often the proline rich epitope adopts an extended $PP_{II}$ helical conformation that behaves as an adaptable glove in obtaining the correct binding orientation. Here it is pertinent to note that the template based modeling suggested that the p65 binding domain of GILZ exhibits a $PP_{II}$ helical conformation and that the p65-TAD is unstructured or flat. Mutational analyses identified $^{120}$PEA(S)P$^{124}$ of GILZ as hot spot residues for interacting with NF-κB p65. In the GILZ:p65-TAD complex, the critical proline of GILZ, $^{120}$P exhibits φ and ψ angles of −67°±5° of 142.5°±15° respectively and is in close proximity with the conserved phenylalanines ($^{534}$F, $^{542}$F) of p65-TAD. Collectively, these observations suggest that the GILZ:p65-TAD complex represents a druggable target for development of specific therapeutic leads.

Incorporating rational substitutions in the polyproline motif of GILZ in the context of the p65-TAD interface we designed multiple peptide analogs of GILZ or GA. Molecular superposition is one of the most important means to interpret the relations between three-dimensional structures. The low RMSD upon superimposition with experimental $PP_{II}$ and wild type GILZ suggests that the select GA represent true structural mimic of the p65 binding domain of GILZ. Significantly docking analyses showed that the top ranked GA exhibited >20% contact with the functionally critical p65-TAD residues ($F^{534}$, $F^{542}$) in >90% of docked solutions.

An important advantage of proline-rich motif at interface of transient intermolecular interactions is the weak binding kinetics without compromising affinity. Furthermore, it allows for introduction of small changes in the sequence of the motif or its binding domain to mediate large changes in the affinity of the interaction. We observed that the GA-1 and GA-2 evaluated by functional analysis exhibited greater affinity for binding r-p65 than the full length r-GILZ. Previously, proline rich peptides that bind Src homology 3 binding domain or the transcription factor human estrogen receptor alpha or the cell surface CD80 ligand have been shown to exhibit dissociation constant ($K_D$) in the micromolar range and inhibit protein:protein interactions.

Many peptide drugs including copaxone, leuprolide acetate/goserelin (peptide antagonists of GnRH receptor), octreotide (a cyclic octapeptide mimicking natural hormone somatostatin) and glucagon like peptide-1 (GLP-1) analog have been evaluated in models of AD substantiating the credibility of peptide drugs for AD. Proline rich $PP_{II}$ helical peptides such as apidaecin, oncocin and drosocin have shown to exhibit significant influx into CNS and distribution within the brain parenchyma. Hence PGA is likely to cross the blood brain barrier and reach optimal concentration in the brain to be clinically efficient. Significantly, the estimated LD50 for GA-1 and GA-2 as determined by the method of Speilmann et al. is within the range of these peptide drugs. Furthermore the ability of GA-1 and GA-2 to suppress Aβ induced inflammatory and cytotoxic responses in human fetal brain cells suggests potential as AD therapeutic agents.

Figure 7:
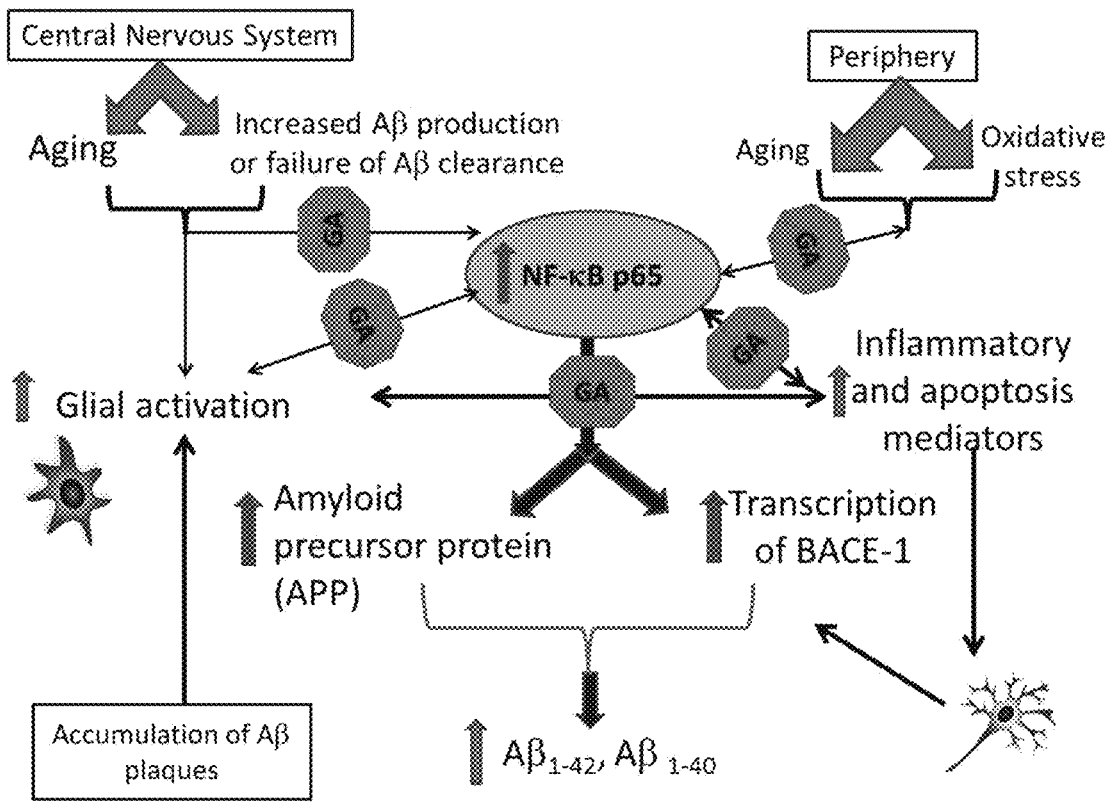
FIG. 7 shows the Schematic representation of pathological mechanisms of AD and points of intervention by GA. Increased oxidative stress and other age related changes upregulate NF-κB p65 which in turn increase transcription of amyloid precursor protein (APP) and/or beta site amyloid precursor protein cleaving enzyme-1 (BACE-1) leading to generation and accumulation of Aβ peptides in the CNS parenchyma. Glial cells exposed to Aβ peptides exhibit increased p65 activation and secrete inflammatory and apoptosis mediators. Affected neurons upregulate Aβ peptides and the vicious cycle of Aβ deposition, inflammation and neuronal apoptosis leads to AD. GILZ analogs (GA) by virtue of binding activated NF-κB p65 blocks Aβ generation and suppressing inflammation, thereby ameliorating AD pathology.
Figure 8A:
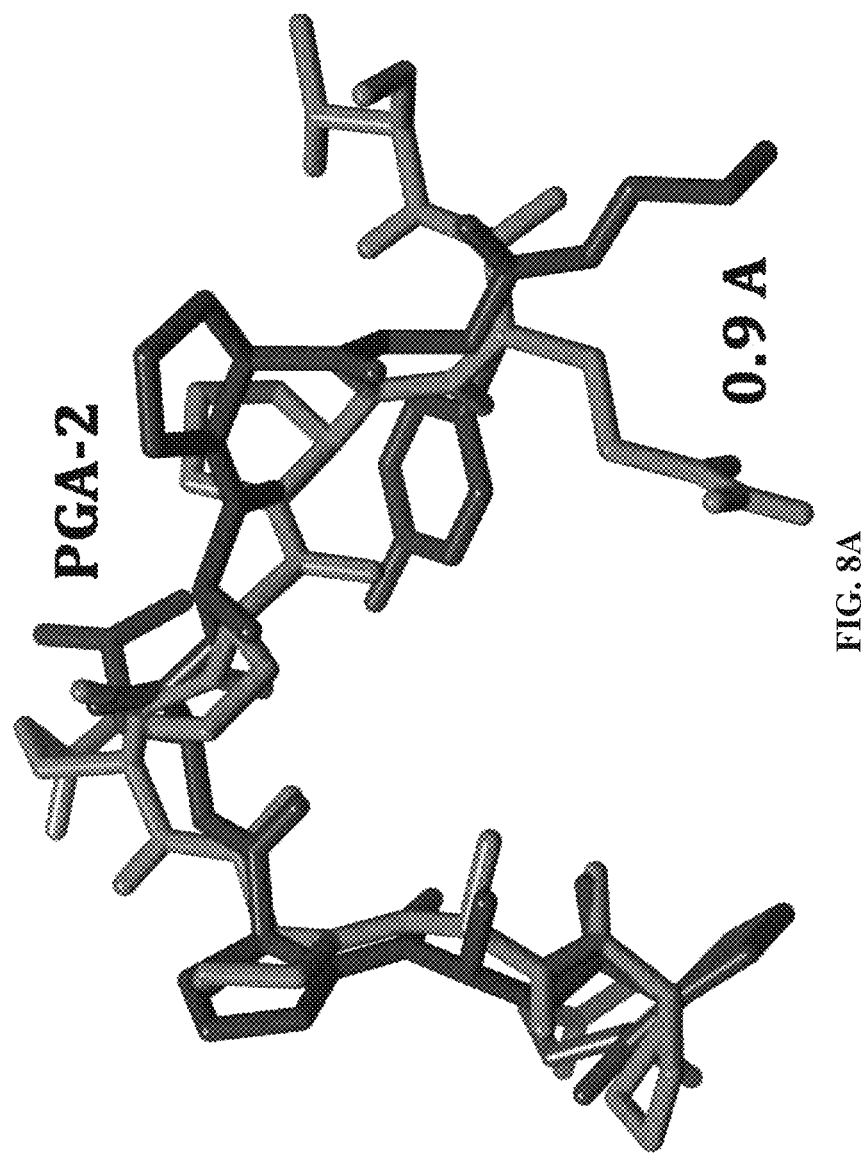
FIGS. 8A-8D show comparative modeling and docking of PGA:p65 (FIG. 8A-FIG. 8B). Superimposition of indicated PGA (blue) with the critical proline rich region of human GILZ (red), both built using PDB:1DIP as template. Root mean square deviation (RMSD) representing structural similarity is given.
Figure 8B:
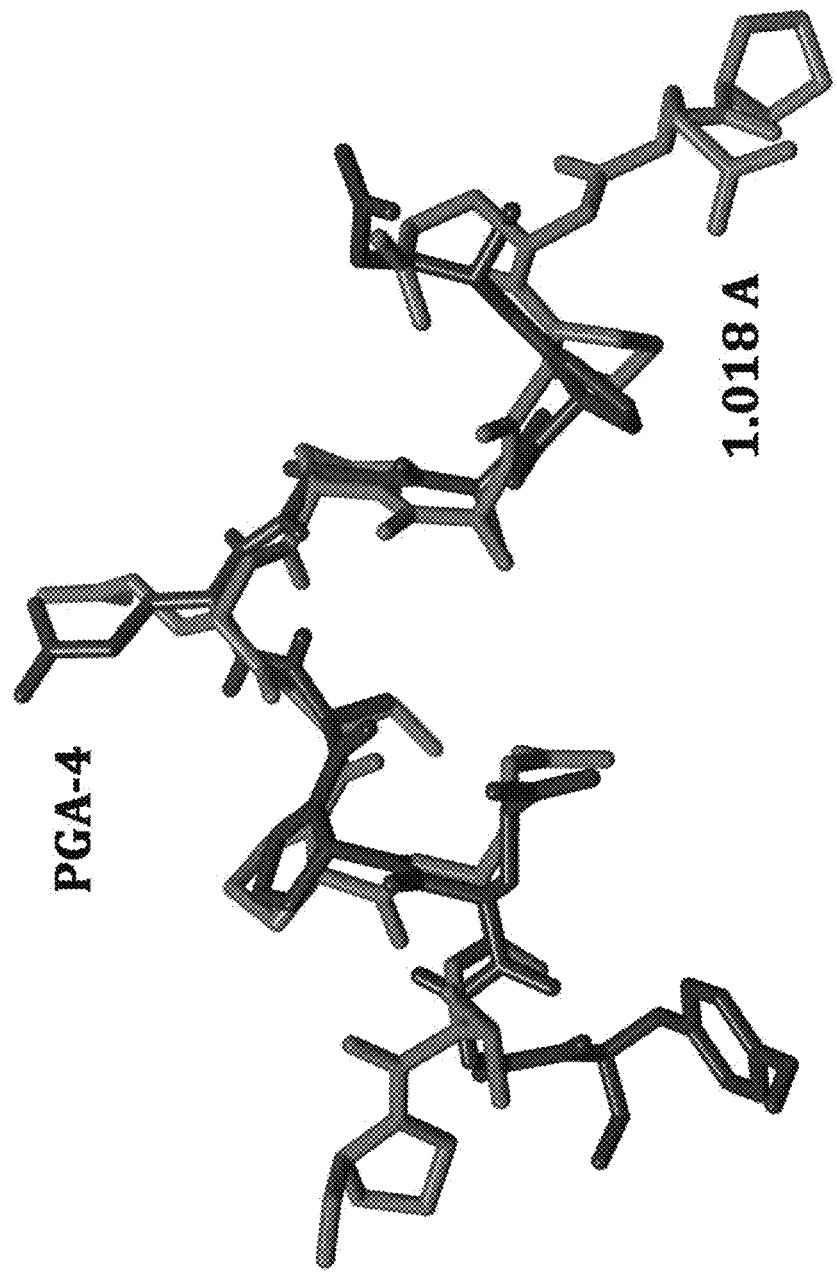
Figure 8C:
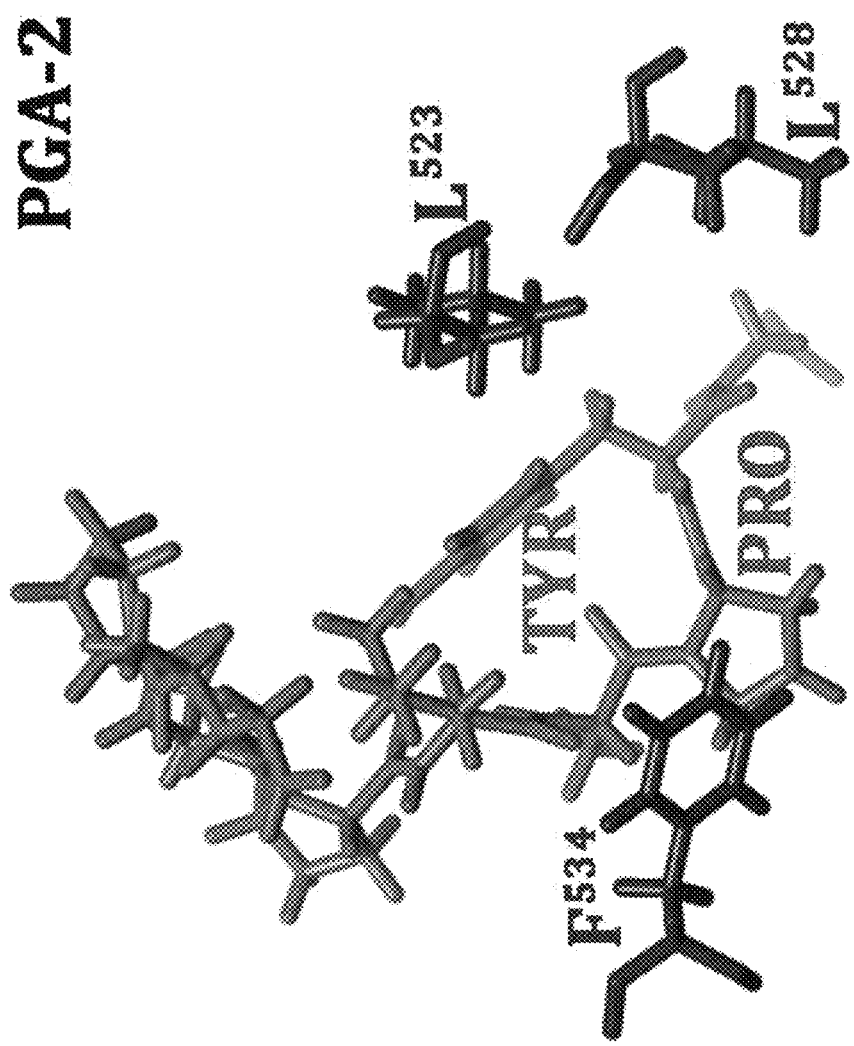
Figure 8D:
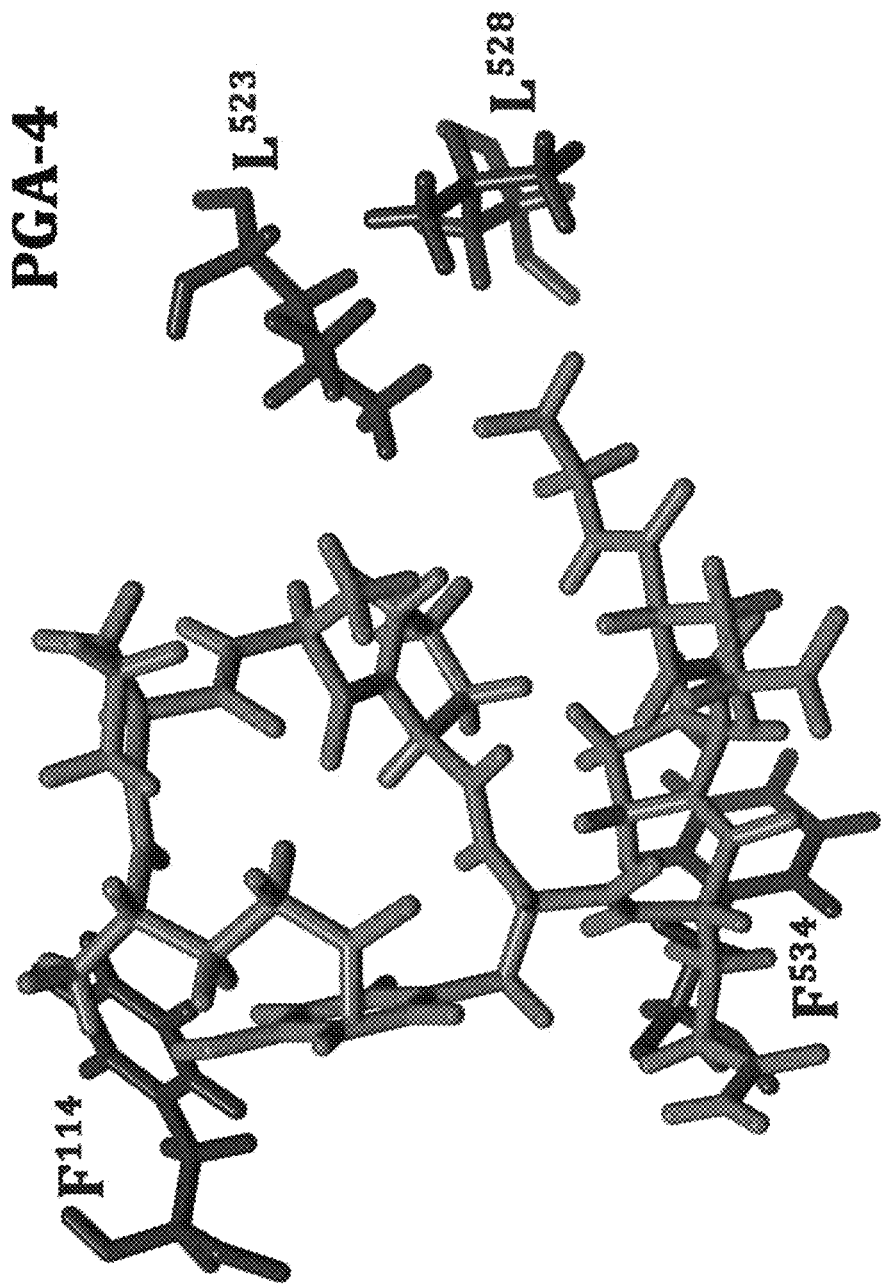

The goal of biological therapies is to restore healthy balance by targeting specific molecules that are critical for mediating or perpetuating imbalanced cellular responses. In recent years peptide-based drugs have gained considerable value in the discovery phase of drug development, in particular in the design of interface mimotopes. The functionally active peptides are amenable to further modifications into peptidomimetic compounds or small molecules with improved pharmacokinetic properties. In this context, the low molecular weight GA-1 and GA-2 can act as lead compounds in the development of specific small molecule inhibitors of NF-κβ p65 with significant therapeutic potential for chronic neurodegenerative diseases including AD (see FIG. 7).

In some embodiments, the pharmaceutical formulations described herein further comprise a pharmaceutically acceptable carrier. In some embodiments, the pharmaceutical formulations described herein further comprise a pharmaceutically acceptable diluent. Diluent or carrier ingredients used in the pharmaceutical compositions containing polypeptides can be selected so that they do not diminish the desired effects of the polypeptide. Examples of suitable dosage forms include aqueous solutions of the polypeptides, for example, a solution in isotonic saline, 5% glucose or other well-known pharmaceutically acceptable liquid carriers such as alcohols, glycols, esters and amides.

As used herein, "carrier" refers to any ingredient other than the active component(s) in a formulation. Pharmaceutically acceptable carriers are determined in part by the particular composition being administered, as well as by the particular method used to administer the composition (see, e.g., Remington's Pharmaceutical Sciences, 17th ed. (1985)). The choice of carrier will to a large extent depend on factors such as the particular mode of administration, the effect of the carrier on solubility and stability, and the nature of the dosage form. In one illustrative aspect, the carrier is a liquid carrier.

As used herein, the term "pharmaceutically acceptable" includes "veterinarily acceptable", and thus includes both human and animal applications independently. For example, a "patient" as referred to herein can be a human patient or a veterinary patient, such as a domesticated animal (e.g., a pet).

In some embodiments, the pharmaceutical formulations described herein optionally include one or more other therapeutic ingredients. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with the described polypeptides and may be either administered separately or in the same pharmaceutical formulation. The amount of other active ingredients to be given may be readily determined by one skilled in the art based upon therapy with described polypeptides.

In some embodiments, the pharmaceutical formulations described herein are a single unit dose. As used herein, the term "unit dose" is a discrete amount of the composition comprising a predetermined amount of the described polypeptides. The amount of the described polypeptides is generally equal to the dosage of the described polypeptides which would be administered to an animal or a convenient fraction of such a dosage such as, for example, one-half or one-third of such a dosage.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The aqueous preparations according to the invention can be used to produce lyophilisates by conventional lyophilization or powders. The preparations according to the invention are obtained again by dissolving the lyophilisates in water or other aqueous solutions. The term "lyophilization," also known as freeze-drying, is a commonly employed technique for presenting proteins which serves to remove water from the protein preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. For example, see Pikal, M. Biopharm. 3(9)26-30 (1990) and Arakawa et al., Pharm. Res., 8(3):285-291 (1991).

In one embodiment, the solubility of the polypeptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a polypeptide may be formulated as a solid, semi-solid, or thixotropic liquid for administration as an implanted depot providing modified release of the active compound.

The formulations can be presented in unit-dose or multi-dose sealed containers, such as ampules and vials. The formulations can also be presented in syringes, such as prefilled syringes.

In various embodiments, the dosages of the polypeptides can vary significantly depending on the patient condition and the severity of the disease to be treated. The effective amount to be administered to a patient is based on body surface area, patient weight or mass, and physician assessment of patient condition.

Suitable dosages of the polypeptides can be determined by standard methods, for example by establishing dose-response curves in laboratory animal models or in humans in clinical trials. Illustratively, suitable dosages of polypeptides (administered in a single bolus or over time) include from about 1 pg/kg to about 10 µg/kg, from about 1 pg/kg to about 1 µg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 µg/kg, from about 1 ng/kg to about 500 ng/kg, from about 100 ng/kg to about 500 µg/kg, from about 100 ng/kg to about 100 µg/kg, from about 1 µg/kg to about 500 µg/kg, or from about 1 µg/kg to about 100 µg/kg. In each of these embodiments, dose/kg refers to the dose per kilogram of a patient's or animal's mass or body weight.

The present disclosure provides uses and methods of using the pharmaceutical compositions, and uses and methods of using pharmaceutical formulations comprising the pharmaceutical compositions, for the treatment of neurodegenerative diseases such as Alzheimer's Disease, Parkinson's Disease, multiple sclerosis, and amyotrophic lateral sclerosis (ALS).

The present disclosure also provides uses and methods of using the pharmaceutical compositions, and uses and methods of using pharmaceutical formulations comprising the pharmaceutical compositions, for treating a spinal cord injury in a patient. In some embodiments, the administration of the pharmaceutical composition reduces inflammation in the spinal cord of the patient. In some embodiments, administration of the pharmaceutical composition reduces inflammation in the brain of the patient. In various embodiments, administration of the pharmaceutical composition reduces the presence of one or more cytokines in the spinal cord of the patient or in the brain of the patient. In certain embodiments, the cytokine is IFN-γ. In other embodiments, the cytokine is IL-17.

EXAMPLES

Example 1

Peptides and reagents: All GILZ peptides were synthesized as peptide amides with amino-terminal acetylation (Genescript, Piscataway, N.J.) at 95% purity as confirmed by mass spectrometry. To facilitate intracellular delivery the GA were either co-synthesized with the cell penetrating agent, TAT (transactivator of transcription) peptide or used as covalent mixture with Pep-1 chariot peptide (Anaspec, Fremont, Calif.). Recombinant human p65 protein (r-p65) with DDK tag (catalog number TP320780), purified recombinant human GILZ protein (r-GILZ) with GST tag and biotinylated anti-DDK antibody were from Ori-Gene Technologies Inc., Rockville, Md. Purified $A\beta_{1-42}$ peptide was purchased from American Peptide company (American peptide company, Sunnyvale, Calif.: Product #62-0-80 Lot #1310160T). $A\beta_{1-42}$ peptide stock (1 mg/mL) was prepared in cell culture medium and incubated at 37° C. for 24 hours prior to use in cell cultures.

Comparative modeling: Models of human GILZ and its mimics were built by the CPH models and Geno3D servers using delta sleep inducing peptide (DSIP-PDB:1DIP) as template based on >90% sequence similarity. While the Geno3D system builds models based on topology mapping, the CPH system uses profile-based alignment as seed for developing energy-minimized homology model. The secondary structure assignment of the GILZ models was independently assessed by the PROSS (Protein dihedral angle-based Secondary Structure assignment) program. Superimposition of the model of each GILZ mimic with experimentally determined $PP_{II}$ helix and wild type GILZ determined the similarity between the structures in terms of root mean square deviation (RMSD). Homology models of p65-TAD was developed similarly using elongation factor eEF3 (PDB:3H7H) as template with which it shares 42% sequence similarity.

Design and modeling of GILZ mimic: Strategies to determine the smallest biologically active fragment of a lead peptide involves truncation, deletion, alanine scanning and substitution of residues. Deletion studies suggested that the amino terminal helix of GILZ is critical for dimerization but is not involved in the interaction with NF-κβ. Truncation mutants suggested that the residues spanning of the GILZ were critical for GILZ mediated inhibition of NF-κβ transactivation. Molecular modeling showed that the GILZ-COOH or a 22 residue peptide derived from the proline rich region adopted an extended $PP_{II}$ helical conformation and interacted with the p65-TAD exhibiting weak binding kinetics. Alanine scanning mutagenesis suggested that the substitution of the $^{120}PXXP^{123}$ motif abrogated the ability to inhibit NF-κβ transactivation potentially due to loss of $PP_{II}$ conformation. In human and mouse GILZ, hydrogen bonding between the side chain of Ser or Thr and the backbone carbonyl of Glu or Pro respectively could contribute to the stability of $PP_{II}$ conformation. We designed 40 GILZ mimics by incorporating rational substitutions in the p65 binding motif of GILZ with residues that increase the propensity for $PP_{II}$ helical conformation and stabilize it. Comparative modeling with substituted residues for all 40 GA was performed to obtain structural representation of each with reference to the adjacent residues of human GILZ. In addition we introduced conformational constraints by superimposing each GILZ mimic model on structures with solved or experimental $PP_{II}$ helix and wild type human GILZ to select for mimics with significant structural homology (see FIGS. 1A-1F). The $PP_{II}$ content of GILZ mimics as determined by PROSS ranged from 14.3%, 28.6% and 42.9%. Since $PP_{II}$ helix formation is a locally driven event with little/no involvement of long-range interactions, it is logical to presume that the synthetic GILZ mimetic peptide with blocked end groups will adopt a similar conformation as in the predicted model. Twenty GILZ mimics that exhibit near structural congruence with DSIP (<1 Å) or wild type GILZ or experimentally determined $PP_{II}$ structure (<2 Å) were selected for in silico docking.

Example 2

GILZ:p65-TAD docking: Models of human GILZ or GILZ mimic and the p65-TAD were applied as probe and target respectively in PatchDock, a geometry based algorithm that yields docked transformations scored on the basis of molecular shape complementarity and atomic desolvation energy. Top one thousand solutions were refined using FireDock (Fast Interaction Refinement in molecular docking), a program that optimizes binding of the probe by restricting side-chain flexibility to clashing interface residues. The refined docking solutions were scored based on softened van der Waals interactions, atomic contact energy, electrostatic and additional binding free energy estimations. The top ranked solutions so obtained were further screened using Chimera for interatomic distance of <5 Å between the residues of GILZ mimic and the functionally critical residues of p65-TAD. The solution with most contacts was further refined by FlexPepDock using the wild type GILZ: p65-TAD complex with greater than 50% intermolecular residue contacts as reference.

Docking of GILZ mimic and p65-TAD: To be of potential therapeutic value, the GILZ mimic should adopt $PP_{II}$ helical conformation in the context of the critical binding residues in p65-TAD. The p65-TAD is commonly divided into two distinct regions, TAD-1521-551 consisting of 36 amino acids and TAD-2428-520 with 92 residues. It has been reported that the $TAD_1$ accounts for nearly 95% of the transactivation potential of full-length p65 and that the TAD2 alone is less potent mediating about 30% activation. In particular, the highly conserved aromatic residues ($F^{534}$, $F^{542}$), acidic residues ($D^{531}$,$D^{533}$) and phosphorylation sites ($Ser^{529}$,$Ser^{536}$) in p65-TAD1 have been identified as critical for transactivation.

Homology model of p65-TAD was built using solution structure of the elongation factor eEF3 (PDB: 2XI3, 2WI3) with which it shares 42% sequence similarity. The spatial orientations of wild type GILZ and top 20 GILZ mimics with p65-TAD were assessed by multiple docking algorithms One thousand interaction possibilities identified by rigid-docking algorithm were improved by coarse refinement to restrict side-chain flexibility at the interface. The docked complexes were ranked using an optimized global energy function for higher probability prediction. Top ten solutions of each GILZ mimic were evaluated for proximity to p65-TAD residues. In general two residues are considered in contact with each other if the distance between the CP atoms is <5 Å. Interactions between the conserved $F^{534}$-$F^{542}$ in the p65-TADi and the critical prolines $P^{120}$/$P^{123}$ of GILZ could promote C—H ·· π interaction and provide substantial binding energy in the GILZ:p65-TAD complex. All solutions that exhibited an RMSD of <5 Å with the critical $F^{534}$ and $F^{542}$ were selected for further screening (Table 1).

TABLE 1

Characteristics of GILZ mimics

| | | Superimposition | | p65-Transactivation Domain | | | |
|---|---|---|---|---|---|---|---|
| | | | | | % TA2 | | |
| | | | | | CR-1 | CR-2 | CR-3 |
| | % PPII | PPII | GILZ model | % TA1 521-531 | 435-455 | 462-479 | 491-505 |
| PGA-1 | 14.3 | 0.82 | 0.216 | 19 | 43 | 39 | 20 |
| PGA-2 | 42.9 | 0.531 | 0.216 | 18 | 32 | 13 | 9 |
| PGA-3 | 14.3 | 0.109 | 0.428 | 11 | 14 | 23 | 4 |
| PGA-4 | 14.3 | 1.049 | 0.482 | 4 | 13 | 47 | 29 |
| PGA-5 | 28.6 | 1.234 | 0.586 | 11 | 14 | 23 | 4 |
| PGA-6 | 14.3 | 0.844 | 0.645 | 21 | 54 | 34 | 9 |
| PGA-7 | 14.3 | 0.156 | 0.681 | 30 | 20 | 0 | 11 |
| PGA-8 | 14.3 | 1.72 | 0.842 | 15 | 41 | 32 | 5 |
| PGA-9 | 42.9 | 0.257 | 0.88 | 24 | 42 | 29 | 13 |
| PGA-10 | 28.6 | 0.161 | 0.9 | 12 | 38 | 23 | 7 |
| PGA-11 | 28.6 | 0.703 | 0.912 | 20 | 46 | 23 | 6 |
| PGA-12 | 42.9 | 1.17 | 1 | 10 | 12 | 18 | 6 |
| PGA-13 | 14.3 | 0.58 | 1.018 | 3 | 35 | 55 | 6 |
| PGA-14 | 28.6 | 1.172 | 1.033 | 32 | 28 | 10 | 2 |
| PGA-15 | 14.3 | 0.391 | 1.047 | 12 | 36 | 8 | 7 |
| PGA-16 | 14.3 | 0.252 | 1.154 | 18 | 38 | 33 | 1 |
| PGA-17 | 28.6 | 1.293 | 1.227 | 15 | 25 | 24 | 9 |
| PGA-18 | 14.3 | 1,248 | 1.243 | 16 | 24 | 31 | 22 |
| PGA-19 | 28.6 | 0.581 | 1.49 | 7 | 22 | 24 | 7 |
| PGA-20 | 42.9 | 1.174 | 1.613 | 37 | 43 | 9 | 2 |

Table 1 shows the characteristics of twenty GILZ mimics: GILZ models (GM) with substituted residues at the proline rich region of wild type GILZ sequence were developed using Geno3D and CPHModels. Each GA model was superimposed over wild type GILZ and experimentally determined polyproline ($PP_{II}$) helical structures. The root mean square deviation (RMSD) of each superimposition as a measure of structural similarity is shown. Each GM was docked with the molecular model of p65-TAD and the docked complexes were screened for interface p65-TAD residues within 5 Å distance of GM.

Figure 2A:
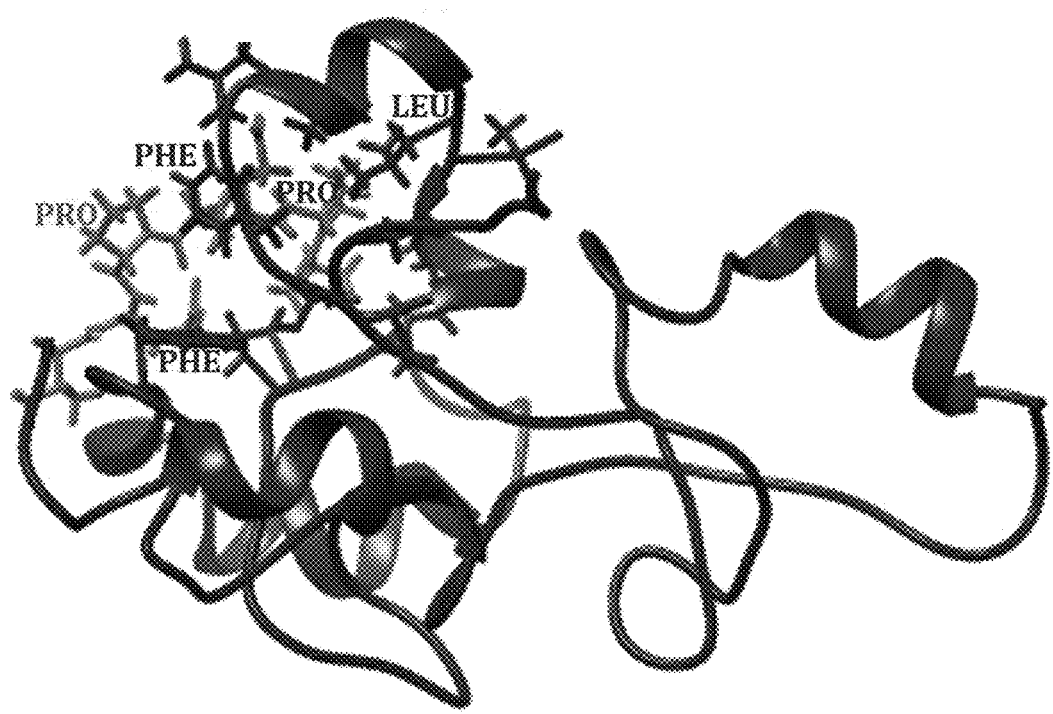
FIGS. 2A-2F show the docked complex of wild type GILZ-PER (proline glutamic acid rich region) or GILZ analog (GA) with human p65-TAD. Representative molecular model of p65-TAD docked (blue) with wild type GILZ-PER (FIG. 2A) and indicated analog (FIG. 2B-2F) (red) are shown. The residues in each analog <5 Å distance of highly conserved residues in p65-TAD2 (Phe or Phe) and the "LXXLL" motif in p65-$TAD_1$ that suggest proximity with residues critical for transcriptional activity are shown.
Figure 2B:
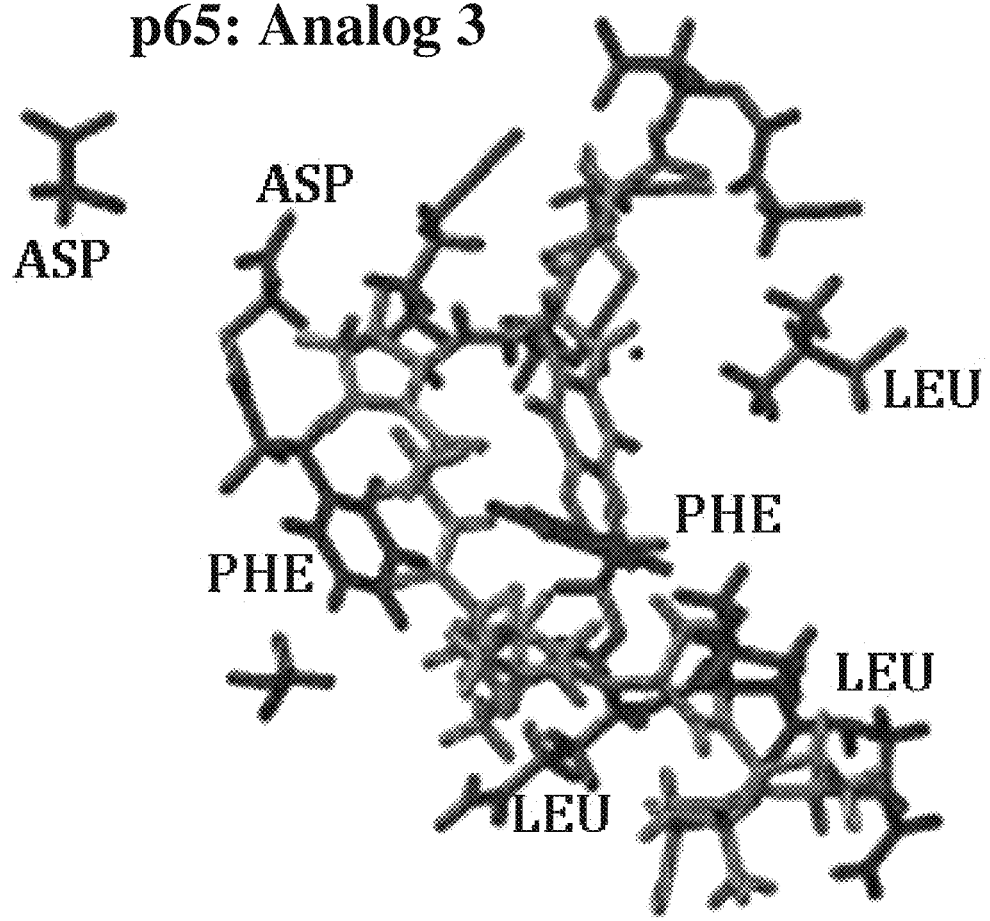
Figure 2C:
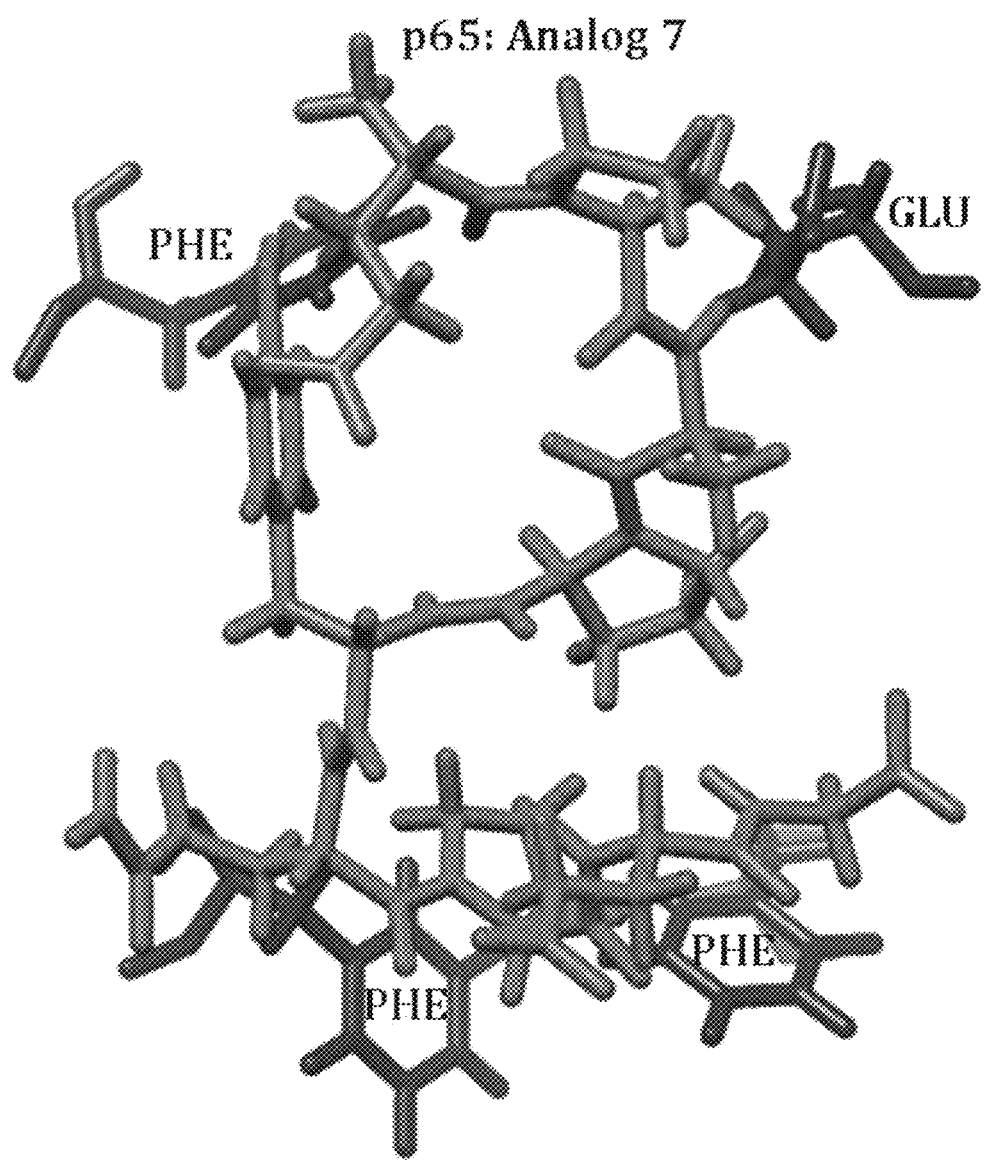
Figure 2D:
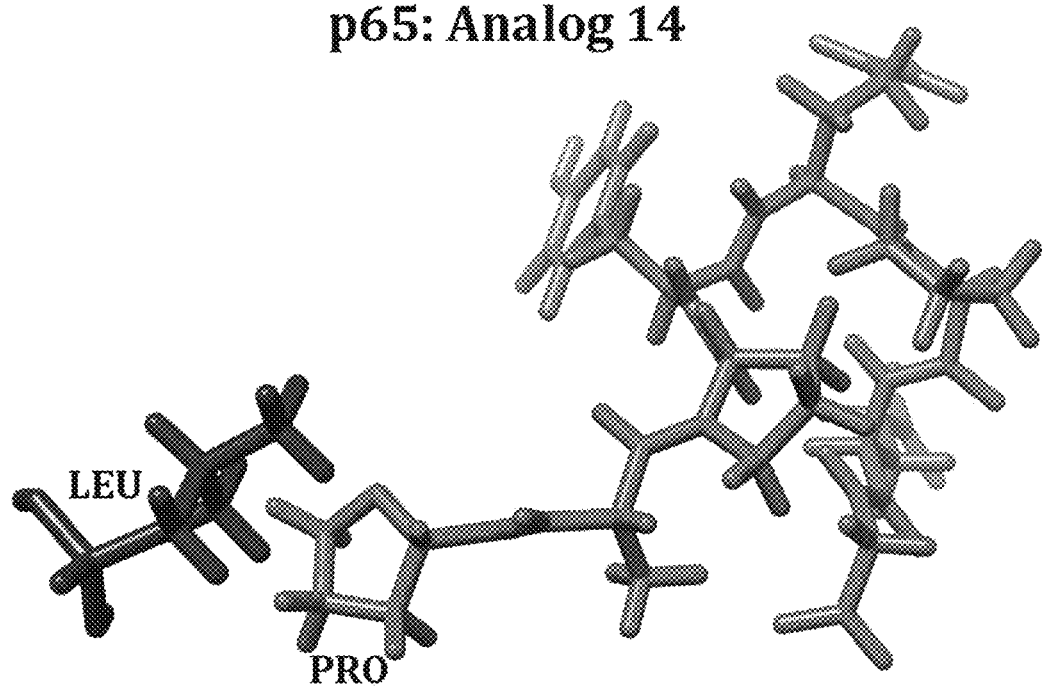
Figure 2E:
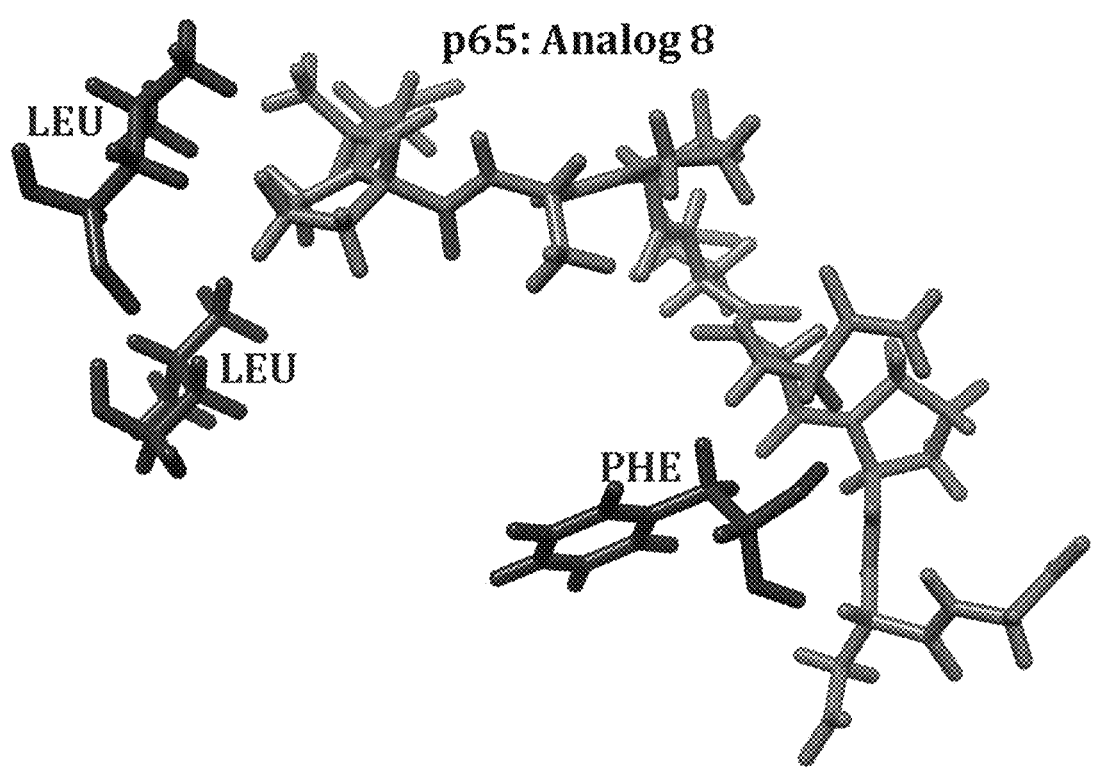
Figure 2F:
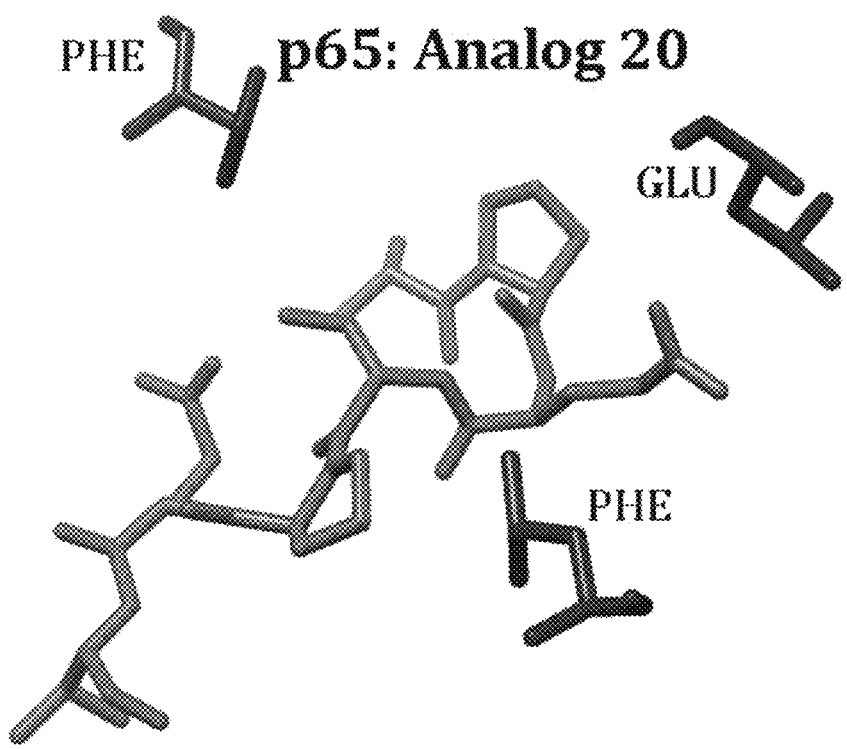
Figure 3A:
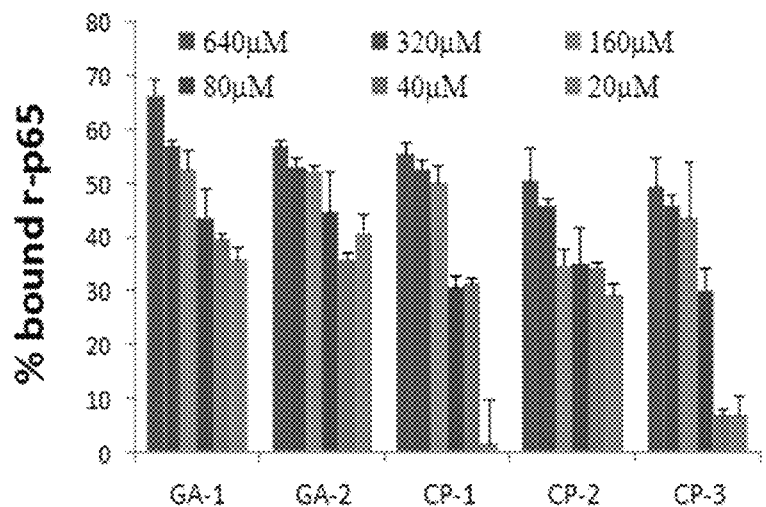
FIGS. 3A-3F show GA-rp65 binding analysis. Binding between the plate-bound GILZ analog (GA) or control peptide (CP) (20 μM-640 μM) at increasing concentration and the r-p65 was detected with the anti-DDK as described in the methods section. A dose dependent decrease in percent bound r-p65 was observed in association with the GA (FIG. 3A). Scatchard plot analysis of bound p65 $(A_0-A)/(A_0)$ against the ratio of bound p65 to free GA $(y=(A_0-A)/(A_0)/[(A_0-A)/(A_0)/(a_0-i_0)]$ was used to determine the dissociation constant for the interaction between indicated GA and r-p65 (FIG. 3B-3F).
Figure 3B:
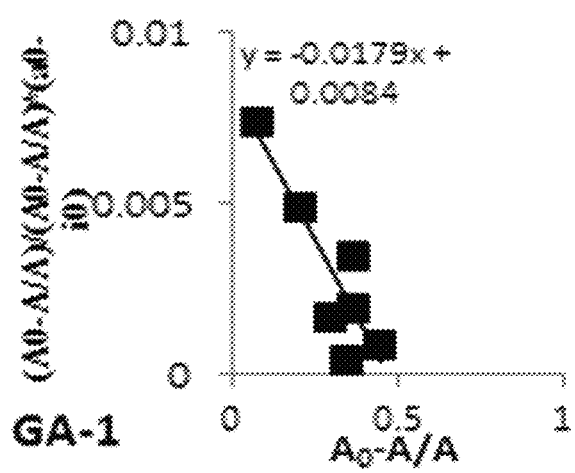
Figure 3C:
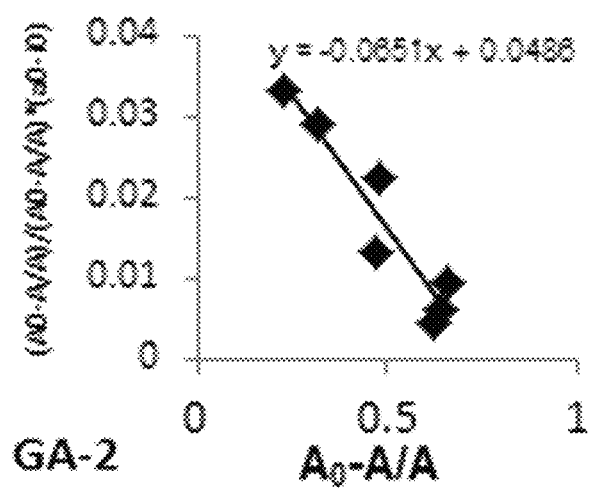
Figure 3D:
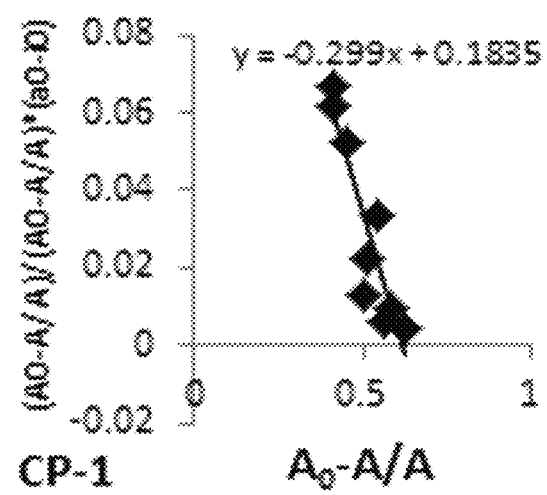
Figure 3E:
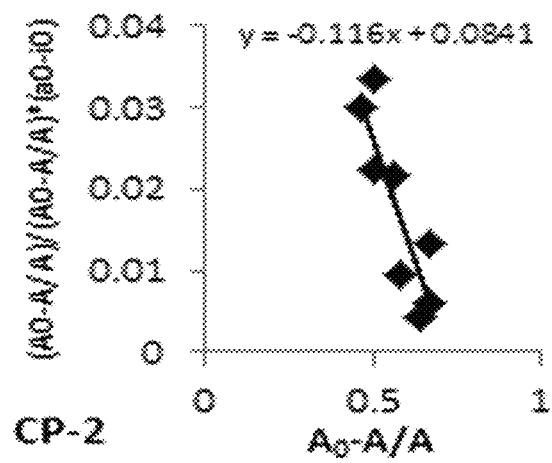
Figure 3F:
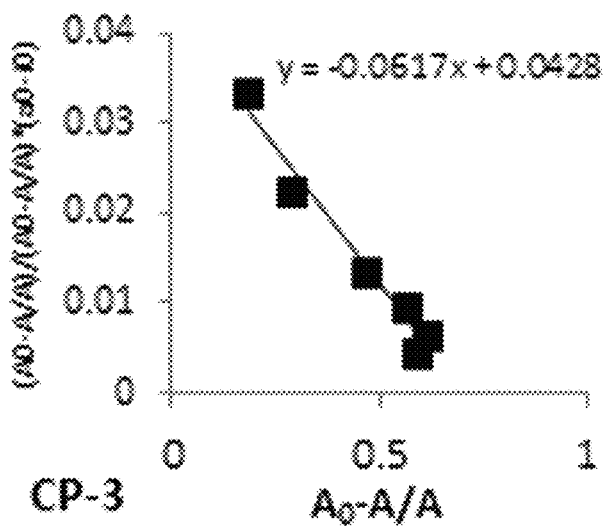

Sixty of the top one hundred predictions of wild type GILZ exhibited close proximity with nearly 50% of p65-$TAD_1$ residues suggesting near-native interactions (FIG. 2A). The wild type GILZ:p65-TAD complex with the lowest global energy and maximum contacts with p65-TAD was selected as reference for refining each of the 20 GILZ mimic-p65TAD complexes in two hundred independent FlexPepDock simulations. Significantly ten of the twenty GILZ mimics exhibited interatomic distance of <5 Å not only with the conserved phenylalanine in p65-$TAD_1$ but also with the putative LXXLL motif in p65-$TAD_2$ (FIGS. 2B and 2C). The LXXLL motif commonly observed in transcription factors are known to mediate protein-protein interactions. A rank order was developed based on percent PPII content, structural similarity with wild type GILZ and percent contact with p65-TAD. We selected two GILZ mimics or analogs (GA-1 and GA-2) that exhibit near native docking, structural congruence with experimental $PP_{II}$ and wild type GILZ and good $PP_{II}$ potential for screening by cellular analyses. In addition we selected one mimic with good $PP_{II}$ potential but fewer contacts with p65-TAD and two GILZ mimics that possess low $PP_{II}$ content but acceptable percent contact with the p65-TAD in docking analyses as control peptides for $PP_{II}$ conformation (control peptide 1) and p65 docking potential (control peptide 2 and control peptide 3) respectively.

Example 3

Binding of GILZ and human r-p65: Previously we observed that the r-GILZ exhibits ten times higher affinity than a 22 residue GILZ peptide for r-p65. We used similar method to determine direct binding kinetics of GA hexapeptides with human r-p65. High binding ELISA plates were coated with increasing concentrations of r-GILZ (0.5 μM to 20 μM) or each GA or control peptide (20 μM-640 μM) and probed with 80 pM r-p65 followed by detection with anti-DDK antibody. Absorbance at 650 nm was measured with a mixing time of 30 s using BIORAD microplate reader. Percent bound p65 was determined considering the binding response of r-GILZ (20 pM) with r-p65 as 100%. The dissociation constant of the interaction between the GA or the control peptide and r-p65 was determined by the method of Friguet et al., as described. A fraction of the bound r-p65 (x) and the ratio of bound r-p65 to the free GA or control peptide (y) was determined by the equations: $x=(A_0-A)/(A_0)$, where $A_0$ is the absorbance of r-p65 anti-p65 complex in the absence of bound GA or control peptide and $y=(A_0-A)/(a_0-i_0)\times(A_0-A)/(A_0)$, where $a_0$ is the total concentration of GA or control peptide and $i_0$ is the total concentration of r-p65. $K_D$ for the interaction was determined by the Scatchard equation: $x=1+K_D/y$.

Kinetics of GA:-p65 interaction: Previously the strength of interaction between rGILZ or wild type GILZ-P and r-p65 has been shown to be $5.91\pm2.4*10^{-7}$ M and $1.12\pm0.25*10^{-6}$ M, respectively. We evaluated the binding kinetics of individual GA at increasing concentrations with the plate bound r-p65 protein at constant concentration. We observed that the percent bound r-p65 was over 25% with GA-1, GA-2 and CP-1 even at the lowest concentration evaluated (FIG. 3A). The dissociate constant, $K_D$, as calculated by the method of Friguet et al. was $2.29+/-0.2\times10^{-6}$ M for GA-1 and $3.24+/-0.19\times10^{-6}$ M for GA-2. The strength of interaction of the GA:p65-TAD binding is consistent with other transient protein:peptide interactions such as that of peptide inhibitors of matrix metalloproteinase and that of SMRT peptides binding the BTB domain of BCL6. The control peptides exhibited higher $K_D$ values of $3.27+/-1.8\times10^{-6}$ M, $3.4+/-0.15\times10^{-6}$ M and $4.28+/-0.5\times10^{-6}$ M for CP-1, CP-2 and CP-3 respectively (FIGS. 3B-3F).

Example 4

Cell Titer-Glo (CTG) luminescent cell viability assay: Human neuroblastoma (SK-N-SH) cells cultured in minimal essential medium (MEM) supplemented with 1% fetal bovine serum (FBS) and 1% penicillin (100 U/ml)/streptomycin (100 μg/ml) were differentiated with 10 μM all-trans retinoic acid for 7 days. After resting for 24 hours in the low serum medium, the cells were seeded in 24 well ($10^5$ cells/well) culture plates in fresh medium and incubated with 50 μM or 500 μM of individual GA or control peptide for additional 24 hours. The cultures were then photographed using a phase contrast Leica microscope (Leica Microsystems Inc, Buffalogrove, Ill.). Subsequently, the cells were harvested, lysed with lysis buffer (M-PER, Pierce) and the lysate was assessed for metabolic activity using the luciferase based CTG assay (CTG, Promega, Madison, Wis.). Briefly, cell lysate (5 μL) in 25 μL of phosphate buffered saline was transferred to an opaque white 96-well plate, and then 30 μL of CTG assay solution was added. The relative luminescent signal (RLT) was quantified using a Glowmax luminometer (Promega).

Figure 4A:
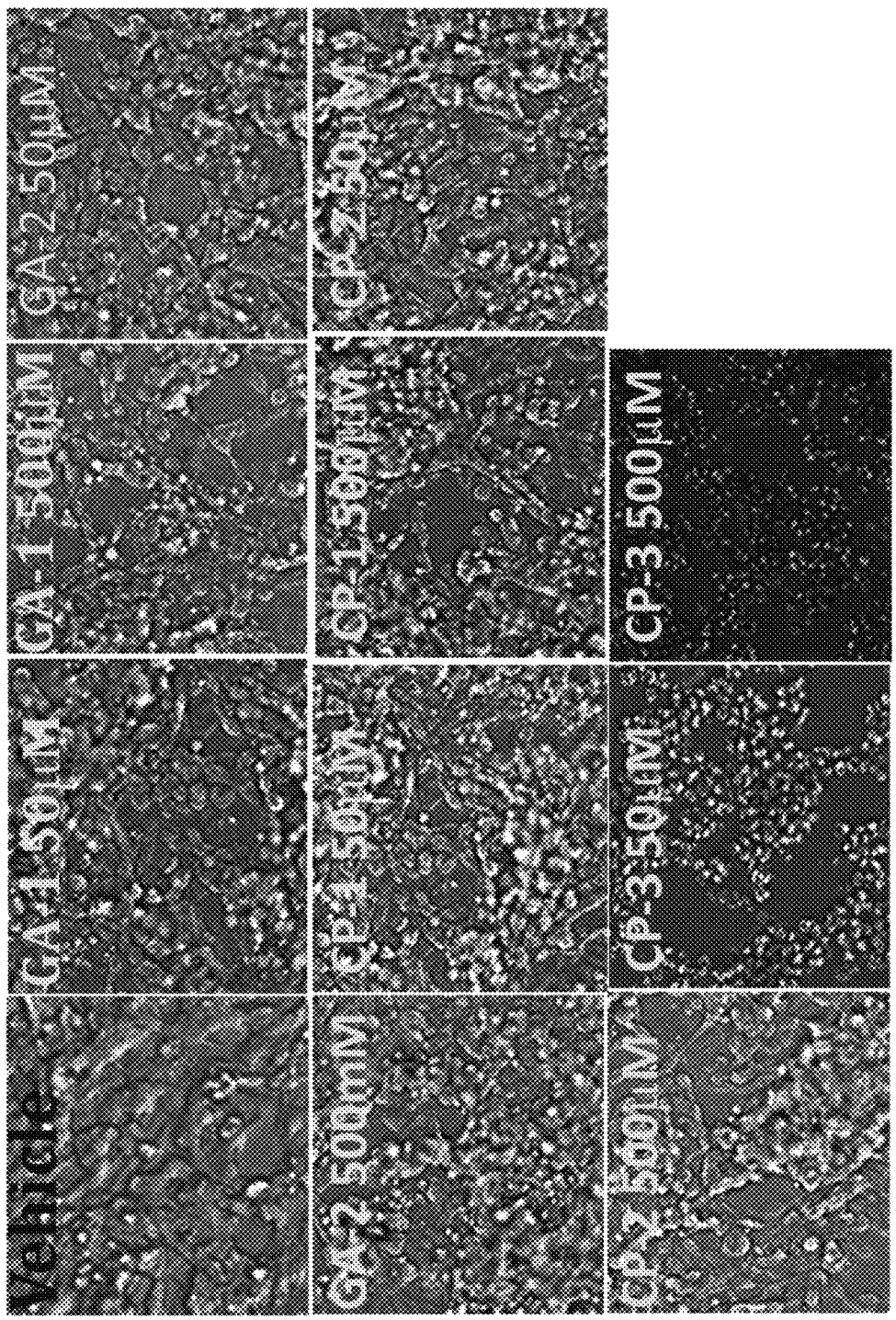
FIGS. 4A and 4B show the effect of GILZ analog (GA) on cellular morphology and metabolic activity in neuroblasts. Differentiated SK-N-SH neuroblastoma cultures were exposed to individual GA or control peptide (CP) at the indicated concentration for 24 hours.
Figure 4B:
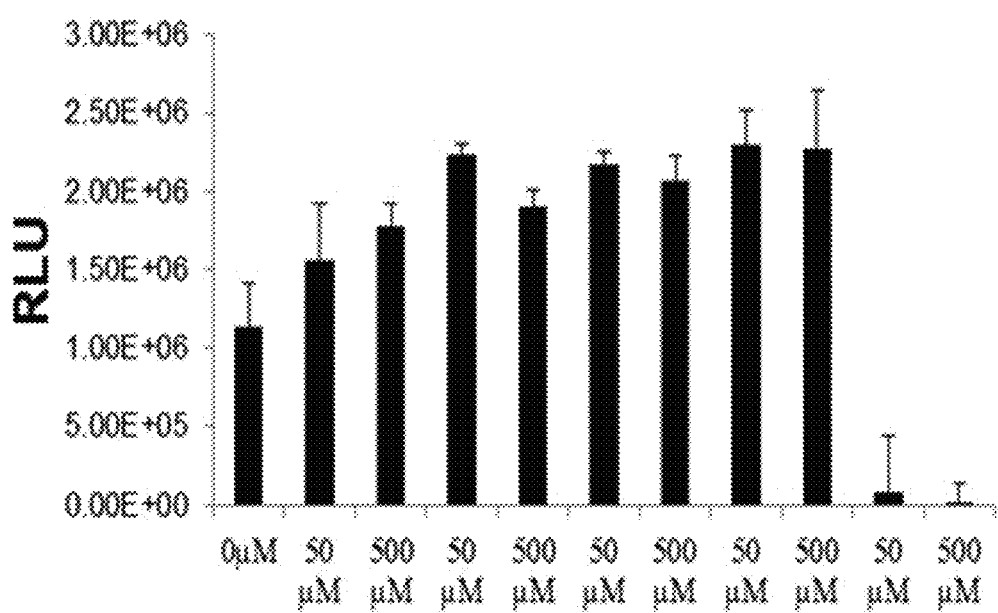

Effect of GA on cellular morphology and metabolic activity: Any compound with potential therapeutic effect should be biocompatible and nontoxic. So, we first screened the effects of GA on cellular morphology and viability. Cultures of neuroblasts exposed to 50 μM or 500 μM of individual GA or CP-1 or CP-2 did not show any change in cell morphology suggesting that the four peptides were not toxic. Exposure to CP-3 at either concentration showed morphological changes consistent with cell death (FIG. 4A). The effect of GA on cellular metabolic activity was assessed by the CTG assay which measures intracellular ATP concentrations as an indicator of actual cell number. The results of the CTG assay were very similar and showed that the two GA and CP-1 and CP-2 did not adversely affect the differentiated neuroblastoma cells, but treatment with CP-3 reduced the viability of the cells at both concentrations tested (FIG. 4B).

Example 5

Lactate dehydrogenase (LDH) assay: To detect direct GA-induced cell lysis we performed LDH release assays (Roche Molecular Diagnostics). Human glioblastoma (U373) cells were maintained in MEM supplemented with 10% PBS and 1% penicillin (100 U/ml)/streptomycin (100 μg/ml) at 37° C. in 5% $CO_2$-humidified incubators and sub-cultured once or twice a week. Approximately $5\times10^4$ U373 cells/well were cultured in 96-well plates in the presence of increasing concentrations of individual GA or control peptide from 0.5 μM to 500 μM. Cells treated with 2% triton-X 100 (Sigma Aldrich, St. Louis, Mo.) for 10 minutes served as positive control. Untreated cells served as controls for spontaneous LDH-release. Specific LDH-release was calculated according to the following formula: LDH-release %=100*(GA or control peptide treated cells−untreated cells)/(positive control−untreated cells). The IC50 values were extrapolated by logarithmic estimation. The $LD_{50}$ in mg/kg was predicted using the formula, Log $(LD_{50})= 0.506\times(\log IC_{50})+0.475$.

Detection apoptosis by flow cytometry: To further assess cell cytotoxicity, the apoptotic effects of individual GA or control peptide was evaluated by the Annexin-V and propidium iodide (PI) dual staining method (Annexin-V-Fluos staining kit, Roche Diagnostics, Mannheim, Germany) As opposed to apoptotic cells, necrotic cells with ruptured cell membrane take up PI, the DNA binding dye. Thus, cells which take up both fluorochromes are a mixture of apoptotic and necrotic cells, whereas cells that exclude PI but bind Annexin V are (early) apoptotic cells. U373 cells cultured with varying concentrations of individual GA or control peptide (0.5 μM to 50 μM) for 24 hours were centrifuged and suspended in 100 μl of Annexin V/PI labelling solution (20 μl each of Annexin-V-Fluos labelling reagent and PI in 1 ml of binding buffer) for 15 min at room temperature. After washing the cells were resuspended in PBS:1% paraformaldehyde and analyzed using a FACScan flow cytometer (BD Biosciences, San Jose, Calif.).

Figure 5A:
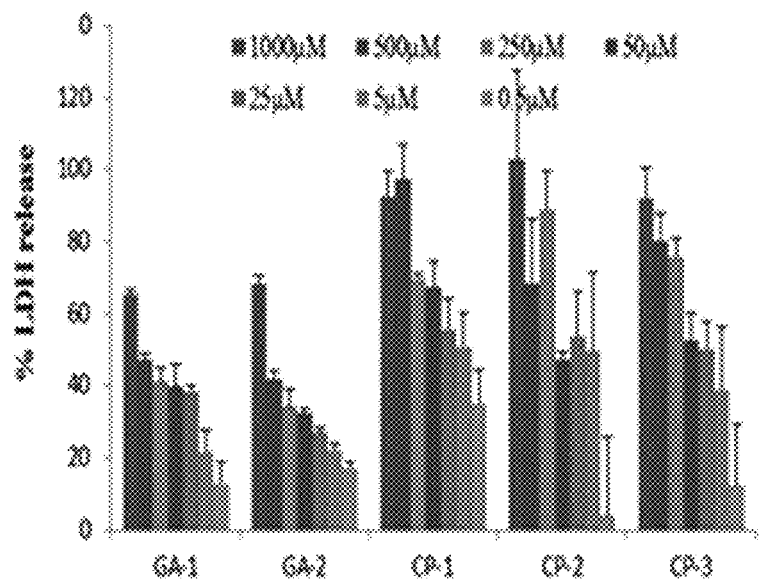
FIGS. 5A-5G show the effect of GA on lactate dehydrogenase (LDH) release. U373 MG astroglioma cells were exposed to increasing concentrations of indicated GILZ analog (GA) or control peptide (CP) (0.5 μM to 1 mM) for 24 hours. The release of LDH into the cell culture supernatant from damaged cells was measured. Percentage of LDH was calculated as the ratio of the difference between the peptide treated and untreated cells to that of the difference between the positive control and the untreated cells (FIG. 5A). The IC50 was determined by logarithmic extrapolation (FIG. 5C-5G). Flow cytometric analysis of Annexin positive U373 cells treated as indicated was determined as a measure of apoptosis (FIG. 5B).
Figure 5B:
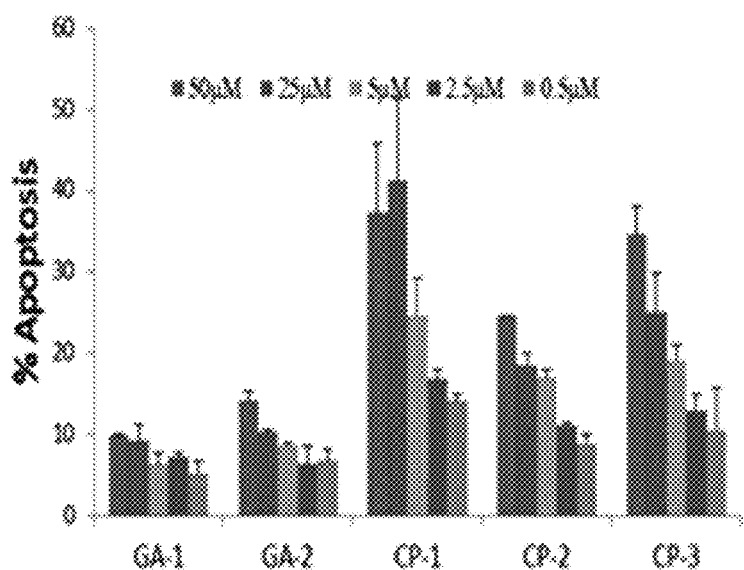
Figure 5C:
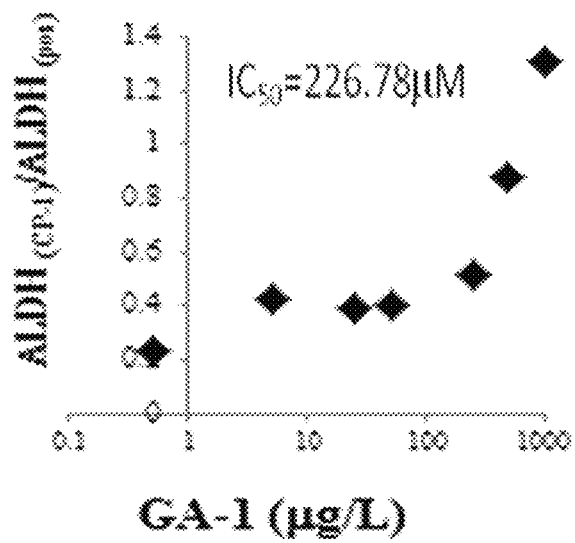
Figure 5D:
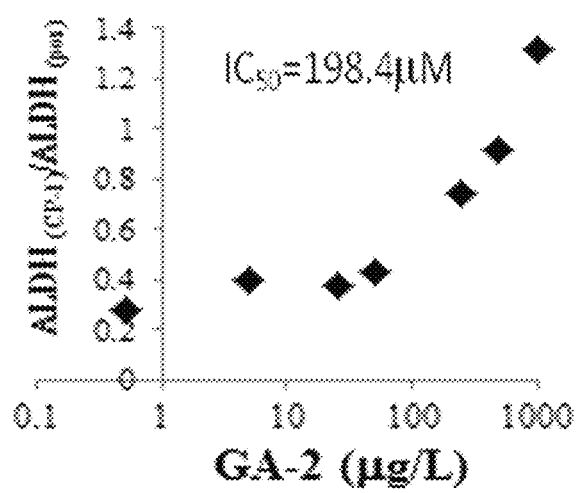
Figure 5E:
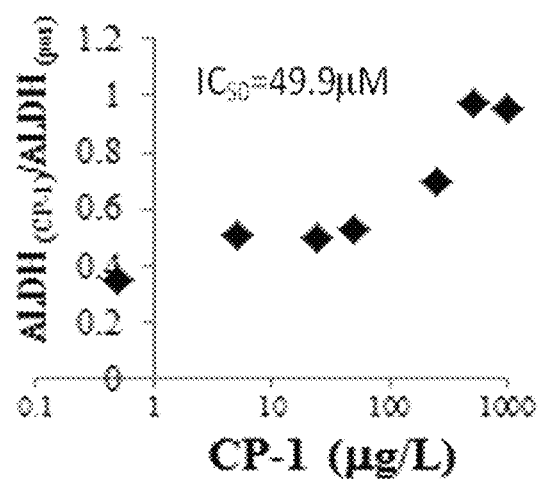
Figure 5F:
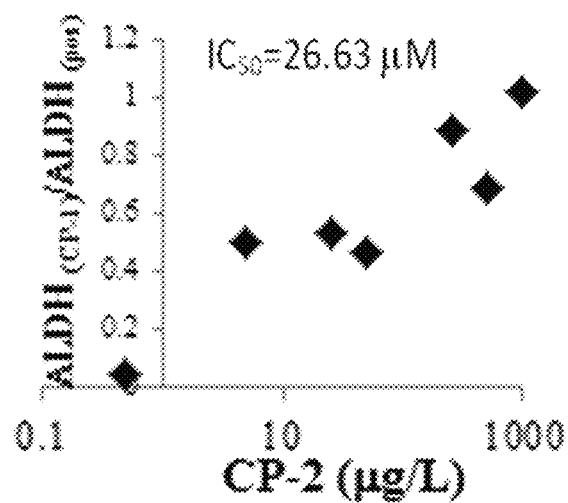
Figure 5G:
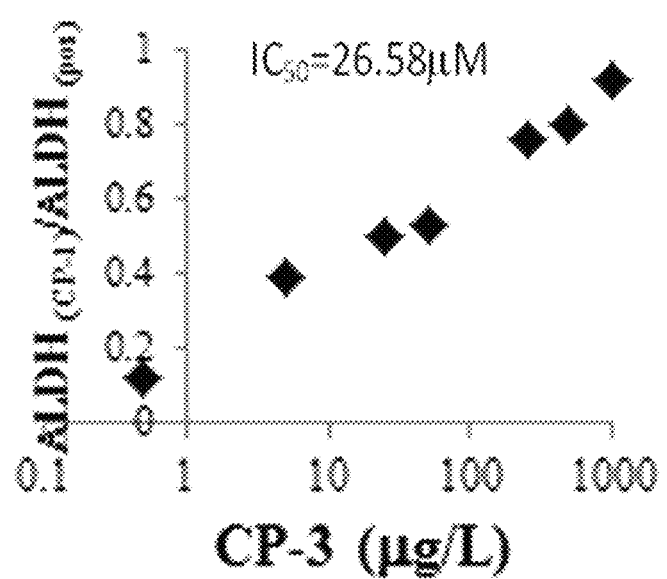

Effect of GA on membrane integrity and apoptosis: Membrane integrity as a measure of cell survival was assessed by the leakage of intracellular LDH molecules into culture medium. Treatment with GA-1 and GA-2 were best tolerated as indicated by the reduced % LDH release at all concentrations as compared to untreated cultures or cultures exposed to control peptides (FIG. 5A). $IC_{50}$ extrapolated from regression analysis is 226.78 μM for GA-1 and 198.4 μM for GA-2 (FIGS. 5C and 5D). The $IC_{50}$ was lower for CP-1 (49.9 μM), CP-2 (26.58 μM) and CP-3 (26.63 μM) (FIG. 5E-5G). Using the Speilmann method, the LD50 in mg/kg body weight is estimated to be 380.44 for GA-1 and 369.42 for GA-2 and 272.78, 237.52 and 237.62 for CP-1, CP-2 and CP-3, respectively. Many therapeutic peptides such as leuprolide and glatiramer acetate have been shown to exhibit similar $LD_{50}$ values. Furthermore the cytotoxic effect of each peptide at increasing concentration from 0.5 μM to 50 μM was assessed by Annexin and PI staining (FIG. 5B). GA-1 and GA-2 exhibit <25% apoptosis at highest concentration.

Example 6

Functional assays in human primary mixed brain cultures (HFB). Primary cultures of mixed HFB were prepared from the brain parenchyma of aborted fetuses (80-100 days gestational age). The tissues were obtained from the Birth Defects Research Laboratory (BDRL) at the University of Washington, Seattle with approval from the Indiana University Institutional Review Board (IRB). The IRB determined that the use of anonymous human biological materials received from this depository is not considered as human subjects research (supplementary document, s1). The NIH funded BDRL tissue distribution program operates separately in full compliance with all relevant state and federal laws and regulations with donors providing written informed consent.

Fetal brain materials (10-20 g) were shipped overnight in chilled Hibernate-E medium (Invitrogen) supplemented with B27 (Invitrogen), GlutaMAX (Invitrogen) and antibiotic-antimycotic solution (Cellgro). HFB were prepared and cultured as described. Briefly, cells were cultured in Neurobasal medium (Invitrogen) without phenol red supplemented with 1×B27, 50 mM GlutaMAX, 1× antibiotic cocktail, 5 ng/mL recombinant fibroblast growth factor 2 (bFGF) (Invitrogen), and 2 μL/mL Normocin (InVivoGen, San Diego, Calif., USA). Cells were counted and seeded onto poly-D-lysine (Sigma-Aldrich) coated 24-well plates (Corning, Lowell, Mass., USA) at $1.5\times10^5$ cells per well and maintained at 37° C. in a 5% CO2 incubator. Half media changes were performed every 4th day of culture and morphology was monitored via phase contrast microscopy. Culture medium was removed from cells on day 17 (DIV17) and replaced with Neurobasal medium with B27. Appropriate wells were then added vehicle, or carrier peptide or individual GA or control peptide (at 50 μM) for 30 min followed by exposure to $A\beta_{1-42}$ at a final concentration of 10 μM/well and incubated for 4 hours or 48 hours. Cells and conditioned media were harvested and stored for further analysis. Relative ATP concentration was measured using the CTG kit (Promega). Data is presented as ΔRLU=RLU of $A\beta_{1-42}$ exposed cells–RLU unexposed cells. Conditioned media collected were assessed for specific cytokines using the OptEIA kits (BD Biosciences). Nuclear and cytoplasmic fractions were extracted using the CelLytic™ NuCLEAR™ Extraction Kit (Sigma) following manufacturer's protocol. Five microgram of nuclear extracts was incubated in a 96-well plate coated with oligonucleotides containing the NF-κβ consensus nucleotide sequence (5'-GGGACTTTCC-3') (SEQ ID NO: 30). The activated NF-κβ bound to DNA was detected by anti-p65 antibody followed by a peroxidase coupled secondary antibody and substrate using the TransAM kit protocol (Active Motif). Nuclear extracts of Raji cells was used as the positive control.

Figure 6A:
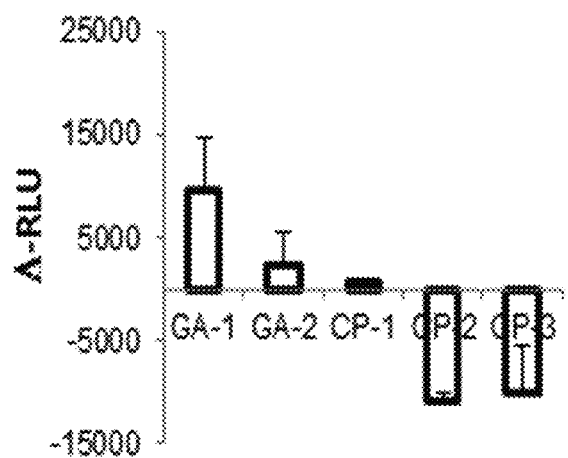
FIGS. 6A-6E show the effect of GILZ analog (GA) treatment on human fetal brain cells. Primary cultures of HFB (Div 17) were exposed to Aβ1-42 and treated with 50 µM of indicated GA or control peptide (CP). Cytoplasmic extracts of cells collected at 24 hours was assessed for viability by CTG assay. Data are presented as ΔRLU (difference in relative luminescent units (RLU) between the Aβ1-42 exposed cells and unexposed cells) (FIG. 6A, FIG. 6B). Culture medium collected at 24 hrs was assessed for indicated cytokines (FIG. 6C, FIG. 6D). Effect of GA on NF-κβ activation. Primary cultures of HFB exposed to Aβ1-42 (10 µg/ml) and treated with indicated GA or CP as above were harvested at the end of 4 hours. 5 µg of nuclear extract was tested for binding of the activated p65 NF-κB subunit to an NF-κB consensus sequence using the Trans AM NF-κB ELISA kit. The p65 DNA binding activity was calculated as the ratio of absorbance from Aβ1-42 stimulated cells to that of unstimulated cells (FIG. 6E). Values are the average/−S.D. $*=p<0.05$ as compared to Aβ1-42 exposed cells, $@=p<0.05$ as compared with Aβ1-42 and CP-1 or CP-2 treated cultures
Figure 6B:
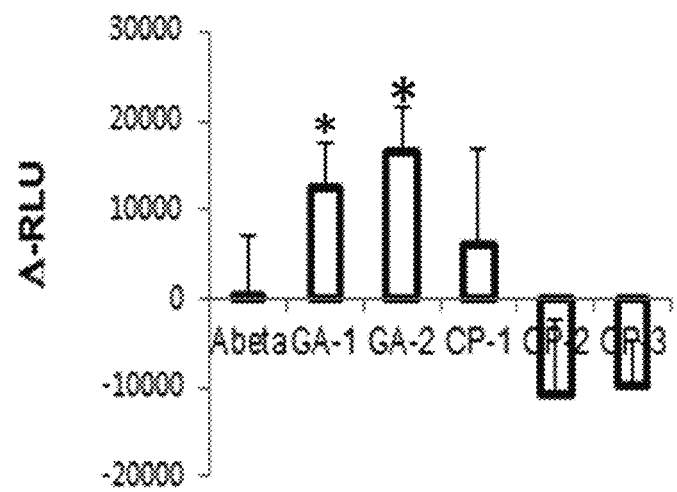
Figure 6C:
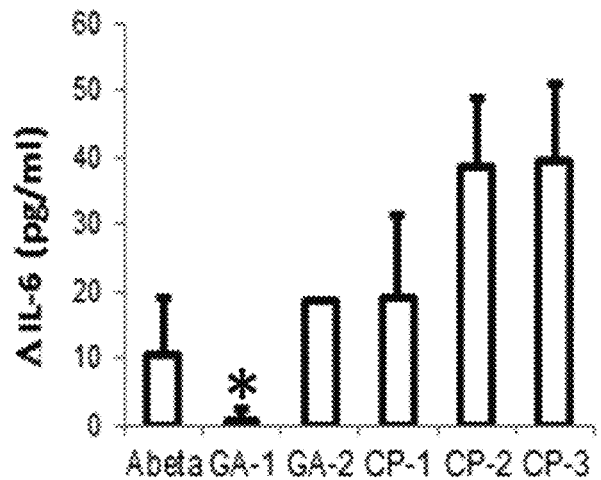
Figure 6D:
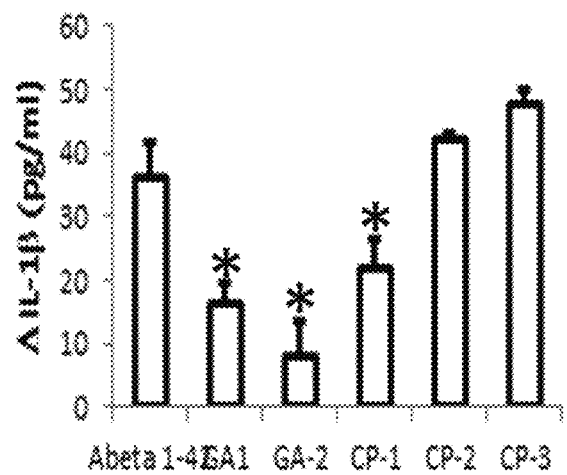

Select GA protect against $A\beta_{1-42}$ induced toxicity in human fetal brain cells. We used an in-vitro neurodegeneration model in which primary human fetal brain cells are allowed to mature gradually. The system provides an opportunity to test the pharmacological and toxicological effects of GA on differentiated neurons and glia simultaneously. The relative ATP concentration of GA or control peptide treated HFB cultures in the presence or absence of Aβ1-42 over the cultures exposed to vehicle alone (Δ-RLU) was determined by the CTG assay. Cultures exposed to GA were best tolerated while the cultures treated with CP-2 or CP-3 exhibited significant toxicity (FIG. 6A). The mean RLU of vehicle treated cells varied between 7352.75+/−1265.2 and 16157.5+/−4950 and the average RLU of cultures exposed to Aβ1-42 varied between 6067.25+/−903.05 and 11574.25+/−4139.3 in different experiments. The viability was significantly higher in cells exposed to Aβ1-42 and treated with GA-1 or GA-2 (FIG. 6B). Although Δ-RLU was higher in cultures treated with CP-1, it was not significant when compared to that in untreated Aβ1-42 exposed cultures. The relative concentration of IL-1β and IL-6 was significantly lower in culture medium of cells exposed to Aβ1-42 and treated with GA-1 or GA-2 as compared with that from untreated or cultures treated with the control peptides (FIGS. 6C and 6D).

Figure 6E:
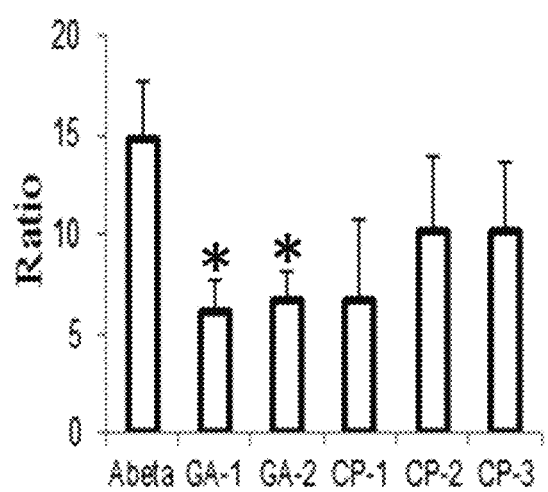

Select GA treatment inhibits activated p65: Previously Aβ1-42 has been shown to enhance expression of activated NF-κB in glia and post-mitotic neurons. We measured nuclear p65 binding activity using activated NF-κB specific ELISA. Nuclear p65 was significantly higher in cells exposed to Aβ1-42 than in unexposed cells (FIG. 6E). There was a trend towards decreased nuclear p65 in Aβ1-42 exposed cells treated with GA-1 and GA-2 as compared to untreated cells or cells treated with control peptide. No significant difference in nuclear p65 was observed in cells treated only with the peptides in the absence of exposure to Aβ1-42.

Comparative analysis of physical and functional characteristics of known receptor antagonists and peptide drugs in clinical use today with that of GA, suggest that the GA-1 and GA-2 exhibit significant drug like properties (Table 2).

TABLE 2

Physical and functional characteristics of GILZ analog and control peptides

| | Structural similarity RMSD | | | | Docking features | | | | | # rotatable bonds | | Log P | | $K_D$ (uM) | | LD50 (mM) | | % apoptosis at LD50 | | Overall rank |
| | Wild type GILZ | | PPII peptide | | % TA1 | | % TA2 | | % PPII | | | | | | | | | | | | |
| | <1 | >1 | <1 | >1 | >25 | <25 | >25 | <25 | >25 | <25 | <10 | >10 | <5 | >5 | <3 | >3 | >100 | <100 | <25 | >25 | |
| | 1 | 0 | 1 | 0 | 1 | 0 | 1 | 0 | | | | | | | | | 1 | 0 | 1 | 0 | |
| PGA1 | 1 | | 1 | | 1 | | | 0 | | 0 | | 0 | | 0 | | 0 | | 0 | | 0 | 3 |
| PGA2 | 1 | | 1 | | 1 | | 1 | | 1 | | 1 | | 1 | | 1 | | 1 | | 1 | | 10 |
| PGA3 | 1 | | | 0 | 1 | | | 0 | 1 | | | 0 | 1 | | | 0 | 1 | | 1 | | 6 |
| PGA4 | 1 | | 1 | | 1 | | 1 | | 1 | | 1 | | 1 | | | 0 | 1 | | 1 | | 9 |
| PGA5 | 1 | | 1 | | | 0 | 1 | | | 0 | | 0 | | 0 | | 0 | 1 | | | 0 | 4 |

Example 7

Design and selection of PGA: Human GILZ has an amino terminal α-helix for dimerizing and a carboxy terminal proline glutamic acid rich region for intermolecular interactions. Mutational and binding analyses showed that the proline rich region of GILZ adopts an extended $PP_{II}$ helical conformation and binds the p65-TAD. In the GILZ:p65 complex, interaction between the imino ring of $P^{120}/P^{123}$ of GILZ and the side chain of $F^{534}/F^{542}$ in the p65-TAD could promote C—H.π interactions and provide substantial binding energy. Functional studies have shown that the highly conserved $F^{534}$ and $F^{542}$ in the transactivation domain are critical for p65 induced transactivation.

Forty PGA were designed by incorporating rational substitutions in the p65 binding domain of GILZ with residues that facilitate $PP_{II}$ formation and stabilization at the interface with the p65-TAD. Homology models of PGA built using delta sleep inducing peptide (DSIP; PDB:1DIP) as template were screened for conformational constraints by superimposing on experimental $PP_{II}$ and wild type human GILZ. The $PP_{II}$ content of all PGA as determined by PROSS method ranged from 14.3%, 28.6% and 42.9%. Since $PP_{II}$ helix formation is often a locally driven event, the synthetic PGA with blocked end groups will likely adopt a similar conformation as in the predicted model. Twenty PGA that exhibit structural congruence with DSIP (<1 A), wild type GILZ and experimental $PP_{II}$ structure (<2 Å) were selected for docking analysis.

Figure 9A:
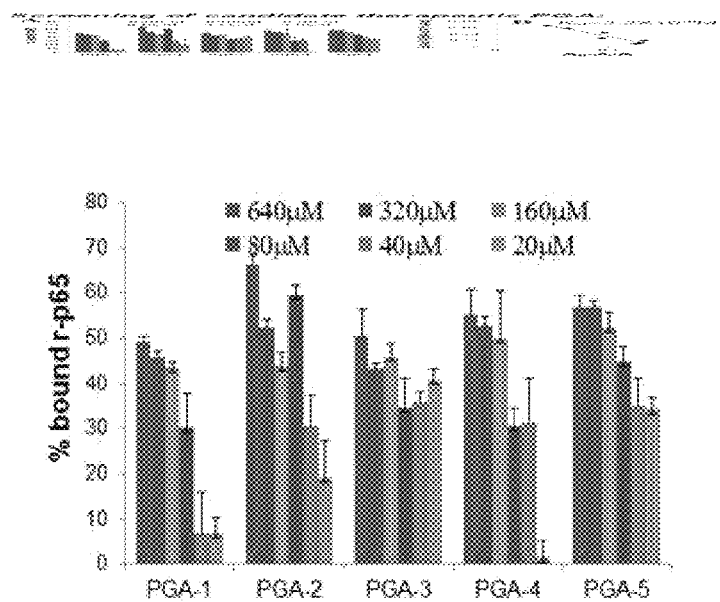
FIGS. 9A-9C show binding between plate-bound PGA (20^M-640^M) and r-p65 (15 pg/ml).

Homology model of p65-TAD was built using elongation factor eEF3 (PDB:3H7H) as template. Spatial orientation of wild type GILZ peptide or each PGA with p65-TAD was assessed by multiple algorithms including rigid-docking based on shape complementarity and coarse refinement methods that restrict side-chain flexibility at interface. The docked complexes were ranked using an optimized global energy function. Significantly most solutions of top ten PGA exhibited close proximity to the phenylalanines ($F^{534}$, $F^{542}$) and the putative LXXLL motif in p65-TAD (see FIGS. 9C and 9D). The LXXLL motif in transcription factors has been shown to mediate protein-protein interactions. A rank order developed based on percent $PP_{II}$ content, structural similarity with wild type GILZ and percent contact with p65-TAD identified five PGA with near native docking and good $PP_{II}$ potential. The top five PGA were selected for cellular analyses (see FIGS. 8A-8D).

Example 8

Figure 9B:
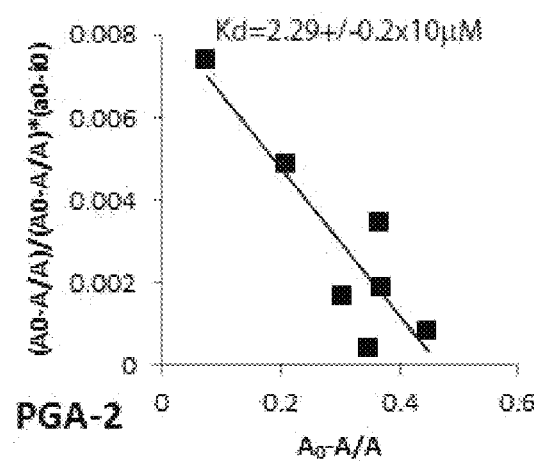
Figure 9C:
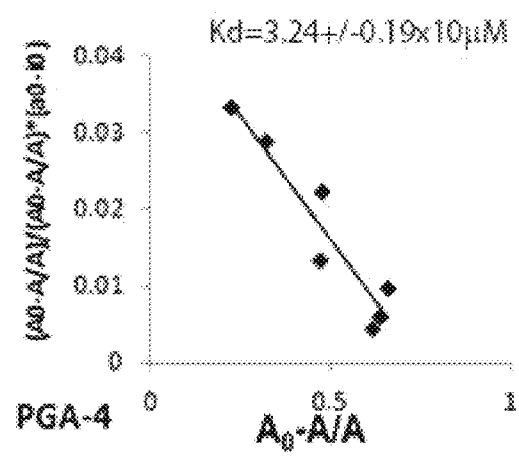

Kinetics of PGA:-p65 interaction: The binding kinetics of top five PGA with full length human r-p65 was assessed as described. Plate bound GILZ-P or PGA at increasing concentrations was probed with r-p65-DDK (Ori-Gene Technologies Inc., Rockville, Md.) at constant concentration and detected with anti-DDK. The percent bound r-p65 increased with increasing concentration of PGA (see FIG. 9A). The dissociation constant, $K_D$, calculated by the method of Friguet, was lowest for PGA-2 ($2.29+/-0.2\times10^{-6}$ M) followed by PGA-4 ($3.28+/-0.2\times10^{-6}$ M), PGA-5 ($3.4+/-0.2\times10^{-6}$ M), PGA-3 ($3.27+/-1.8\times10^{-6}$ M) and PGA-1 ($4.28+/-0.5\times10^{-6}$ M) (FIGS. 9B-9C).

Example 9

Effects of PGA on membrane integrity and apoptosis: The top five PGA were covalently synthesized with the cell penetrating TAT (transcriptional transactivation) peptide to facilitate intracellular delivery (Genescript, NJ). Membrane integrity of U373 microglial cells exposed to increasing concentration of each PGA from 0.5 μm to 500 μM was assessed by the leakage of intracellular lactate dehydrogenase (LDH) into culture medium (Roche, IN).

Figure 10A:
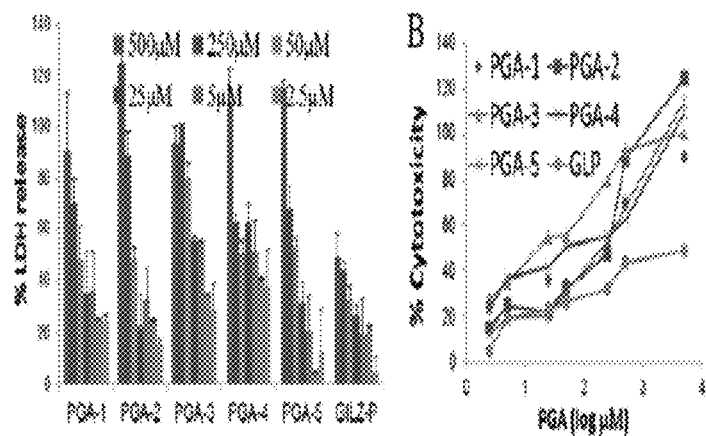
FIGS. 10A and 10B show U373 cells were exposed to increasing concentrations of different PGA or wild type GILZ-P (0.5 µM to 500 µM) for 24 hours. Percent LDH released into the medium was calculated as the ratio of the difference in PGA treated to untreated cells to that of the difference between the positive control and untreated cells (FIG. 10A). The $IC_{50}$ was determined by logarithmic extrapolation (FIG. 10B).
Figure 10B:
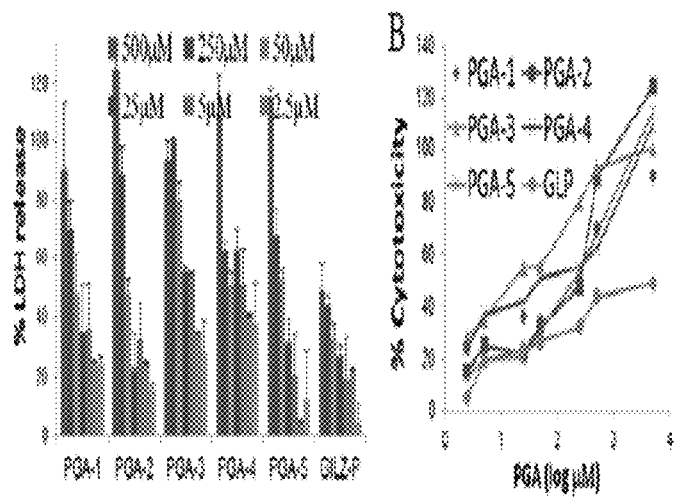
Figure 13A:
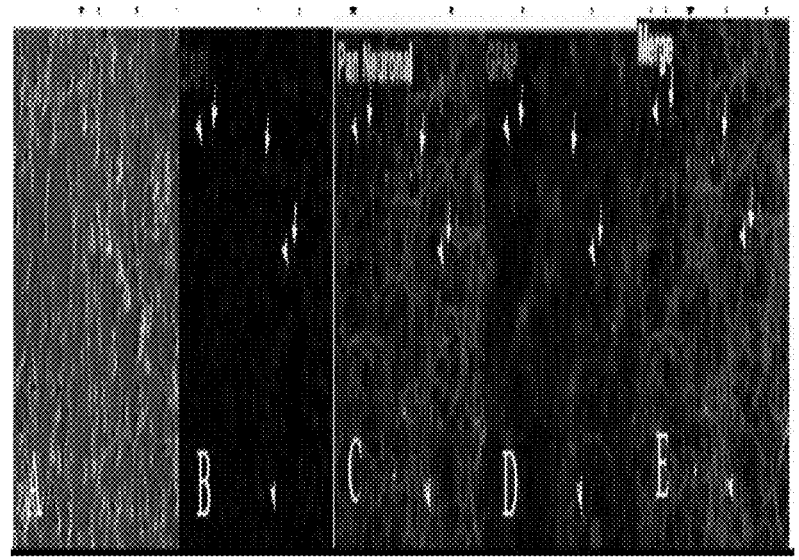
FIGS. 13A-13E show HFNC cultures at DIV20. A phase contrast image (FIG. 13A) and nuclear staining with DAPI (FIG. 13B) are displayed.
Figure 13B:
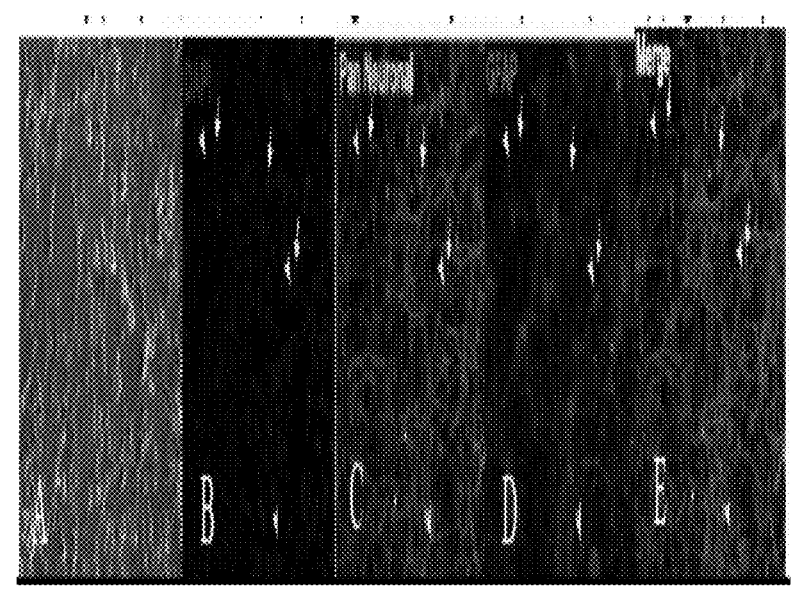
Figure 13C:
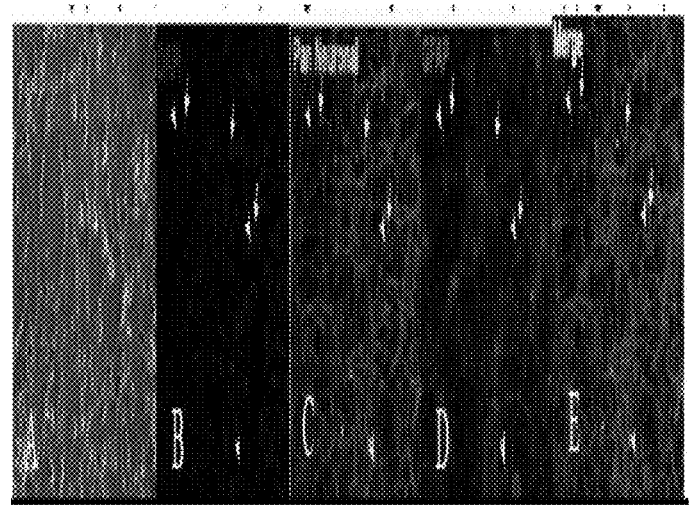
Figure 13D:
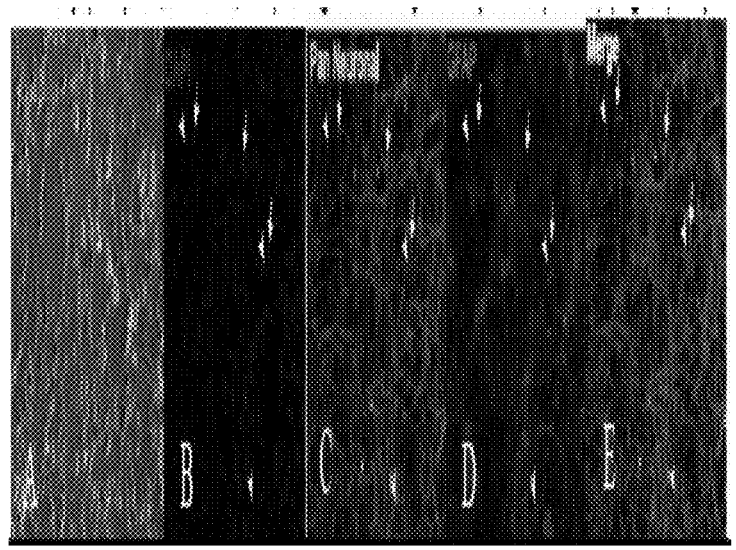
Figure 13E:
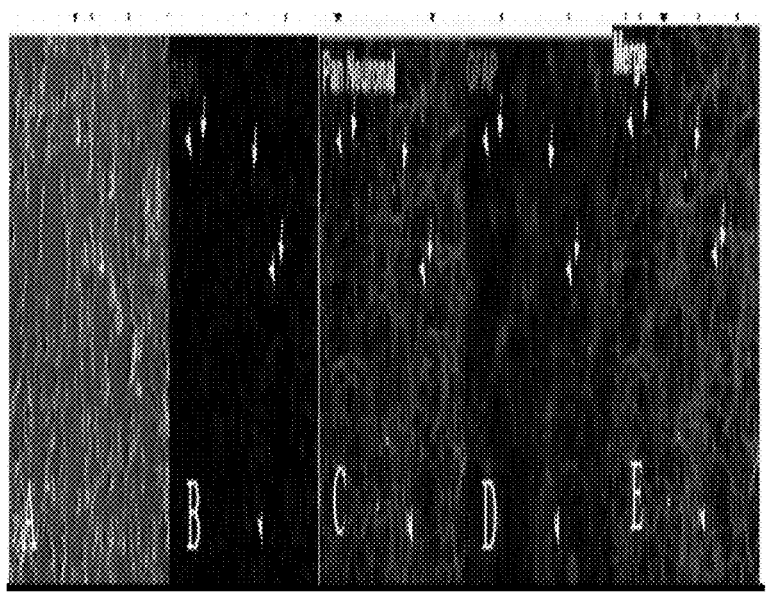

All five PGA exhibited a dose dependent LDH release (FIG. 10A). $IC_{50}$ extrapolated from regression analysis was highest for PGA-1 (2.27 μM) followed by PGA-5 (2.0 μM), PGA-2 (1.95 μM), PGA4 (1.5 μM) and PGA-3 (0.98 μM) (FIG. 10B). The cytotoxic effect of each PGA at increasing concentration from 0.5 μM to 50 μM was also assessed by Annexin and PI staining. PGA-2 and PGA-4 exhibit <25% apoptosis.

Example 10

Select PGA protects against $A\beta_{1-42}$ induced toxicity, prevents p65 activation and cytokine response in human fetal brain (HFB) cells. Primary HFB cells pretreated with vehicle or each PGA at $IC_{50}$ concentration were cultured in the presence of $A\beta_{1-42}$ aggregates (10 μM) for 24 hours at 37° C. and 5% $CO_2$. Viability in terms of relative luminescent Units (RLU) was quantified using a Glowmax luminometer (Promega, WI). Data are presented as ARLU=RLU of $A\beta_{1-42}$ exposed cells-RLU of unexposed cells. HFB cultures exposed to PGA-2, PGA-3 and PGA-4 were well tolerated. Cultures treated with PGA-1 and PGA-5 exhibited significant toxicity (FIG. 11A). The mean RLU of vehicle treated HFB varied between 7352.75+/-1265.2 and 16157.5+/-4950. Average RLU of cultures exposed to $A\beta_{1-42}$ varied between 6067.25+/-903.05 and 11574.25+/-4139.3 in different experiments. The viability was significantly higher in HFB cells treated with PGA-2, PGA-3 or PGA-4 and exposed to $A\beta_{1-42}$ (FIG. 11B). The culture supernatants were assessed for cytokines by ELISA (R&D Systems, MN). AIL-1p (not shown) and AIL-6 concentration was significantly lower in PGA-2, PGA-4 or PGA-5 treated cultures over unstimulated or cultures exposed to $A\beta_{1-42}$ alone (FIG. 11C). Primary HFB cultured similarly and harvested at the end of 4 hours was assessed for nuclear p65 using TransAM kit for NF-κB p65 (Active Motif, CA). $A\beta_{1-42}$ exposed cells treated with PGA-2 and PGA-4 exhibited decreased nuclear p65 (FIG. 11D).

Example 11

Evaluation of the effect of PGA-2 and PGA-4 on AD-relevant cells. An in-vitro neurodegeneration model derived from primary HFNC can be utilized in the instant example. Previously maturing HFNC cultures have been shown to exhibit positive staining for neuronal, glial and synaptic markers. Further, the neuronal population has been shown to increase with time and exhibit physiological activity. In addition the cells are capable of being transfected with external agents providing a tool for evaluating the efficacy of potential drug candidates for CNS pathologies. Importantly, abundant Aβ production and tau proteins make this a powerful model for Alzheimer's research. The effects of PGA-2 and PGA-4 on neuronal and glial cell morphology, BACE-1 and Aβ production in primary HFNC can be evaluated. (see FIGS. 13A-13E).

HFNC: Briefly, human brain cells derived from aborted fetus (90-110 days gestational age) can be plated in poly D-lysine coated 24-well plates (Sigma, St. Louis, Mo.) using defined culture medium (Neurobasal medium with 1×B27, 50 mM Glutamax, 1× antibiotics cocktail and recombinant human basic fibroblast growth factor 2 (bFGF) at 5 ng/mL (Gibco, Grand Island, N.Y.) and incubated at 37° C., 5% $CO_2$. Half media changes can be performed every fourth day and morphology monitored by phase contrast microscopy. The procedure usually results in ~75% pure neurons. Purity of the cultured cells has been demonstrated by visualization of neurons and glia using pan-neuronal antibody (Millipore, Billerica, Mass.) and glial fibrillary acidic protein (GFAP) (Sigma) respectively.

PGA treatment and immunocytochemistry: PGAs were covalently synthesized with the cell penetrating TAT to facilitate intracellular delivery as peptide amides with amino terminal acetylation. At DIV16 (mixed population of neuronal and glial cells) or DIV20 (predominantly mature neurons) of HFNC, the defined culture medium can be replaced with Neurobasal medium supplemented only with B27. PGA-2 (168.9 μM), PGA-4 (101.7 μM) at $IC_{50}$ concentration or TAT peptide (100 μM) can be added and the cultures continued to be incubated for 24 hours. The effect on neuronal and glial cell morphology can be assessed by immunostaining using fluorophore conjugated astroglial markers (GFAP) and neuron specific proteins (Nestin, Pan N). Stained sections can be visualized with an inverted fluorescent microscope (Leica Microsystems) and appropriate sets of filters.

Quantitation of BACE-1 and AB: Separate HFNC cultures at Div16 can be added PGA-2, PGA-4 or TAT (carrier). Equal quantity of cDNA isolated from cells harvested after 24 hours can be amplified for BACE-1, APP and reference genes (3-2 microglobulin and GAPDH by real time polymerase chain reaction (Applied Biosystems; assay IDs: human BACE-1 (Hs00201573_m1), human APP (Hs01552283_m1), human GAPDH (4333764T), human B2M (4333766T). Fold changes can be calculated using the delta-Ct method normalized to the geometric mean of the reference genes. Levels of $A\beta_{1-40}$ and $A\beta_{1-42}$ in the culture medium can be measured using specific commercially available ELISA kits (Covance, Princeton, N.J.). Absolute $A\beta$ values (in pg/ml of culture medium) can be normalized to total protein and scaled relative to levels in untreated cultures.

As PGA-2 or PGA-4 did not affect the morphology of HFNC as seen under inverted bright field microscope, HFNC exposed to either PGA may exhibit significant neuronal staining on day-20 suggesting neuropreservation. Transfection of human brain cells with NF-κB dependent miRNA has been shown to downregulate BACE-1, APP and $A\beta$ production. By blocking p65, PGA-2 and PGA-2 treatment may reduce BACE-1 transcription and consequent $A\beta$ production.

Example 12

Investigation of the molecular effects of PGA on AD relevant cells: Accumulating environmental and oxidative stress induces NF-κB p65 activation in neuronal and glial cells contributing to AD pathogenesis. Quantitation of biologically active molecules integrally involved in AD pathology is used as outcome measures in early stages of drug discovery.

Cell culture: HFNC cultures at Div16 added PGA-2 or PGA-4 at $IC_{50}$ or TAT (carrier) as above can be exposed 30 minutes later to $H_2O_2$ (10 μM) or sodium nitroprusside (SNP) (30 μM) as radical oxygen or nitric oxide donor respectively for 4 hours or 24 hours. Some cultures can be added a cell permeable 2',7'-dichlorofluorescin diacetate (DCFH-DA) (10 μM) (Molecular Probes, Eugene, Oreg.) probe at the time of PGA treatment to measure reactive oxygen species (ROS). Cells and culture medium can be collected for RNA and protein analysis.

Evaluation of activated NF-κB. cytokines and glutamate: The effect of PGA on p65 transactivation in each cell type can be evaluated by co-labeling of cells harvested at 4 hours using fluorophore conjugated markers for neuron (NSE, Nestin, Pan N), astrocytes (GFAP); microglia (IBA1) and nuclear p65 (Abcam Cambridge, Mass.) and visualized with an inverted fluorescent microscope. Activated p65 in nuclear fraction of cells can be quantitated by ELISA. IFN-α, IL-iβ and IL-6 and glutamate in culture medium collected at 24 hours can be measured using specific ELISA kits (R&D Systems, MN) and enzymatic assays (BioVision Inc. Milpitas, Calif.) respectively.

Cytoprotection assays: Fluorescence in cell lysates added DCFH-DA and collected at 4 hours can be measured at 504/529 nm and data expressed as ratio of ROS to total protein. Activated caspase in culture medium can be measured using caspase-3 assay kit (R&D systems). Total protein isolated from cells harvested at 24 hours can be probed by immunoblot (Abcam) for apoptosis related proteins Bax, Bcl-2 and caspase-3 using specific antibodies. Fold changes in these apoptotic proteins transcripts can be determined by polymerase chain reaction arrays (Applied Biosystems; Human TaqMan® Human Apoptosis Array; Cat. #4414072).

Other neuroprotective agents suppressed caspase-3 and Bax in neuronal cells. Preliminary data suggest that PGA-2 and PGA-4 may suppress cytokines and cytotoxic mediators. Alternatively primary rat cortical neuronal cells (PRCN) can be used to evaluate the effects of PGA.

Example 13

Evaluation of the In-Vivo Efficacy of PGA in a Transgenic Mouse Model of AD

Selection of Animal Model: The R1.40 APP YAC transgenic mice created by introducing entire genomic copies of mutant human APP (with K670N/M671L FAD substitutions) into the mouse genome can be utilized in the instant example. As compared to the cDNA based hAPP transgenic mice, the R1.40 APP YAC transgenic mice exhibit regional $A\beta$ distribution, preferential deposition of $A\beta_{1-42}$, overlapping deposition of APOE, extensive neuritic abnormalities, and increased markers of inflammation mimicking many characteristics of human AD. Inhibition of NF-κB by tolfenamic acid has been shown to reduce cerebral $A\beta$ plaque burden in homozygous R1.40 mice.

Experimental Procedures:

Animals: Starter pair of R1.40 [B6.129-Tg(APPSw)40 Btla/Mmjax mice (Stock #034831)] can be purchased from Jackson Laboratory (Bar Harbor, Me.). Breeding colonies can be genotyped and maintained under standard animal housing conditions in a 12-hour dark light cycle with free access to food and water at the laboratory animal resource facility (LARC) at IU School of Medicine (IUSM). The background strain for R1.40 is mixed, which can serve as non-AD controls. All experiments can be conducted according to the Institutional Animal Care and Use Committee (IACUC) and approved by the local ethics committee.

PGA dosing and treatment regimen: The $LD_{50}$ calculated using the in-vitro $IC_{50}$ values and the regression equation [log $(LD_{50})=0.506\times\log(IC_{50})+0.47551$] for PGA-2 and PGA-4 equals 1396.83 mg/kg and 1693.87 mg/kg bodyweight respectively. Appropriate dose of PGA-2 and PGA-4 can be dissolved in 100 μl of sterile PBS for i.p administration. R1.40 APP YAC transgenic mice develop parenchymal and vascular amyloid deposits by 12-13 months and exhibit reactive gliosis by 14-16 months. Four groups with 7 homozygous mutant APP YAC transgenic mice each can be administered daily either saline, PGA-2, PGA-4 or carrier peptide (TAT) at 1300 mg/kg (equivalent to $LD_{50}$ of PGA-2) for four weeks beginning at week 40.

Histology: Mice can be perfused transcardially with ice cold PBS 4% paraformaldehyde at the end of four weeks. Brain tissues can be harvested, frozen and stored for histological analysis. Sections of entorhinal cortex, orbitofrontal cortex, and frontal cortex can be stained for congophilic dense-core amyloid plaques and immunostained for $A\beta$ plaques and inflammatory markers including Iba1, IL-6, IL-1β, TNF-α, and NF-κB-P65.

Photomicrographs can be analyzed for percent stained area for plaque load and inflammation. An inflammatory focus is defined as the presence of clusters of 20 or more aggregated mononuclear cells. The total number of inflammatory foci can be counted from 3 different sections of each specimen.

Leuprolide (5 g/kg) and glatiramer acetate (230 mg/kg) administered i.p. for similar periods were efficacious in models of AD. These peptides have been measured in the cerebrospinal fluid in optimum concentrations suggesting efficient CNS delivery and substantiating the credibility of peptide drugs for AD. Based on the mechanisms of actions of GILZ and preliminary data, percent stained area of congo red positive plaques, Aβ plaques and inflammation may be significantly reduced in PGA treated mice.

Example 14

Transformation of PGA into small molecule agents: PGA peptides are rationally designed structural mimics of GILZ in the contest of the p65-TAD binding interface. Specific inhibition of activated p65 by PGA has been shown to suppress inflammatory and cytotoxic responses in-vitro and in-vivo.

Three dimensional structure databases incorporated within the modeling programs of CAVEAT and PHASE can be searched to identify templates with bonds that adopt $PP_{II}$ orientation and serve as attachment points. The functional groups of critical proline of human GILZ or the substituted PGA residue can be grafted onto the non-peptide scaffold. The resultant PGA pharmacophore can be characterized by binding affinity and functional studies. A similar approach has been previously used successfully in developing inhibitors of Factor Xa for treating coagulation pathologies.

PepMMsMIMIC is a virtual screening platform tool used to identify pharmacophore or chemical compounds that mimic a natural peptide or protein in 3D space. Using this tool, a three dimensional similarity search of PGA-2/PGA-4 structure can be initiated amongst seventeen million conformers calculated from commercially available chemicals. Top peptide mimetic can be ranked by two different scoring functions taking into account high electrostatic, chemical and shape complementarity together with pharmacophore fingerprints similarity. Using this method, multiple small molecule nutlin analogues have been identified as peptidomimetics of MDM2/p53 interaction. Preliminary search suggests that the chemical moiety, methyl-N-butyl-N [2,6-di-nitro-4-(trifluormethyl)phenyl] carbamate, may be similar to PGA-2 peptide.

Modified amino acids or incorporation of enantiomers may be used to enhance identification of PGA specific pharmacophore.

Example 15

Suppression of Pathology in an Alzheimer's Disease Model

Peptides: GA-1 and GA-2 are peptides designed to mimic the $PP_{II}$ helical orientation of the p65 binding motif of the GILZ. The control peptides include sequence control consisting of residues with little propensity for $PP_{II}$ helix (CP-1) formation and/or for binding p65-TAD (CP-2) or unstructured peptide with no p65 binding potential (CP-3). All peptides were co-synthesized with the cell penetrating agent TAT (GRKKRRQRRRPQ, SEQ ID NO: 31) for intracellular delivery as peptide amides with amino terminal acetylation (Genescript, Piscataway, N.J.). All peptides were purified by semipreparative RP-HPLC and the identity of the purified peptide was confirmed by mass spectrometry.

Animals and lipopolysaccharide induced neuroinflammation: Male C57/6J mice weighing 32 to 37 grams were housed five per cage at a temperature of 22±2° C. with 12 hour light/12 hour dark cycles with free access to laboratory food and water. Lipopolysaccharides (LPS) from *Escherichia coli* 026:B6, =10,000 EU/mg, purified by phenol extraction was purchased from Sigma (Sigma Aldrich, Mo., USA). The mice were randomly divided into seven groups: LPS, LPS+GA-1 or GA-2 or CP-1 or CP-2 or CP-3 or TAT. The LPS was administered intraperitoneally at 250 mg/kg in 100 μl of sterile saline followed by corn oil in the morning daily for six days. The GA or CP was administered intravenously at 25 mg/kg in 100 μl of sterile saline on alternate days. Additional control group included mice receiving saline alone. All animals were sacrificed on day 7.

Histology and immunohistochemistry: The mice were sacrificed on day 7 by intra-cardial perfusion of 25 ml of 0.9% saline. Brain from each mouse was removed, one half was immediately frozen and the other half fixed in 4% paraformaldehyde for 24 h and later in 10% neutral buffered formalin for additional 24 h. Fixed tissues were subsequently processed for paraffin embedding. Tissue sections (5μ) stained with Harris's haematoxylin and counterstained with eosin were assessed for inflammation.

Immunohistochemistry: Serial 5μ thick coronal sections of each brain specimen were immunostained for markers of microglial cells, astrocytes and NF-κB p65. Briefly, after deparaffinization and hydration sections were subjected to antigen retrieval by microwave incubation in 10 mM sodium citrate buffer (pH 6.0) followed by sequential incubation in 30% hydrogen peroxide and blocking buffer (Enzo biosciences,) to reduce non-specific binding. The sections were then stained with the following primary monoclonal antibodies from EMD Millipore Corporation, Temecula, Calif., USA: anti-Iba-1 (AIF1 clone: Cat. #MABN92) or anti-glial fibrillary acidic protein (GFAP) clone GA5 (Cat. #MAB3402, Millipore) or anti-CD11b (Cat. #. MABF513) clone M1/70 or anti-NF-κB p65 subunit clone 12H11 (Cat. #. MAB3026). For mono-staining of Iba-1 and GFAP, detection was with the use of IHC select immunoperoxidase secondary detection system (Millipore). The peroxidase conjugated streptavidin-biotin method was used and brown staining was considered positive. For dual staining of CD11b and NF-κB p65 detection was achieved using the MULTIVIEW® (mouse-HRP/rabbit-AP) IHC kit (Catalog #: ADI-950-100, ENZO Lifesciences, Farmingdale, N.Y., USA). For each marker, to confirm the specificity of the antibodies, a separate set of sections from each group were incubated with only the secondary antibodies, a condition in which no staining was present.

Quantitative analysis of staining intensity: Images of the IHC stained sections were captured using the NIKON Multiphoton microscope with attached DS Ri2 camera. Five areas encompassing the hippocampus of each brain section were analyzed using the ImageJ Software. The number and the relative optical density of Iba1+ and GFAP+ glial cells was determined using the multi-point tool and the IHC-tool box. A training for brown/red color was performed prior to measurement to define the threshold for positive selection. Regions of interest encompassing the hippocampus were identified in each section, and the corresponding images were quantified using integrated optical density, normalized to the background optical density. Measurement of pixel intensity was restricted to the DAB or AP stained pixels of cells within defined circularity. Five consecutive coronal sections were assessed for each mouse.

Enzyme linked immunosorbent assay for cytokines: Frozen brain tissue was homogenized in RIPA lysis buffer (50 mmol/LTris-HCl, pH 6.8, 150 mmol/L NaCl, 5 mmol/L EDTA, 0.5% sodium deoxycholate, 0.5% NP-40) supplemented with a cocktail containing protease and phosphatase inhibitors (Chemicon, Millipore) on ice and then centrifuged at 16,000×g for 30 min. Supernatant was stored at −80° C. until further analysis. For each sample, 10 μL of extracted protein was used for measuring the cytokines IL-6, TNF-α, IFN-γ, IL-10 and TGF-β using specific OptEIA kits (BD Biosciences, CA).

NF-κB assay: Brain homogenates processed as above were assessed by the Cell Signaling Technology PathScan® Phospho-NF-κB p65 (Ser$^{536}$) Sandwich ELISA kit following manufacturer's protocol (Cell Signaling Technology, Boston, Mass.). Briefly, 40 µl of the extracted protein mixed with 60 µl of the sample diluent was added to phosphor p65 (Ser$^{536}$) mouse mAb coated microwells and incubated overnight at 4° C. After extensive washing, the captured phospho-NF-κB p65 protein was detected by incubating with horse radish peroxidase (HRP) conjugated NF-κB p65 rabbit mAb followed by washing and color development using the TMB substrate. Absorbance at 450 nM was measured using a microplate reader (Model 680; Bio-Rad Laboratories, Hercules, Calif., USA). Nuclear extracts of Raji cells was used as the positive control.

Real time polymerase chain reaction. Total cellular RNA was isolated from each brain tissue using Qiagen kit (Invitrogen, Carlsbad, Calif.) following manufacturer's protocol and reverse transcribed using iScript cDNA synthesis kit (Biorad, CA). Equal amount of cDNA measured by the Nanodrop (ThermoFisher Scientific, Waltham, USA) was used for amplification of IL-1β, IL-12, CD14, Bcl$_{XL}$ and Bcl2. Real time PCR was performed using SYBR green/ROX qPCR master mix (SA Biosciences, Frederick, Md.) on the ABI Prism 7000 sequence detection system (Applied Biosystem, Foster City, Calif., USA). Each reaction contains 2×12.5 µl of master mix, 1 µl of 10 µM of primers and 50 ng of the cDNA, to a total volume of 25 µl. The thermal cycling conditions included an initial denaturation step at 50° C. for 2 min, 95° C. for 3 min, 39 cycles at 95° C. for 30 s, annealing temperature at 62° C. for 30 s and extension at 72° C. for 30 s.

```
The primers are F-βActin:
                                (SEQ ID NO: 32)
5'TCATGAAGTGTGACGTTGACATCCGTA3';

R-βActin:
                                (SEQ ID NO: 33)
5'CCTAGAAGCATTTG CGCTGCACGAT GG3' (102 bp);

F-IL-1β:
                                (SEQ ID NO: 34)
5'AGCTGATGGCCCTAAACAGA3';

R-IL-1β:
                                (SEQ ID NO: 35)
5'GGTCGGAGATTC GTAGCTGG3' (89 bp);

F-CD14:
                                (SEQ ID NO: 36)
5'GAGCTAGACGAGGAAAGTTGT3';

R-CD14:
                                (SEQ ID NO: 37)
5'ACCGTAAGCCGCTTTAA GGACAGA3' (206 bp);

F-Bcl$_{XL}$:
                                (SEQ ID NO: 38)
5'TGGAGTAAACTGGGGTCGCATC-3';

R-Bcl$_{XL}$:
                                (SEQ ID NO: 39)
5'AGCCACAGTCATGCC CGTCAGG3' (84 bp);
and F-Bcl2:
                                (SEQ ID NO: 40)
5'CTCGTCGCTACCGTCGTCACTTCG3';

R-Bcl2:
                                (SEQ ID NO: 41)
5'GTGGCCCAGGTATG ACCCAG3' (96 bp).
```

The gene specific threshold cycle (Ct) for each sample (ΔCt) was corrected by subtracting the Ct for the housekeeping gene β-actin. Untreated controls were chosen as the reference samples. The ΔCt for all experimental samples was subtracted by the ΔCt for the control samples (ΔΔCt). The difference in each gene specific threshold between the sample from vehicle treated and GA or CP treated cells was determined to obtain the relative change in the specific mRNA. The magnitude of change in the mRNA was expressed as $2^{-\Delta\Delta Ct}$. Each measurement of a sample was performed in duplicates.

Example 16

Identification of Druggable Site: The Interface of p65:GILZ Interaction

Structurally p65 has dimerizing amino terminal rel homology domain, a nuclear localization sequence masked by the IκB inhibitory complex and carboxy terminal TAD. The transactivation activity of p65 is mediated by interactions of the TAD with co-regulators and the basal transcription machinery. The p65-TAD is commonly divided into two distinct regions, TAD-1$^{521-551}$ consisting of 36 amino acids and TAD-2$^{428-520}$ with 92 residues. While TAD1 accounts for nearly 95% of the transactivation potential of full-length p65, TAD2 alone is less potent mediating about 30% activation. In particular, the conserved aromatic residues (F$^{534}$, F$^{542}$), acidic residues (D$^{531}$, D$^{533}$) and phosphorylation sites (Ser$^{529}$,Ser$^{536}$) in p65-TAD1 have been identified as critical for transactivation.

GILZ is a p65-TAD binding protein that sequesters activated p65 and inhibits transactivation of inflammatory and apoptotic factors. Mutational, binding and structural studies suggested that the PER region of GILZ adopts a PP$_{II}$ helical conformation in the context of critical phenylalanine in p65-TAD. PP$_{II}$ helices highly represented at interfaces of transient protein interactions in human proteome and often behave as adaptable gloves in obtaining the correct binding orientation. The specificity of PP$_{II}$ interaction is determined by residues of the interacting partner. PP$_{II}$ interface mimics constitute excellent drug templates. GA are rationally designed peptides with residue substitutions in the GILZ-PER with increased propensity to form stability of PP$_{II}$ helical conformation in the context of p65-TAD (see FIGS. 14A-14D). Screening 40 GA, we selected two analogs referred to as GA-1 and GA-2 that exhibit good PP$_{II}$ potential, near native docking with p65-TAD, acceptable binding strength for transient interactions and inhibitory potential in cellular assays for evaluating the in-vivo therapeutic efficacy. In-silico predictions suggest that the predominant proteolytic products of GA-1 or GA-2 are to the right of the cell-penetrating carrier suggesting that the GA is potentially delivered intracellularly as intact cargo to bind the activated p65 in the cytosol.

Example 17

GA Prevented LPS Induced Microglial and Astrocyte Activation in the Hippocampus

Peripherally-injected LPS induces a variety of central effects. Multiple injections of LPS increase the number of F4/80+, CD11b+, or Iba1-+ cells and induce morphological changes characteristic of activated microglia in the CNS. It was observed that the mice induced neuroinflammation and treated with GA-1 or GA-2 exhibited reduced Iba1+ microglial cells and GFAP+ astroglial cells in the hippocampus as compared to that in the hippocampus of mice treated with control peptides or left untreated (see FIGS. 15A-15B and FIGS. 16A-16B). Furthermore, it was observed that the number of CD11b+ p65+ glial cells was significantly reduced in number and intensity in the hippocampus of GA-1 or GA-2 treated mice as compared to that in untreated or control peptide treated mice (see FIGS. 17A-17B).

Example 18

GA Suppresses LPS-Induced Accumulation of Inflammatory Proteins in the Hippocampus Brain tissues were investigated for cytokines known to be critical for microglial activation and gliosis in LPS-induced neuroinflammation. Brain tissue homogenates of GA-1 or GA-2 treated mice exhibited reduced IL-6 (18.7+/−2 pg/ml and 19.6+/−0.84 pg/ml respectively) treated mice as compared to the homogenates of untreated (32.4+/−4.7 pg/ml) or control peptide treated mice (FIG. 18A). Similarly, brain homogenates of GA-1 or GA-2 treated mice exhibited reduced TNF-α (1500.1+/−476 pg/ml and 1199.2+/−356.4 pg/ml respectively) as compared to the untreated (2287.7+/−473 pg/ml) or the control peptide treated mice (FIG. 18B). The concentration of IFN-γ was also significantly lower in brain tissue of GA-1 (2863.2+/−697.5 pg/ml) or GA-2 (3125.1+/−815 pg/ml) treated mice as compared to the untreated (4788.2+/−2069.1 pg/ml) mice (FIG. 18C). The concentration of IL-12 was also significantly lower in brain homogenates of GA-1 or GA-2 treated mice (92.0+/−9.3 pg/ml, 101.3+/−15.9 pg/ml) as compared with that in the brain tissues of untreated mice (132.9+/−17 pg/ml) or CP treated mice (FIG. 18D).

Example 19

GA Treatment Suppressed Activated NF-κB p65 in LPS-Induced Neuroinflammation

Since LPS is a potent stimulator of NF-κB and GA are designed to sequester activated p65, the activated p65 in the brain homogenates was measured using specific ELISA kits. It was observed that the absorbance suggestive of activated p65 was significantly lower in the brain protein extract from mice treated with GA-1 (0.098+/−0.03) or GA-2 (0.12+/−0.07) as compared to that of extract from mice left untreated (0.29+/−0.08) or treated with CP-3 (0.23+/0.09) (FIG. 18E).

Example 20

GA Treatment Inhibited LPS-Induced Suppression of Anti-Apoptotic Factors

To investigate the effects of GA on neurotoxicity, the expressions of anti-apoptotic factors $Bcl_{XL}$ and Bcl2 were determined by real time PCR. In addition, inhibition of LPS-induced cytokine secretion correlated with the decreased levels of steady-state mRNA for IL-1β in the brain tissues of in GA-1 or GA-2 treated mice (FIGS. 19A & 19B). It was observed that the relative expression of CD14 mRNA was significantly lower in brain tissues of GA-1(0.48+/−0.1) or GA-2 (0.64+/−0.4) treated mice as compared to that in the brain tissues of untreated (4.0+/−1.7) or control peptide (CP-1:1+/−0.3; CP-2:2.4+/−2; CP-3:1.2+/−0.1) treated mice (FIGS. 19A & 19C). Relative expression of $Bcl_{XL}$ and BCl2 was significantly higher in brain tissues of GA-1 (0.32+/− 0.15 and 1.25+/−0.5 respectively) or GA-2 (0.25+/−0.4 and 1.9+/−0.9 respectively) treated mice as compared to that in brain tissues of untreated (0.11+/0.1 and 0.22+/−0.5 respectively) or control peptide (CP-1:0.06+/−0.08 and 0.36+/−0.8, CP-2: 0.13+/−0.12 and 0.45+/−0.9; CP-3: 0.13+/−0.1 and 0.44+/−0.9 respectively) treated mice (FIGS. 19A, 19D, & 19E).

Example 21

Investigation of the Role of GILZ in the GC Mediated Neuronal Survival and Apoptosis GILZ exhibits opposing effects of increased proliferation and reduced survival in many cell types. While GILZ induces apoptosis in thymocytes, it protected activated T cells from apoptosis. Although GILZ expression in mouse brain has been observed, little is known about the role of GILZ in neurons.

Preliminary results: The expression of GILZ in human neuroblastoma cells was evaluated. SK-N-SH cells were cultured in minimal essential medium and differentiated with 10 μM all-trans retinoic acid for 7 days as described. After resting, the cells were cultured with increasing concentrations of dexamethasone (Dex: 0-10 μM) for 24 h and viability was determined by the MTT assay by measuring the absorbance of the intracellular formazon resulting from the reduction of the yellow tetrazolium MTT by the cell metabolic activity. Absorbance of vehicle treated cells was taken as 100% viable. GILZ expression was measured in protein extracts from separate SK-N-SH cultures by Western blot analysis using GILZ mAb [Santa Cruz Biotechnology, Dallas, Tex.]. Total RNA isolated from similar SK-N-SH cultures was reverse transcribed and the GILZ mRNA was amplified using the SYBR green qPCR mix (SA Biosciences, Fredrick, Md.) on the ABI Prism 7000 system (Applied Biosystem, CA).

```
The primers were:
GILZ-F:
                                  (SEQ ID NO: 42)
5'-CATGGAGGTGGCGGTCTA TC-3';

GILZ-R:
                                  (SEQ ID NO: 43)
5'-CACCTCCTCTCTCACAGCGT-3'
and GAPDH-F:
                                  (SEQ ID NO: 44)
5'AGGTCGGTGTGAACGGATTT G-3'
and GAPDH-R:
                                  (SEQ ID NO: 45)
5'-TGTAGACCATGTAGTTGAGGTCA-3'.
```

Results: DEX at 1 μM was not toxic but at higher (10 μM) concentration reduced the viability of SK-N-SH cells by 25% (FIG. 20A). The GILZ protein and the transcript was increased at lower but decreased at the highest DEX concentration tested (see FIG. 20B-20D).

At Low GC Concentration, MR Induced GILZ can Facilitate Neuronal Survival, but in High GC State GILZ Expression can be Decreased with Loss of Protection.

The GILZ gene has six GRE in its promoter region and hence its expression is highly regulated by both endogenous and exogenous GC. Furthermore, complete concordance observed between the GILZ protein and the mRNA implies that the regulation occurs at the transcriptional level. However, the dynamics of GILZ induction appear to vary in different tissues, suggesting that the local milieu could modulates its transcription. The goal of this example is to characterize the functions of neuronal GILZ and its regulation by GC.

Experimental Approach:

Culture of primary rat cortical neurons (PRCN): PRCN cultures can be generated as described. Briefly, brain tissues dissected from a 16-week old adult female Sprague-Dawley rat can be digested with papain. Neuronal cells isolated by gradient centrifugation using different Optiprep concentrations can be cultured for 12 days in Neurobasal medium supplemented with bFGF and Normocin (InvivoGen, San Diego, Calif.) at 37° C. and 5% $CO_2$ at which time point the cultures are rich in mature neurons. The purity of neurons can be identified by morphology (phase contrast appearance as bright cells, with smooth rounded somata and distinct processes) and immunocytochemical staining for NueN. Corticosterone (CORT) treatment: After transferring to serum free medium, the effects of a range of CORT concentrations (1 nM-10 µM) on cellular viability, cytotoxicity and GILZ induction in PRCN cultures can be analyzed. Since MR exhibits ten-fold higher affinity than GR for GC, we can next determine the relative contribution of MR and GR in GILZ induction. Separate PRCN cultures will be treated with MR antagonist spinorolactone (1 µM) or GR antagonist RU 486 (50 nM) prior to treatment with varying CORT concentration (1 nM-1 µM) to selectively block MR and GR respectively. In the preparation of CORT, RU486 and spinorolacotone the concentration of 100% ethanol can be at <0.1% in the culture medium.

The PRCN cultures in each experiment can be harvested at the end of 24 h, 48 h and 72 h. The primary read outs for these experiments can include i) assessment of cell viability and toxicity by MTT and lactate dehydrogenase (LDH) assays using cell lysates, ii) measurement of GR transactivation in nuclear extracts by the enzyme-linked immunosorbent assay-based TransAM GR kit (Active Motif, CA), iii) quantitate GILZ protein by immunocytochemistry and immunoblot in cell lysates and iv) quantitate GILZ mRNA by RT-PCR.

The role of GILZ in the bimodal effects of glucocorticoid mediated neuronal survival and apoptosis will be analyzed via overexpression of GILZ in PRCN: PRCN can be transfected with pCMV6-GILZ-Myc-DDK using Tsc22d3 (NM_001077364) Mouse Tagged ORF Clone (CAT #: MG225004, OriGene Technologies Inc., Rockville, Md.) as per manufacturer's protocol. Initial transduction at different multiplicity of infection can be performed to determine the optimal transduction efficiency and GILZ expression. After resting, transfected cells can be exposed to 1 µM CORT for 24 h. Equal amount of cDNA isolated from control and GILZ overexpressing cells can be used for gene expression studies by Pathway-specific PCR arrays ($RT^2$ Neurotrophins & Receptors and Apoptosis) to identify changes in genes related to survival and death of neurons (Qiagen Inc, Germantown, Md.).

Cortisol treatment has been shown to mediate dose-dependent, bimodal effects on neuronal cell viability and proliferation. Specifically, the protective responses at low GC concentration is attributed to MR mediated transactivation. Pertinent to this study, in mouse hippocampal HT-22 cells that only express GR, GILZ was upregulated only in cells stably transfected with MR. Hence, the GILZ mRNA can be upregulated in PRCN exposed to low dose CORT via MR. In lymphocytes, much like GC, GILZ regulated apoptosis by modulating the ratio of anti-apoptotic ($Bcl_2$, $Bcl_{xL}$) to pro-apoptotic (Bax) molecules. Hence, the GILZ overexpression can suppress pro-apoptotic genes even in PRCN exposed to high dose of corticosterone.

Example 22

Pro-Inflammatory Role for Elevated GC in the CNS

Although traditionally conceptualized as anti-inflammatory agents, considerable evidence support a potent pro-inflammatory role for elevated GC in the CNS. This has been partially attributed to the reduced GR mediated transactivation of anti-inflammatory genes such as GILZ. GILZ overexpression or supplement suppressed inflammatory cytokines and pathology in models of arthritis and colitis.

Adult C57BL/6 mice (Jackson Laboratory, Bar Harbor, Me.) were administered LPS (Sigma Aldrich, MO) intraperitoneally at 250 mg/kg for 6 days. Serial 5µ thick coronal sections of brain from naïve and LPS treated mice were immunostained for GILZ using TSC22D3 mAb (Catalog #: H00001831, Abnova, Walnut, Calif.). The peroxidase conjugated streptavidin biotin method was used for detection and brown staining was considered positive. Staining specificity was confirmed by incubation with secondary antibody alone. Total RNA isolated from brain homogenates was reverse transcribed. Equal amount of cDNA was used for amplification of GILZ, CD14, CD4 and β-actin using SYBR green/Rox qPCR mix (SA Biosciences) on the ABI 7000 system (Applied Biosystem).

```
Primers used were:
F-βActin:
                                   (SEQ ID NO: 32)
   5'TCATGAAGTGTGACGTTGACATCCGTA3'

R-βActin:
                                   (SEQ ID NO: 46)
   5'CCTAGAAGCATTTGCGCTGCACGATGG3'  (102 bp);

F-CD14:
                                   (SEQ ID NO: 47)
   5'GATGACATGGTGAAGACGGC3';

R-CD14
                                   (SEQ ID NO: 48)
   5'AGGCACAGGTCATCATCAA3'  (89 bp);

F-CD4:
                                   (SEQ ID NO: 49)
   5'GAGAGTCAGCGGAGTTCT C3';

R-CD4:
                                   (SEQ ID NO: 50)
   5'CTCACAGGTCAAAGTATTGTTG (92 bp);
   and F-GILZ:
                                   (SEQ ID NO: 51)
   5'AAGGCTAGCTCCGCAGGTGC-3';

R-GILZ:
                                   (SEQ ID NO: 52)
   5'AGGTGAGCGGCA CTCGGTCT3' (120 bp).
```

Fold change was determined by the $2^{-\Delta Ct}$ method.

Results are shown in FIGS. 21A-21H. GILZ protein was observed in the cortex, hippocampus and cerebellum (FIGS. 21A & 21B). LPS induced neuroinflammation decreased GILZ expression (FIG. 21C). The GILZ mRNA in the brain homogenates correlated inversely with that of CD4 and CD14, suggesting an inverse relationship between GILZ and inflammatory markers. FIG. 21D shows the negative control. FIG. 21E shows the relative GILZ mRNA in the brain tissues of control and LPS induced mice (N=6). FIG. 21F shows gel electrophoresis of the PCR products. Correlation of GILZ mRNA with CD14 mRNA is shown in FIG. 21G and with CD4 mRNA is shown in FIG. 21H.

GILZ Overexpression Can Protect Against Neuronal Apoptosis:

Generation of conditional GILZ-transgenic (GILZ-Tg) mice: The standard Cre/loxP systems can be used to develop conditional GILZ-Tg mice. Using a Gateway-compatible ROSA26 locus targeting vector, transgenic mice can be generated overexpressing GILZ in neurons. The target vector can include mouse Tsc22d3/Gilz-1 cDNA preceded by a loxP flanked stop cassette under control of the ROSA26 promoter followed by an IRES-EGFP cDNA. Embryonic stem cell clones with gilz transgene can be identified by Southern blotting. Conditional GILZ-Tg mice can be generated by crossing mice homozygous for the loxP flanked stop cassette and Thy1-cre mice expressing cre in the neurons of the postnatal cortex and hippocampus. Controls can include wild type mice with the same genetic background as the GILZ-Tg and Thy1-cre mice. The expression of GILZ mRNA and protein in the CNS can be determined. (See quotation from vendor and Co-I support letter for Thy1-Cre).

Assessment of the GILZ-Tg mice: The phenotype of GILZ-Tg mice can be recorded with respect to body weight, length and physical appearance. Brain tissue can be assessed for gain of GILZ protein by immunohistochemistry and Western blot and by quantitative-PCR for GILZ mRNA. In addition, the neuronal structure of the brain in the GILZ-Tg mice can be assessed by Nissl staining followed by immunohistochemical staining for neurons (Neu N), microglia (Iba1) and astrocytes (GFAP).

Cellular assays: Single cell suspensions from the brain homogenates of wild type and GILZ-Tg mice can be processed to separate neuronal and glial cells by gradient centrifugation. Neuronal cell cultures can be exposed to Dex (1 µM) or $A\beta_{1-42}$ (10 µM). Cells harvested at the end of 24 h and 48 h can be assessed for inflammatory markers (NF-κB, cytokines), anti-apoptosis (Bcl2, $Bcl_{XL}$) and pro-apoptotic (caspases, Bax, Bak) protein and gene expressions by Western blot, flow cytometry and RT-PCR.

Expected results, pitfalls and alternative measures: The use of Cre-based technology is an incredibly important tool to investigate body systems in health and disease. Although Thy1-cre is expressed robustly throughout postnatal brain it is also observed in additional tissues. To differentiate real effects from artifacts and avoid misinterpretation of results, the following controls can be included: a) Cre background strains (C57BL/6), floxed controls, wild type controls and Thy1-Cre controls. Alternatively, the effects of GILZ can be assessed by introducing TAT-GILZ recombinant protein incrementally into wild type neuronal cells.

GILZ overexpression in macrophages or cardiomyocytes has been shown to enhance $Bcl_{-XL}$, suppress caspase-8 and protected against apoptosis. It was observed that the GILZ expression was reduced in the brain of mice induced neuroinflammation and the reduction correlated with the enhanced cytokines. The expressions of apoptosis markers can be higher in GILZ-Tg mice. As Aβ could potentiate GC mediated neurotoxicity and the GILZ effect is unknown, to compensate for compounding factors, the response of wild type neuronal cells exposed to high CORT will be analyzed.

Example 23

Investigation of the Role of GILZ in AD

Evidence suggests that the inflammation aggravates neurotoxicity and accelerates neurodegeneration in AD. NF-κB is a critical transcription factor that regulates inflammatory responses, Aβ generation and tau deposition. Mechanistically, GILZ exerts anti-inflammatory and anti-proliferative effects by sequestering activated p65, the functionally critical subunit of NF-κB.

Overexpression of GILZ Can Suppress Neuroinflammation and Prevent Neurodegeneration:

Selection of AD model: To address whether GILZ is mechanistically involved in the pathogenesis of AD, 5×FAD mice that overexpress GILZ in the nervous tissue can be generated. The 5×FAD is a rapid onset mouse model of AD that bears 5 mutations linked to AD and recapitulates main features of AD. In this model, Aβ deposition and inflammation are observed as early as 6 weeks. FIG. 22A-22D show elevated phosphorylated p65 correlating with gliosis and cytokines in the hippocampus and the cortex of young 5×FAD mice.

Animals: Breeding colonies of 5×FAD can be maintained in transgenic animal housing conditions in a 12-hour dark light cycle with access to food and water. Non-transgenic wild type littermates can serve as controls. Hemizygous 5×FAD mice can be crossbred to the conditional GILZ-Tg mice. Genotyping can be performed by PCR analysis of tail DNA. All experiments can be done blind with respect to the genotype of mice. The following groups of mice can be included: 1) experimental group of GILZ-Tg 5×FAD mice; control groups can include 2) 5×FAD, 3) wild type C57BL/6, 4) wild type, Thy1-Cre and 5) 5×FAD, Thy1-Cre.

All mice can be assessed for spatial learning and memory by Novel object recognition test and Morris water Maze at 4 weeks of age and then sacrificed for assessing CNS pathology, inflammation, Aβ load, gliosis and neuronal apoptosis by immunohistochemical, biochemical and molecular analyses.

Suppression of neuroinflammation by a GILZ mimetic prevented decrease in GILZ expression in the hippocampus of 5×FAD mice (see FIGS. 22A-22D). Pertinently, GILZ has been shown to exert inhibitory effects on endothelial cell adhesive function and potentially inhibit leukocyte recruitment. Since neuroinflammation occur early in 5×FAD mice, the GILZ overexpression (FIG. 22A-22D) reduce Aβ load and suppress NF-κB activation, inflammatory cytokines, PI3K signaling and prevent neuronal apoptosis.

Example 24

Decrease of Cytokines in Spinal Cord and Brain

Following spinal cord injury (SCI), inflammatory responses occur not only in the spinal cord, but also in the brain, as demonstrated by increased microglial activation (see FIG. 23A-23B and FIG. 24A-24B). As HMGB1 is upregulated by SCI and secreted by microglia, lymphocytes, macrophages and other cells, and HMGB1 is known to be associated with development of neurodegenerative diseases like Alzheimer's disease, we believe injured spinal cord-derived HMGB1 can elevate hippocampal and cortical microglial activation, which is associated with Alzheimer's disease among other neurodegenerative disorders.

Seven days following thoracic level 10 compression SCI, mice were sacrificed by approved methods and ~4 mm spinal cord lesion area and total brain tissue were homogenized in RIPA lysis buffer and inflammatory cytokine levels for IFN-γ and IL-17 were upregulated at this time point (blue bars). GILZ analog peptide given intraperitoneally on day 6 post-SCI reduced these levels in brain, and partially in the injured cord tissue (right bars) (FIG. 23A-23B). At this same time point following compression SCI, histological analysis of the hippocampus (FIG. 24A) and lesion center of the spinal cord (FIG. 24B) show prominent Iba-1+ activated microglial expression.

Example 25

Mechanisms by Which the Immune-Inflammatory Responses Induced Post-SCI Increase the Risk for Neuroinflammation in the Brain Preliminary data indicate hippocampus microglial activity is upregulated following SCI, and other reports show that HMGB1 is upregulated in the injured cord following SCI. Thus, elevated HMGB1 protein in acute injured spinal cord tissue homogenate can activate reactivity and induce pro-inflammatory responses in hippocampal and cortical microglia.

Isolation of microglia from adult mouse brain: Microglia can be isolates from the hippocampus and cortex of 6 adult C57BL/6 mice (5 weeks old). In brief, adult mice can be euthanized via approved methods, and the brains removed, and the fresh hippocampus and cortex tissue quickly dissected and enzymatically digested. The resulting digested tissue can be triturated and washed in Hank's balanced salt solution (HBSS) and centrifuged to form a pellet. The pellet can be resuspended in culture medium (DMEM/F12+10% fetal bovine serum [FBS]+1% penicillin/streptomycin) and washed again. Next the pellet can be centrifuged in a 30-70% Percoll gradient, and the microglia (visible at the 70-37% gradient interphase) will be collected and washed with HBSS. The microglia can be counted and seeded in culture medium for further experimentation.

Spinal cord injury: 8 week old female C57BL/6 mice can be randomly assigned to four groups to produce a time course of injured spinal cord tissue homogenate to treat isolated and cultured adult mouse brain microglia: 1) sham surgery group (no SCI), 2) 1 d post-SCI, 3) 3 d post-SCI, 4) 7 d and 28 d post-SCI (n=4/group=20 mice). To produce SCI in the mice, surgery and clip compression SCI can be performed. In brief, mice can be anesthetized with isoflurane, and the paraspinal muscles along the T8-T11 vertebrae can be carefully dissected and the T10 vertebra exposed. A laminectomy of the dorsal portion of the T10 vertebrae exposing the spinal cord can be performed, and a 30 g force vascular clip can be placed on the sides of the cord and carefully closed for compression. The cord can remain compressed for 1 minute, which will produce a moderate SCI.

The clip can then be removed, and the injured cord observed under the surgical microscope for confirmation of proper injury. A band of bruising and hemorrhage of blood in the cord can be visible at the location of clip compression. The muscle can be closed with sterile nylon suture, followed by the skin. The surgical site can be treated with antibacterial ointment and the mice placed in a clean home cage on a warming pad set to 37° C. to recover. The mice quickly recover from isoflurane anesthesia and bilateral paralysis of the hindlimbs can be observed as further confirmation of successful SCI. Mice in the sham surgery group can undergo all steps of the surgery except spinal cord compression.

Spinal cord isolation and homogenate preparation: Mice can be sacrificed in each group at the designated time points and transcardially perfused with normal saline. A 5 mm region of spinal cord centered over the injury site can be rapidly dissected and minced in RIPA buffer as previously described. Tissue in RIPA buffer can then be homogenized with a dounce homogenizer, the tubes centrifuged to pellet debris, and the supernatant homogenate isolated for treating microglial cultures.

HMGB1 ELISA: To test the concentration of HMGB1 from the homogenates in our SCI model, protein samples from the sham, 1 d, 3 d, 7 d and 28 d groups can be assayed using a sandwich enzyme-linked immunosorbent assay (ELISA) for mouse HMGB1 (LifeSciences Biospan, Inc.), and absorbance read on a plate reader (BioTek, Inc.) and concentrations determined against a standard control curve. Purified recombinant mouse HMGB1 protein (Biolegend, Inc.) can be assayed as a positive control.

Microglial treatment with spinal cord homogenates: Isolated microglia can be seeded in 12-well culture dishes at a density of $2.5 \times 10^5$ cells/ml in minimal essential medium (MEM) supplemented with 1% fetal bovine serum (FBS) and 1% penicillin (100 U/ml)/streptomycin (100 μg/ml) and grown to ~80% confluence. HMGB1 is known to increase within hours in the injured spinal cord. To test the effects of SCI homogenates on microglial activation and response, the experiment as described in Table 3 will be performed.

TABLE 3

Experimental Design

| | SC Homogenates (days post-SCI) | | | | | Hippocampal and cortical |
|---|---|---|---|---|---|---|
| | Sham | 1 | 3 | 7 | 28 | microglial isolation |
| Number of mice | 4 | 4 | 4 | 4 | 4 | 6 |
| Microglial Treatment Groups | | | | | | |
| Normal culture medium only | | | | | | |
| 1 μg/ml lipopolysaccharide (LPS) | | | | | | |
| 1% SC homogenate | | ✓ | ✓ | ✓ | ✓ | |
| 10% SC homogenate | | ✓ | ✓ | ✓ | ✓ | |
| 20% SC homogenate | | ✓ | ✓ | ✓ | ✓ | |
| 3 μM HMGB1 w/o neutralizing antibody | | | | | | |
| 3 μM HMGB1 w/ neutrailizing antibody | | | | | | |

SC = Spinal Cord

Three concentrations of homogenates in culture medium (1%, 10% and 20% vol/vol) can be applied to microglial cells and incubated at 37° C. and 5% $CO_2$ for 12 h or 24 h The concentrations are extrapolated from previous studies suggesting that 0.3 µM of HMBG1 inhibiting Aβ phagocytosis by microglia. Normal culture medium only can serve as a negative control and 1 µg/ml lipopolysaccharide (LPS), a known stimulator of microglial activity, in normal culture medium will serve as a positive control. Cultures treated with known concentrations of HMBG-1 (1-3 µM) in the presence or absence of monoclonal antibody against HMBG1 can be included as a means of confirmation of the role of HMBG1 in SCI homogenate.

Assessment of Microglial Responses:

Immunocytochemistry: Twelve hours after culture, microglia can be gently rinsed with PBS, and fixed with 4% paraformaldehyde. Cells can then be immunostained for TLR-4, the chemokine ligand CCL12, the costimulatory receptors CD80 and CD86 and nuclear NF-κB p65. Furthermore, cells can be incubated with Hoechst 33342 to visualize microglial nuclei. Labeled fluorescence can be detected using a laser scanning confocal microscope LSM 510 (Carl Zeiss, Jena, Germany).

ELISA for cytokines: The concentrations of inflammatory cytokines IL-6 and TNF-α in culture supernatants harvested at the end of 12 h, 24 h and 48 h can be assessed using appropriate OptEIA kits (BD Biosciences).

Quantitative RT-PCR (qRT-PCR): Total RNA isolated from cultured microglia can be reverse transcribed and qRT-PCR will be performed in ABI 7000 system using the Superscript III Platinum SYBR Green One-Step qRT-PCR kit (Invitrogen), as described.

```
Primers:
TLR4:
(FP 5'-GCTTTCACCTCTGCCTTCAC-3';   (SEQ ID NO: 53)

RP 5'-GA AACTGCCATGTTTGAGCA-3'),  (SEQ ID NO: 54)

IL-6:
(FP 5'-AGTTGCCTTCTTGGGACTGA-3';   (SEQ ID NO: 55)

RP 5'-TCCACGATTTCCCAGAGAAC-3'),   (SEQ ID NO: 56)
and

RPS3:
(FP 5'AATGAAC CGAAGCACACCATA-3';  (SEQ ID NO: 57)

RP 5'-ATCAGAGAGTTGACCGCAGTT-3').  (SEQ ID NO: 58)
```

Product specificity can be confirmed by melting curve analysis and visualization of single, appropriately sized band on a 2% agarose gel. Gene expression levels can be quantified using a cDNA standard curve and data were normalized to RPS3, a housekeeping gene that was unaffected by traumatic injury. Ability of HMGB1 primed microglia to respond to Aβ$_{1-42}$ peptide:

Cultures of microglia exposed to spinal cord homogenates for 24 h as above, can be rested in serum free media for 24 h. The cells can then be washed in fresh culture medium and exposed to Aβ$_{1-42}$ at a final concentration of 10 µM/well and incubated for 4 h or 48 h. Cells and conditioned media will be harvested and stored for further analysis. Relative ATP concentration can be measured using the CTG kit (Promega) as described. Conditioned media collected can be assessed for specific cytokines using the OptEIA kits (BD Biosciences). The cell surface expression of activation markers including MHC Class II, CD80 and CD 86 can be assessed by immunocytochemistry and flow cytometry.

The concentration of HMBG1 in the spinal cord homogenates has been shown to be elevated within few hours after acute-SCI in both humans and animal models. Furthermore, the level remains high for extended periods in chronic SCI. The hippocampal microglia have been shown to express elevated CCL12 in mice day 12 post-SCI. HMBG1 has been shown to activate microglia via TLR-4/NF-κB pathway. Hence, the TLR-4, CCL12 and nuclear p65 can be elevated in microglia exposed to spinal cord homogenates obtained day 3-14 post-SCI. Previously, HMGB1 exposure has been shown to prime hippocampal microglial response to LPS. Since Aβ reactive T cells have been shown to increase with aging, increase can be due to microglia function as efficient Aβ presenting cells. The SCI homogenate primed hippocampal and cortical microglia can exhibit activated phenotype.

Example 26

Investigation of Suppression of Activated NF-κB Mediated Inflammation Following SCI as a Measure to Prevent Hippocampal Microglial Activation The NF-κB pathway is important for the regulation of inflammation and apoptosis following SCI. The clinical benefits of the commonly prescribed high-dose methylprednisolone steroid in the management of SCI, is compromised by adverse effects. Glucocorticoid induced leucine zipper (GILZ) is a recently identified protein that mimics only the beneficial effects of steroids and act by inhibiting the NF-κB p65 protein. GILZ overexpression has been shown to suppress tissue damage in SCI. The suppression of NF-κB p65 can inhibit gliosis at the injury site in SCI and prevent activation of hippocampal microgliosis.

This Example evaluates the efficacy of peptide analogs of GILZ (GA) in inhibiting microgliosis at injury sites and in the hippocampus of mice subjected to SCI (see Table 4). Adult C57BL/6 mice (Jackson Laboratory, Bar Harbor, Me.) can be administered lipopolysaccharide (LPS) (Sigma Aldrich, Mo.) intraperitoneally at 250 mg/kg for 6 days. Serial 5µ thick coronal sections of brain from naïve and LPS treated mice can be immunostained for GILZ using TSC22D3 mAb (Catalog #: H00001831, Abnova, Walnut, Calif.). The peroxidase conjugated streptavidin biotin method can be used for detection and brown staining was considered positive. Staining specificity was confirmed by incubation with secondary antibody alone. RNA isolated from brain homogenates was reverse transcribed.

TABLE 4

Experimental Design
Table 2. Experimental design for Aim 2

| Groups | Biochemical Analysis n = 6/group = 36 mice | Histologic Analysis n = 6/group = 36 mice |
|---|---|---|
| Sham surgery 7 d SCI + saline 7 d SCI + GA 1 7 d SCI + GA2 7 d SCI + control peptide 7 d SCI + TAT carrier | Analyses: Cytokine ELISA | Analyses: Brain and spinal cord microglial stereologic quantification and immunofluorescence labeling |

GA = GILZ analog.
SCI = spinal cord injury

Spinal cord injury and treatment: SCI surgery can be performed as described previously. To test the effect of GA peptides on CNS microgliosis post-SCI, C57BL/6 mice can be randomly assigned to six groups: 1) sham surgery, 2) SCI+saline, 3) SCI+GA peptide 1, 4) SCI+GA peptide 2, 5) SCI+non-specific peptide (control) and 6) SCI+carrier tag (GAG-TAT) injection (control) (n=12 per group [6 for biochemistry, 6 for histologic analysis]×6 groups=72 mice).

GA preparation and administration: GA can be synthesized as peptide amides with amino terminal acetylation. The GA can be covalently synthesized with a cell penetrating peptide for intracellular delivery. Based on our studies in the AD model, GA1 (19 mM) and GA 2 (22 mM) can be administered intraperitoneally on days 1 and 7 post SCI. Brain tissues harvested at each time-point and end of the study can be evaluated for inflammation and neuronal loss/protection. Control groups can include untreated SCI and scrambled peptide treated mice.

Protein preparation for biochemical analysis: After 7 days post-surgery, 6 mice per group designated for biochemical analysis of NF-κB-mediated inflammation can be transcardially perfused with saline and brain and spinal cord tissue isolated and prepared as described previously. In brief, the brain can be dissected and the cortex and hippocampus removed and placed in RIPA lysis buffer, and homogenized with a dounce homogenizer. The lysed tissue can be centrifuged and the supernatant collected. The protein concentration of the supernatant can be determined with bichincionic acid assay (BCA, Pierce).

ELISA for cytokine expression analysis: Spinal cord and brain homogenates can be assessed for cytokines (TNF-α, IL-12, IFN-g) and HMBG1 as described above.

Histologic assessment of brain and spinal cord microgliosis: The remaining 6 mice can be euthanized on day 7 post-surgery, transcardially perfused with saline followed by perfusion with 4% paraformaldehyde (PFA) for fixation and histological assessment of microglial activation in the brain and spinal cord as described previously. Briefly, perfused brain and spinal cord tissue can be dissected and post-fixed in 4% PFA for 24 hours. Then, the tissue can be placed in a 30% sucrose in 0.1 M phosphate buffered saline (PBS) for cryopreservation, and then embedded in Optimal Cutting Temperature medium for subsequent cryostat sectioning. Tissue can be serially sectioned at 20 um and mounted on Superfrost Plus slides (Fisher Scientific) Immunofluorescence labeling will be performed as previously described. Briefly, brain and spinal cord sections can be immunolabeled for microglia with rabbit anti-Iba1 (1:500; Wako) overnight at 4° C., and the following day, the sections will be incubated with fluorophore-conjugated goat anti-rabbit secondary antibody (1:200; Jackson ImmunoResearch Lab). Sections will then be incubated with Hoechst 33342 (1:500, Sigma-Aldrich) in PBS for nuclear labeling, washed and coverslip mounted with Fluoromount G. In adjacent slides in the series, immunohistochemistry for Iba1 (1:500; Abcam, Inc.) can also be performed for unbiased stereologic quantification of reactive microglia using a StereoInvestigator system (Microbrightfield, Inc.) as previously described. Pre-immune serum can be used as a control to confirm antibody specificity. Images can be obtained with an epifluorescent microscope (Nikon) and microglial reactivity can be assessed as a percentage of fluorescent labeling area per unit tissue area.

Expected results: We have shown that both GA1 and GA2 suppressed gliosis and proinflammatory cytokines in the brain homogenates of mice subjected to lipopolysaccharide induced neuroinflammation. Treatment with GA1 or GA2 can suppress inflammation at site of injury and this will be reflected in a decrease in the number of microglia in the hippocampus.

The invention claimed is:

1. A pharmaceutical composition comprising a polypeptide from 8 to 12 amino acid residues, the polypeptide comprising the sequence of XPXXP, wherein P is proline; and the first X is A or K, and the third X is Q, A, or S, wherein the polypeptide forms a $PP_{II}$ helical conformation and interacts with p65 residues $F^{534}$ and $F^{542}$.

2. The pharmaceutical composition of claim 1, wherein the polypeptide comprises the sequence of APKPYQPRG (SEQ ID NO: 29).

3. The pharmaceutical composition of claim 1, wherein the polypeptide comprises the sequence of EPAPXXPXX (SEQ ID NO: 1),
   and wherein the polypeptide comprises a sequence selected from the group consisting of EPAPLAPYG (SEQ ID NO: 13), EPAPYQPEG (SEQ ID NO: 24), EPAPESPQV (SEQ ID NO: 17), and EPAPEQPDG (SEQ ID NO: 18).

4. The pharmaceutical composition of claim 3, wherein the polypeptide comprises the sequence of EPAPLAPYG (SEQ ID NO: 13).

5. The pharmaceutical composition of claim 3, wherein the polypeptide comprises the sequence of EPAPYQPEG (SEQ ID NO: 24).

6. The pharmaceutical composition of claim 3, wherein the polypeptide comprises the sequence of EPAPESPQV (SEQ ID NO: 17).

7. The pharmaceutical composition of claim 3, wherein the polypeptide comprises the sequence of EPAPEQPDG (SEQ ID NO: 18).

8. The pharmaceutical composition of claim 1, wherein the first X is A.

9. The pharmaceutical composition of claim 1, wherein the first X is K.

10. The pharmaceutical composition of claim 1, wherein the third X is Q.

11. The pharmaceutical composition of claim 1, wherein the third X is S.

12. The pharmaceutical composition of claim 1, wherein the first X is A, and the third X is Q, S, or A.

13. The pharmaceutical composition of claim 1, wherein the first X is A, and the third X is Q.

14. The pharmaceutical composition of claim 1, wherein the first X is A, and the third X is S.

15. The pharmaceutical composition of claim 1, wherein the first X is A, and the third X is A.

16. The pharmaceutical composition of claim 1, wherein the first X is K, and the third X is Q.

17. A pharmaceutical composition comprising a polypeptide from 8 to 12 amino acid residues, the polypeptide comprising a tetrapeptide having the sequence of PXXP, wherein P is proline; and the second X is Q or S, wherein the polypeptide forms a $PP_{II}$ helical conformation and interacts with p65 residues $F^{534}$ and $F^{542}$.

18. The pharmaceutical composition of claim 17, wherein the second X is Q.

19. The pharmaceutical composition of claim 17, wherein second X is S.

* * * * *